US011065214B1

(12) United States Patent
Jacobson et al.

(10) Patent No.: US 11,065,214 B1
(45) Date of Patent: Jul. 20, 2021

(54) COMBINATION THERAPIES WITH DISULFIRAM

(71) Applicant: Spring Discovery, Inc., San Carlos, CA (US)

(72) Inventors: Rachel Jacobson, Belmont, CA (US); Wendy Cousin, Belmont, CA (US); An Nguyen, Seattle, WA (US); Tempest Plott, San Mateo, CA (US); William Van Trump, San Francisco, CA (US); Dat Nguyen, Redwood City, CA (US); Daniel Chen, San Mateo, CA (US); Jarred Heinrich, Menlo Park, CA (US); Ben Komalo, San Francisco, CA (US); Lauren Nicolaisen, Redwood City, CA (US); Christian Elabd, Belmont, CA (US)

(73) Assignee: Spring Discovery, Inc., San Carlos, CA (US)

( * ) Notice: Subject to any disclaimer, the term of this patent is extended or adjusted under 35 U.S.C. 154(b) by 0 days.

(21) Appl. No.: 17/149,557

(22) Filed: Jan. 14, 2021

Related U.S. Application Data

(60) Provisional application No. 63/080,639, filed on Sep. 18, 2020.

(51) Int. Cl.
*A61K 31/145* (2006.01)
*A61K 31/05* (2006.01)

(52) U.S. Cl.
CPC ............ *A61K 31/145* (2013.01); *A61K 31/05* (2013.01)

(58) Field of Classification Search
CPC ..... A61K 31/145; A61K 31/05; C08G 63/191
See application file for complete search history.

(56) References Cited

U.S. PATENT DOCUMENTS

| | | | |
|---|---|---|---|
| 6,288,110 B1 * | 9/2001 | Marikovsky | A61P 35/00 514/483 |
| 10,886,008 B2 | 1/2021 | Kamens et al. | |
| 2005/0181354 A1 | 8/2005 | Estep, III | |
| 2009/0274677 A1 * | 11/2009 | Isaacs | A61K 8/498 514/1.1 |
| 2011/0196616 A1 | 8/2011 | Gunn | |
| 2015/0139973 A1 * | 5/2015 | Steinfeld | A61K 31/375 424/94.4 |
| 2016/0292380 A1 | 10/2016 | Cho et al. | |
| 2017/0342496 A1 | 11/2017 | Zhang et al. | |
| 2019/0034581 A1 | 1/2019 | Aliper et al. | |
| 2019/0228840 A1 | 7/2019 | Kamens et al. | |
| 2019/0381132 A1 * | 12/2019 | Shu | C07K 14/47 |

FOREIGN PATENT DOCUMENTS

| | | |
|---|---|---|
| WO | WO-2012164525 A2 | 12/2012 |
| WO | WO-2014175542 A1 | 10/2014 |
| WO | WO-2016086008 A1 | 6/2016 |
| WO | WO-2017049103 A1 | 3/2017 |
| WO | WO-2018081309 A1 | 5/2018 |
| WO | WO-2019094053 A1 | 5/2019 |
| WO | WO-2019147725 A1 | 8/2019 |
| WO | WO-2020006229 A1 | 1/2020 |

OTHER PUBLICATIONS

Aliper, et al. Deep learning applications for predicting pharmacological properties of drugs and drug repurposing using transcriptomic data. Mol Pharm. Jul. 5, 2016; 13(7): 2524-2530.

Carpenter et al.: CellProfiler: image analysis software for identifying and quantifying cell phenotypes. Genome Biology. 7(10):R100 (2006).

Cheung et al.: Cinnamic compound metabolism in human skin and the role metabolism may play in determining relative sensitisation potency. J Dermatol Sci. 31(1):9-19 (2003).

Cole, et al. Predicting brain age with deep learning from raw imaging data results in a reliable and heritable biomarker. Neuroimage. Dec. 2017;163:115-124.

Conboy, et al. Heterochronic parabiosis for the study of the effects of aging on stem cells and their niches. Cell Cycle vol. 11, 2012—Issue 12: 2260-2267.

Conboy, et al. Rejuvenation of aged progenitor cells by exposure to a young systemic environment. Nature. Feb. 17, 2005;433(7027):760-4.

Deng, et al. ImageNet: A large-scale hierarchical image database. 2009 IEEE Conference on Computer Vision and Pattern Recognition (Jun. 2009), pp. 248-255.

D'Orazio, et al. UV radiation and the skin. Int J Mol Sci. Jun. 2013; 14(6): 12222-12248.Published online Jun. 7, 2013.doi: 10.3390/ijms140612222.

Harrison, et al. Rapamycin fed late in life extends lifespan in genetically heterogeneous mice. Nature. Jul. 16, 2009; 460(7253): 392-395.

He, et al. Deep Residual Learning for Image Recognition. (Submitted on Dec. 10, 2015); The IEEE Conference on Computer Vision and Pattern Recognition (CVPR), 2016, pp. 770-778.

Hu et al.: FDA-approved disulfiram inhibits pyroptosis by blocking gasdermin D pore formation. Nature Immunology. 21(7):736-745 (2020).

IDTechEx. AI to accelerate drug discovery for aging and age-associated diseases. Available at https://www.onartificialintelligence.com/journal/print-articles.asp?articleids=11058. Accessed on Jan. 25, 2018.

(Continued)

*Primary Examiner* — Umamaheswari Ramachandran
(74) *Attorney, Agent, or Firm* — Wilson Sonsini Goodrich & Rosati

(57) ABSTRACT

Disclosed herein are compositions and methods for increasing lifespan, for preventing or treating a disease including an aging-related disorder, for reducing a symptom of aging, and/or boosting an immune system in a mammal. Also disclosed herein are compositions and methods for improving effectiveness of a vaccine in a mammal. The compositions comprise, at least, a therapeutically effective amount of disulfiram and one or more additional ingredients.

18 Claims, 5 Drawing Sheets

(56) References Cited

OTHER PUBLICATIONS

Kamentsky et al.: Improved structure, function and compatibility for CellProfiler: modular high-throughput image analysis software. Bioinformatics. 27(8):1179-80 (2011).

Kingma, et al. Adam: A Method for Stochastic Optimization. Published as a conference paper at the 3rd International Conference for Learning Representations, San Diego, 2015.

Langer. New methods of drug delivery. Science 249:1527-1533 (1990).

Lin et al.: Disulfiram can inhibit MERS and SARS coronavirus papain-like proteases via different modes. Antiviral Res. 150:155-163 (2018).

Liu et al.: Inflammasome-activated gasdermin D causes pyroptosis by forming membrane pores. Nature. 535(7610):153-158 (2016).

Ljosa et al.: Comparison of methods for image-based profiling of cellular morphological responses to small-molecule treatment. J. Biomol. Screening. 18(10):1321-1329 (2013).

Loo et al.: Blockage of drug resistance in vitro by disulfiram, a drug used to treat alcoholism. J Natl Cancer Inst. 92(11):898-902 (2000).

Lopez-Berestein et al.: Liposomes in the therapy of infectious diseases and cancer. Liss, New York. pp. 353-365 (1989).

Mark-Anthony, et al. Cell Painting, a high-content image-based assay for morphological profiling using multiplexed fluorescent dyes. Nat Protoc. Sep. 2016; 11(9): 1757-1774.

McCarthy: Disulfiram inhibits inflammatory gatekeeper protein: Could it be helpful in COVID-19. Boston Children's Press Release. May 10, 2020.

PCT/US2019/014826 International Preliminary Report on Patentability dated Aug. 6, 2020.

PCT/US2019/014826 International Search Report and Written Opinion dated Apr. 11, 2019.

Pelaz et al.: Diverse applications of nanomedicine. ACS Publications. 11:2313-2381 (2017).

Phillip, et al. Biophysical and biomolecular determination of cellular age in humans. Nature Biomedical Engineering vol. 1, Article No. 0093 (2017).

Puri et al.: Lipid-based nanoparticles as pharmaceutical drug carriers: from concepts to clinic. Critical Reviews™ in Therapeutic Drug Carrier Systems. 26(6):523-580 (2009).

Putin, et al. Deep biomarkers of human aging: Application of deep neural networks to biomarker development. Aging (Albany NY). May 2016; 8(5): 1021-1030.

Sauna et al.: The molecular basis of the action of disulfiram as a modulator of the multidrug resistance-linked ATP binding cassette transporters MDR1 (ABCB1) and MRP1 (ABCC1). Mol Pharmacol. 65(3):675-684 (2004).

Treat et al.: In Liposomes in the Therapy of Infectious Disease and Cancer. Lopez-Berestein and Fidler (eds.), Liss, New York, pp. 353-365 (1989).

Uno, et al. Lifespan-regulating genes in *C. elegans*. NPJ Aging Mech Dis. 2016; 2: 16010.

U.S. Appl. No. 16/255,366 Final Office Action dated Jun. 26, 2020.

U.S. Appl. No. 16/255,366 Office Action dated Apr. 1, 2019.

U.S. Appl. No. 16/255,366 Office Action dated Feb. 13, 2020.

U.S. Appl. No. 16/255,366 Office Action dated Sep. 18, 2019.

Viola-Rhenals et al.: Recent Advances in Antabuse (Disulfiram): The Importance of its Metal-binding Ability to its Anticancer Activity. Curr Med Chem. 25(4):506-524 (2018).

Wakasar: General overview of lipid-polymer hybrid nanoparticles, dendrimers, micelles, liposomes, spongosomes and cubosomes. J Drug Target. 26(4):311-318 (2018).

Weindruch, et al. The retardation of aging in mice by dietary restriction: longevity, cancer, immunity and lifetime energy intake. J Nutr. Apr. 1986;116(4):641-54.

Ianevski et al.: SynergyFinder: a web application for analyzing drug combination dose-response matrix data. Bioinformatics. 33(15:2413-2415 (2017).

Lederer et al.: Additive Dose Response Models: Explicit Formulation and the Loewe Additivity Consistency Condition. Frontiers in Pharmacology. 9:31 (2018) 11 pages.

Zheng. synergyfinder: Calculate and Visualize Synergy Scores for Drug Combinations. R package version 2.4.13. http://synergyfinder.org/ (2021).

\* cited by examiner

| Disulfiram concentration (µM) | DISULFIRAM ALONE | TBHQ concentration (µM) | | | | | | |
|---|---|---|---|---|---|---|---|---|
| | | 2.19 | 3.29 | 4.94 | 7.41 | 11.11 | 16.67 | 25.00 |
| 0.00 | | | | | | | | |
| 5.27 | | 1.45 | 1.27 | 2.19 | 1.18 | 0.96 | 2.51 | 44.78 |
| 7.90 | | 1.24 | 1.23 | 1.60 | 0.90 | 1.26 | 70.78 | 91.57 |
| 11.85 | | 1.11 | 1.22 | 7.98 | 79.40 | 175.68 | 298.44 | 159.46 |
| 17.78 | | 1.84 | 14.15 | 156.16 | 225.36 | 355.94 | 250.18 | 207.06 |
| 26.67 | | 1.46 | 2.68 | 5.33 | 5.07 | 4.66 | 5.08 | 4.24 |
| 40.00 | | 2.12 | 1.47 | 4.38 | 4.42 | 3.43 | 3.55 | 4.61 |
| 60.00 | | 1.04 | 1.06 | 2.28 | 1.43 | 1.16 | 1.26 | 1.65 |

| | DSF+TBHQ | | | | | | | |
|---|---|---|---|---|---|---|---|---|
| | 0.00 | 2.19 | 3.29 | 4.94 | 7.41 | 11.11 | 16.67 | 25.00 | DSF+ Compound |
| Average IC50 | 100.00% | 109.48% | 74.52% | 61.16% | 49.80% | 48.61% | 25.05% | 62.53% | 63.26% |
| T-test | | 0.369 | 0.044 | 0.017 | 0.001 | 0.005 | 0.002 | 0.610 | 0.018 |

COMBINATION THERAPIES WITH DISULFIRAM

CROSS-REFERENCE

This application claims priority to U.S. Provisional Application No. 63/080,639 filed Sep. 18, 2020, the contents of which is incorporated by reference herein in its entirety.

BACKGROUND

Of the approximately 150,000 human deaths per day, approximately two-thirds are due to age-related causes. Aging leads to functional deterioration and progressive decline across multiple tissues, organs, and systems, including the immune system, that arise from the progressive accumulation of cellular and tissue damage. This damage may be attributed, in part, to dysfunction or disruption in one or more signaling pathways. Accordingly, there remains an unmet need for compositions and methods that stop, slow, or reverse these dysfunctions or disruptions and are capable of thereby treating aging-related disorders and/or reducing symptoms of aging.

SUMMARY

The present invention addresses this need. Accordingly, the present disclosure relates to compositions and methods for increasing lifespan, for preventing or treating a disease including an aging-related disorder, for reducing a symptom of aging, and/or boosting an immune system in a mammal. The present disclosure additionally relates to compositions and methods for improving effectiveness of a vaccine in a mammal.

An aspect of the present disclosure is a method for inhibiting and/or reducing pyroptotic cell death in a cell. The method comprises contacting the cell with an active agent that is disulfiram and a potentiating ingredient that is tert-Butylhydroquinone (TBHQ), thereby inhibiting and/or reducing pyroptotic cell death.

In some embodiments, the disulfiram and TBHQ are included in one composition and the composition consists essentially of disulfiram and TBHQ. In some cases, the composition further comprises one or more additional ingredients from Table 1.

In various embodiments, the method comprises contacting the cell with a first composition consisting essentially of disulfiram and contacting the cell with a second composition consisting essentially TBHQ. In some cases, the either or both of the first composition and the second composition further comprises one or more additional ingredients from Table 1.

In embodiments, inhibiting and/or reducing pyroptotic cell death in the cell increases the lifespan of the cell.

In some embodiments, the amount of disulfiram is from about 5 mg to about 500 mg and the amount of TBHQ is from about 0.02% to about 56% by weight of disulfiram.

In various embodiments, the TBHQ further potentiates disulfiram's ability to treat acute lung injury (ALI), acute respiratory distress syndrome (ARDS), idiopathic pulmonary fibrosis, chronic obstructive pulmonary disease, dry eye, actinic keratosis, alopecia, and/or skin cancer.

In embodiments, the TBHQ further potentiates disulfiram's ability to inhibit and/or reduce a pathological inflammatory response, alter a T-cell's age, and/or alter mitochondrial function in the cell.

Another aspect of the present disclosure is a method for boosting activity of an immune cell. The method comprises contacting the immune cell with an active agent that is disulfiram and a potentiating ingredient that is tert-Butylhydroquinone (TBHQ), thereby boosting activity of an immune cell.

In some embodiments, the disulfiram and TBHQ are included in one composition and the composition consists essentially of disulfiram and TBHQ. In some cases, the composition further comprises one or more additional ingredients from Table 1. The method may comprise contacting the cell with a first composition consisting essentially of disulfiram and contacting the cell with an at least second composition consisting essentially TBHQ. Either or both of the first composition and the second composition further comprises one or more additional ingredients from Table 1.

In various embodiments, boosting activity of an immune cell increases an effective immune response against an infectious agent and/or an atypical cell.

In embodiments, boosting activity of an immune cell improves the immune cell's response against a component contained in a vaccine, wherein the component contained in the vaccine is an antigen obtained from, related to, homologous to, or expressed by an infectious agent.

In some embodiments, boosting activity of an immune cell comprises inhibiting a pathological immune response. In some cases, boosting activity of an immune cell minimizes overactive immune cell activity.

In various embodiments, the amount of disulfiram is from about 5 mg to about 500 mg and the amount of TBHQ is from about 0.02% to about 56% of the weight of the disulfiram.

Yet another aspect of the present disclosure is a composition consisting essentially of an active agent that is disulfiram and a potentiating ingredient that is tert-Butylhydroquinone (TBHQ). The amount of disulfiram is from about 5 mg to about 500 mg and the amount of TBHQ is from about 0.02% to about 56% of the of the disulfiram.

It shall be understood that different aspects and/or embodiments of the invention can be appreciated individually, collectively, or in combination with each other. Various aspects and/or embodiments of the invention describe herein may be applied to any of the uses set forth below and in other methods for increasing lifespan in a mammal. Any description herein concerning a specific composition and/or method apply to and may be used for any other specific composition and/or method as disclosed herein. Additionally, any composition disclosed herein is applicable to any herein-disclosed method. In other words, any aspect or embodiment described herein can be combined with any other aspect or embodiment as disclosed herein.

BRIEF DESCRIPTION OF DRAWINGS

FIG. 1A shows cytokine levels from the supernatant of vesicular stomatitis virus encoding a red fluorescent protein (rVSV-ΔG-mCherry)-infected cells (infected at 10×MOI); asterisks indicate statistical significance relative to untreated control cells. Data is normalized by total cell count. In FIG. 1B and FIG. 1C, respectively, show reticularity measurements of mitochondria and aging scores in T cells. In FIG. 1B and FIG. 1C, horizontal bars represent the distribution of untreated controls from younger and older donors; the solid line represents the median and the lower and upper dashed lines represent the $25^{th}$ and $75^{th}$ quartiles, respectively. The line graph represents the median and 95% CI for treated cells, with statistical significance relative to untreated control cells indicated by asterisks. In FIG. 1D, "on-age" and "off-age" scores for T cells treated with either disulfiram or dimethyl fumarate. Distributions for younger and older control (untreated) cells are plotted using a Gaussian kernel density estimation. Statistical significance relative to untreated control cells is indicated by the following: *, P<0.5; , P<0.001; *, P<0.0001. IL, interleukin; MCP1, monocyte chemoattractant protein 1; MOI, multiplicity of infection; PBMC, peripheral blood mononuclear cell; TNF, tumor necrosis factor.

FIG. 4A is a table of synergy ratio of actual/expected effect at each concentration of TBHQ and disulfiram; cells in grey indicate positive synergy. FIG. 4B and FIG. 4C are graphs showing average synergy at different concentrations of TBHQ and disulfiram.

DETAILED DESCRIPTION OF THE INVENTION

Figure 1A:
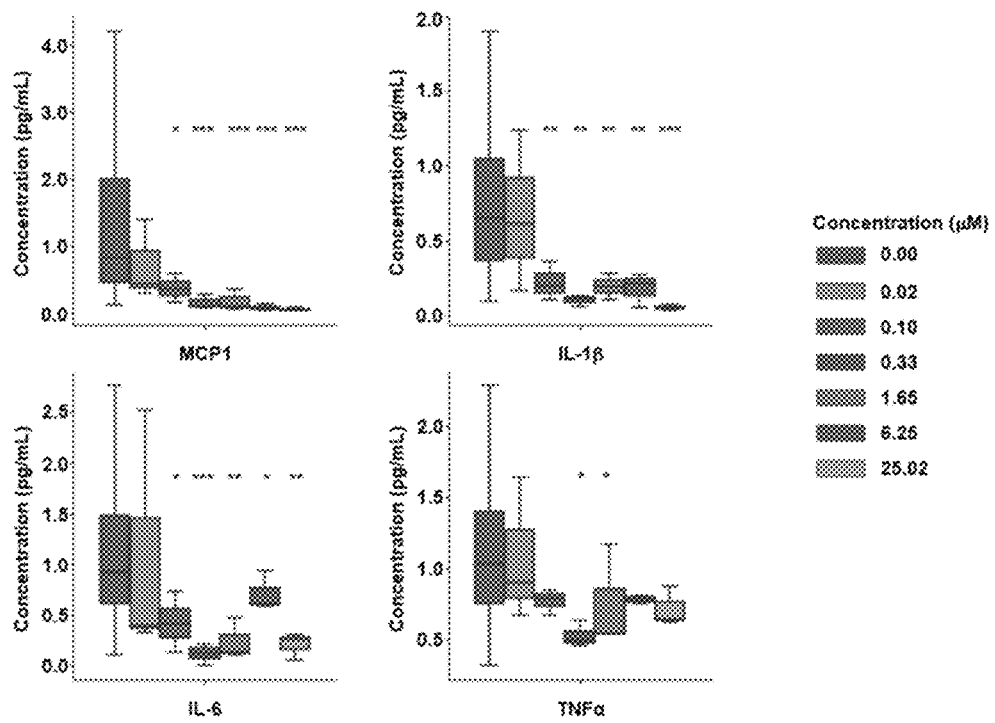
FIG. 1A to FIG. 1D show data obtained when virally infected cells were treated with a disulfiram.

The present disclosure relates to compositions and methods for increasing lifespan, for preventing or treating a disease including an aging-related disorder, for reducing a symptom of aging, and/or boosting an immune system in a mammal. The present disclosure additionally relates to compositions and methods for improving effectiveness of a vaccine in a mammal.

1. Compounds and Compositions

The methods of the present disclosure comprise administering to a mammal a therapeutically effective amount of an active ingredient that is disulfiram and a potentiating ingredient that is tert-Butylhydroquinone (TBHQ) or comprise contacting a cell (in vivo, in vitro, or ex vivo) with an active ingredient that is disulfiram and a potentiating ingredient that is TBHQ.

Disulfiram is a specific inhibitor of an aldehyde-dehydrogenase (ALDH1). Disulfiram was approved by the US Food and Drug Administration in 1951 for alcohol aversion therapy after researchers observed that it induced the effects of a hangover after alcohol consumption. Disulfiram blocks the major metabolic reaction that converts alcohol into acetaldehyde. Disulfiram inhibits pyroptosis of a cell by inhibition of gasdermin D.

As used herein, the term disulfiram includes disulfiram itself and any of its metabolites and/or derivatives. Examples of metabolites include diethyldithiocarbamate, diethyl-amine, and carbon disulfide.

In each aspect and embodiment of the present disclosure, the active agent is disulfiram and the potentiating ingredient is TBHQ. TBHQ has the following chemical identifiers: CAS 1948-33-0, DrugBank DB07726, MedChem HY-100489, and SelleckChem S4990. TBHQ protects against Doxorubicin (DOX)-induced cardiotoxicity through activation of nuclear factor erythroid 2-related factor 2 (NrF2). TBHQ is also an ERK activator, and rescues Dehydrocorydaline (DHC)-induced cell proliferation inhibition in melanoma.

TBHQ is generally recognized as safe (GRAS; e.g., by the FDA), is listed in the FDA inactive ingredient database (IID (see, the World Wide Web at accessdata.fda.gov/scripts/cder/iig/index.cfm), and/or is included in the FDA's Substances Added to Food list (see, the World Wide Web at cfsanappsexternal.fda.gov/scripts/fdcc/?set=FoodSubstances and the regulations set forth in 21 CFR 73, 74, 172, 173, 181, 182, and 184, the contents of each of which is incorporated by reference in its entirety).

As used herein, the term TBHQ includes TBHQ itself and any of its metabolites, derivatives, and/or precursors. Examples of TBHQ metabolites include TBHQ-glucuronide and TBHQ-sulfate. An example of a TBHQ precursor is butylated hydroxyanisole (BHA).

A composition of the present disclosure comprises an active agent that is disulfiram and a potentiating ingredient that is TBHQ. A plurality of compositions of the present disclosure may comprise a first composition comprising an active agent that is disulfiram and a second composition comprising a potentiating ingredient that is TBHQ.

The present disclosure provides methods that comprise administering a therapeutically effective amount of an active agent that is disulfiram and a potentiating ingredient that is TBHQ, contacting a cell or immune cell with an active agent that is disulfiram and a potentiating ingredient that is TBHQ, a composition comprising an active agent that is disulfiram and a potentiating ingredient that is TBHQ, and a plurality of compositions comprising a first composition comprising an active agent that is disulfiram and a second composition comprising a potentiating ingredient that is TBHQ.

A potentiating ingredient, i.e., TBHQ, enhances, increases, and/or improves the desirable activity of the active ingredient, i.e., disulfiram. As a non-limiting example, the potentiating ingredient enhances pyroptosis activity of disulfiram.

The potentiating ingredient, i.e., TBHQ, used in the present disclosure enhances, increases, and/or improves the effectiveness and/or desirable activity of the active ingredient, i.e., disulfiram. Thus, a composition comprising disulfiram alone will be less effective, for example, than a composition comprising disulfiram and its potentiating ingredient TBHQ. Similarly, a method in which disulfiram is administered alone is less effective than a method in which disulfiram is administered with TBHQ (either as a single composition or as distinct compositions that are administered contemporaneously or sequentially). In various embodiments, the potentiating ingredient, as disclosed herein, enhances disulfiram's ability to inhibit pyroptosis. In some embodiments, the enhanced, increased, and/or improved effectiveness and/or activity of the active agent, i.e., disulfiram, may be any amount between about 1.1-fold and about 3-fold, e.g., about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, or 3-fold, and any fold therebetween. In embodiments, the enhanced, increased, and/or improved effectiveness and/or activity of the active agent, i.e., disulfiram, may be any amount between about 3-fold and about 5-fold, e.g., about 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5-fold, and any fold therebetween. The enhanced, increased, and/or improved effectiveness and/or activity of the active agent, i.e., disulfiram, may be any amount between about 5-fold and about 15-fold. As examples, the effectiveness may be increased about 5, 5.5, 6, 6.5, 7, 7.5, 8, 8.5, 9, 9.5, 10, 10.5, 11, 11.5, 12, 12.5, 13, 13.5, 14, 14.5, or 15-fold, and any fold therebetween. In some embodiments, the enhanced, increased and/or improved effectiveness and/or activity of the active agent, i.e., disulfiram, is greater than about 15-fold. The increased and/or improved effectiveness may be greater than about 1%, e.g., about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or about 100%, and any percentage therebetween.

An enhanced, increased, and/or improved effectiveness and/or activity of the active agent, i.e., disulfiram, may be determined by any assay, phenotype, marker, or indicator demonstrating a desired outcome from a treatment or administration of a composition. As examples, effectiveness and/or activity may be shown as a reduction in markers/indicators of an aging cell, an increase in markers/indicators of a healthy cell, an extension of the active life of a cell, a reduction in apoptosis, increased longevity of a mammal, a reduction in the predicted biological age of a cell, increased titer of antibodies in response to a vaccine, inhibition of pyroptosis in an in vitro assay, an immune profile, and phenotypic changes in a cell that report health and/or activity. Increased and/or improved effectiveness may be objective (e.g., quantifiable) or subjective (e.g., qualifiable).

Because the potentiating ingredient, i.e., TBHQ, enhances, increases, and/or improve disulfiram's effectiveness and/or activity (e.g., in pyroptosis inhibition), lower doses of disulfiram may be administered to a mammal while still providing a desired outcome. This lower dose may minimize adverse effects resulting from disulfiram administration.

In certain embodiments, disulfiram is administered at a daily dosage of about 5 mg to about 500 mg per day. For example, disulfiram is administered at a total daily dosage of about 5, 6, 7, 8, 9, 10, 15, 20, 25, 30, 45, 40, 45, 50, 55, 60, 65, 70, 75, 80, 85, 90, 95, 100, 125, 150, 175, 200, 225, 250, 275, 300, 325, 350, 375, 400, 425, 450, 475, or 500 mg per day, and any total dosage therebetween. As examples, the daily dosage may be 5-10 mg, 10-15 mg, 15-20 mg, 20-25 mg, 25-30 mg, 30-35 mg, 35-40 mg, 40-45 mg, 45-50 mg, 50-55 mg, 55-60 mg, 60-65 mg, 65-70 mg, 70-75 mg, 75-80 mg, 80-85 mg, 85-90 mg, 90-95 mg, 95-100 mg, 100-125 mg, 125-150 mg, 150-175 mg, 175-200 mg, 200-225 mg, 225-250 mg, 250-275 mg, 275-300 mg, 300-325 mg, 325-350 mg, 350-375 mg, 375-400 mg, 400-425 mg, 425-450 mg, 450-475 mg, or 475-500 mg. The disulfiram may be administered 1×, 2×, or 3× per day to achieve the daily dosage. Thus, for a daily dose of 5 mg with a once per day administration, only a single administration of 5 mg will be given; for a daily dose of 5 mg with a twice per day administration, two administrations of about 2.5 mg will be given; and for a daily dose of 5 mg with a thrice per day administration, three administrations of about 1.7 mg will be given. Similarly, for a daily dose of 500 mg with a once per day administration, only a single administration of 500 mg will be given; for a daily dose of 500 mg with a twice per day administration, two administrations of about 250 mg will be given; and for a daily dose of 500 mg with a thrice per day administration, three administrations of about 170 mg will be given. The potentiating ingredient, i.e., TBHQ, may be administered 1×, 2×, or 3× per day.

In certain embodiments, the potentiating ingredient, i.e., TBHQ, and the disulfiram are administered in two separate formulations. In certain embodiments, the TBHQ and the disulfiram are administered in a single formulation.

In certain embodiments, the potentiating ingredient, i.e., TBHQ, is administered at a ratio of about 1:1 to about 1:3000 moles of TBHQ to disulfiram. The TBHQ may be administered at a ratio of about 1:1, 1:1.01, 1:1.02, 1:1.03, 1:1.04, 1:1.05, 1:1.06, 1:1.07, 1:1.08, 1:1.09, 1:1.1, 1:1.11, 1:1.12, 1:1.13, 1:1.14, 1:1.15, 1:1.16, 1:1.17, 1:1.18, 1:1.19, 1:1.2, 1:1.21, 1:1.22, 1:1.23, 1:1.24, 1:1.25, 1:1.26, 1:1.27, 1:1.28, 1:1.29, or 1:1.3 moles TBHQ per mole of disulfiram. The TBHQ may be administered at a ratio of about 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20 moles TBHQ per mole of disulfiram. The TBHQ may be administered at a ratio of about 1:10, 1:20, 1:30, 1:40, 1:50, 1:60, 1:70, 1:80, 1:90, 1:100, 1:110, 1:120, 1:130, 1:140, 1:150, 1:160, 1:170, 1:180, 1:190, or 1:200 moles TBHQ per mole of disulfiram, and any ratio therebetween. As examples, the ratio may be about 1:10-1:15, 1:15-1:20, 1:20-1:25, 1:25-1:30, 1:30-1:35, 1:35-1:40, 1:40-1:45, 1:45-1:50, 1:50-1:55, 1:55-1:60, 1:60-1:65, 1:65-1:70, 1:70-1:75, 1:75-1:80, 1:80-1:85, 1:85-1:90, 1:90-1:95, 1:95-1:100, 1:100-1:125, 1:125-1:150, 1:150-1:175, 1:175-1:200 moles TBHQ per mole of disulfiram. The TBHQ may be administered at a ratio of about 1:100, 1:200, 1:300, 1:400, 1:500, 1:600, 1:700, 1:800, 1:900, or 1:1000 moles TBHQ per mole of disulfiram, and any ratio therebetween. As examples, the ratio may be about 1:100-1:125, 1:125-1:150, 1:150-1:175, 1:175-1:200, 1:200-1:225, 1:225-1:250, 1:250-1:275, 1:275-1:300, 1:300-1:325, 1:325-1:350, 1:350-1:375, 1:375-1:400, 1:400-1:425, 1:425-1:450, 1:450-1:475, 1:475-1:500, 1:500-1:525, 1:525-1:550, 1:550-1:575, 1:575-1:600, 1:600-1:625, 1:625-1:650, 1:650-1:675, 1:675-1:700, 1:700-1:725, 1:725-1:750, 1:750-1:775, 1:775-1:800, 1:800-1:825, 1:825-1:850, 1:850-1:875, 1:875-1:900, 1:900-1:925, 1:925-1:950, 1:950-1:975, or 1:975-1:1000 moles TBHQ per mole of disulfiram. The TBHQ may be administered at a ratio of about 1:1000, 1:1100, 1:1200, 1:1300, 1:1400, 1:1500, 1:1600, 1:1700, 1:1800, 1:1900, 1:2000, 1:2100, 1:2200, 1:2300, 1:2400, 1:2500, 1:2600, 1:2700, 1:2800, 1:2900, or 1:3000 moles TBHQ per mole of disulfiram, and any ratio therebetween. As examples, the ratio may be about 1:1000-1:1100, 1:1100-1:1200, 1:1200-1:1300, 1:1300-1:1400, 1:1400-1:1500, 1:1500-1:1600, 1:1600-1:1700, 1:1700-1:1800, 1:1800-1:1900, 1:1900-1:2000, 1:2000-1:2100, 1:2100-1:2200, 1:2200-1:2300, 1:2300-1:2400, 1:2400-1:2500, 1:2500-1:2600, 1:2600-1:2700, 1:2700-1:2800, 1:2800-1:2900, or 1:2900-1:3000 moles TBHQ per mole of disulfiram.

In embodiments where the potentiating ingredient, i.e., TBHQ, and the active agent, i.e., disulfiram, are administered in a single formulation, the amount of TBHQ is about 0.02% to about 56% of the amount of disulfiram (by weight). The amount of TBHQ may be about 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.3%, 0.4%, 0.5%, 0.6%, 0.7%, 0.8%, 0.9%, or 1% of the weight of the disulfiram. The amount of TBHQ may be about 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8%, 10%, of the weight of the disulfiram, and any percentage therebetween. As examples, the percentage may be about 1%-1.5%, 1.5%-2%, 2%-2.5%, 2.5%-3%, 3%-3.5%, 3.5%-4%, 4%-4.5%, 4.5%-5%, 5%-5.5%, 5.5%-6%, 6%-6.5%, 6.5%-7%, 7%-7.5%, 7.5%-8%, 8%-8.5%, 8.5%-9%, 9%-9.5%, or 9.5%-10% of the weight of the disulfiram. The amount of TBHQ may be about 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, or 56% of the weight of the disulfiram, and any percentage therebetween. As examples, the percentage may be about 10%-15%, 15%-20%, 20%-25%, 25%-30%, 30%-35%, 35%-40%, 40%-45%, 45%-50%, or 50%-56% of the weight of the disulfiram. In embodiments where the potentiating ingredient, i.e., TBHQ, and the active agent, i.e., disulfiram, are administered in two formulations, the amount of TBHQ is about 0.02% to about 56% of the weight of the disulfiram. The amount of TBHQ may be about 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.3%, 0.4%, 0.5%, 0.6%, 0.7%, 0.8%, 0.9%, or 1% of the weight of the disulfiram. The amount of TBHQ may be about 1%, 1.2%, 1.4%, 1.6%, 1.8%, 2%, 2.2%, 2.4%, 2.6%, 2.8%, 3%, 3.2%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8%, 10%, of the weight of the disulfiram, and any percentage therebetween. As examples, the percentage may be about 1%-1.5%, 1.5%-2%, 2%-2.5%, 2.5%-3%, 3%-3.5%, 3.5%-4%, 4%-4.5%, 4.5%-5%, 5%-5.5%, 5.5%-6%, 6%-6.5%, 6.5%-7%, 7%-7.5%, 7.5%-8%, 8%-8.5%, 8.5%-9%, 9%-9.5%, or 9.5%-10% of the weight of the disulfiram. The amount of TBHQ may be about 10%, 12%, 14%, 16%, 18%, 20%, 22%, 24%, 26%, 28%, 30%, 32%, 34%, 36%, 38%, 40%, 42%, 44%, 46%, 48%, 50%, 52%, 54%, or 56% of the weight of the disulfiram, and any percentage therebetween. As examples, the percentage may be about 10%-15%, 15%-20%, 20%-25%, 25%-30%, 30%-35%, 35%-40%, 40%-45%, 45%-50%, or 50%-56% of the weight of the disulfiram.

In some embodiments, TBHQ is administered at a daily dosage from about 0.001 mg to about 280 mg. As examples, TBHQ is administered at a total daily dosage of about 0.001 mg, 0.002 mg, 0.003 mg, 0.004 mg, 0.005 mg, 0.006 mg, 0.007 mg, 0.008 mg, 0.009 mg, or 0.01 mg, and any daily dosage therebetween. As examples, the daily dosage of TBHQ may be about 0.001-0.002 mg, 0.002-0.003 mg, 0.003-0.004 mg, 0.004-0.005 mg, 0.005-0.006 mg, 0.006-0.007 mg, 0.007-0.008 mg, 0.008-0.009 mg, or 0.009-0.01 mg. The TBHQ may be administered at a total daily dosage of about 0.01 mg, 0.02 mg, 0.03 mg, 0.04 mg, 0.05 mg, 0.06 mg, 0.07 mg, 0.08 mg, 0.09 mg, or 0.1 mg, and any daily dosage therebetween. As examples, the daily dosage of TBHQ may be about 0.01-0.02 mg, 0.02-0.03 mg, 0.03-0.04 mg, 0.04-0.05 mg, 0.05-0.06 mg, 0.06-0.07 mg, 0.07-0.08 mg, 0.08-0.09 mg, or 0.09-0.1 mg. The TBHQ may be administered at a total daily dosage of about 0.1 mg, 0.2 mg, 0.3 mg, 0.4 mg, 0.5 mg, 0.6 mg, 0.7 mg, 0.8 mg, 0.9 mg, or 1 mg, and any daily dosage therebetween. As examples, the daily dosage of TBHQ may be about 0.1-0.2 mg, 0.2-0.3 mg, 0.3-0.4 mg, 0.4-0.5 mg, 0.5-0.6 mg, 0.6-0.7 mg, 0.7-0.8 mg, 0.8-0.9 mg, or 0.9-1 mg. The TBHQ may be administered at a total daily dosage of about 1 mg, 2 mg, 3 mg, 4 mg, 5 mg, 6 mg, 7 mg, 8 mg, 9 mg, or 10 mg, and any daily dosage therebetween. As examples, the daily dosage of TBHQ may be about 1-2 mg, 2-3 mg, 3-4 mg, 4-5 mg, 5-6 mg, 6-7 mg, 7-8 mg, 8-9 mg, or 9-10 mg. The TBHQ may be administered at a total daily dosage of about 10 mg, 20 mg, 30 mg, 40 mg, 50 mg, 60 mg, 70 mg, 80 mg, 90 mg, or 100 mg, and any daily dosage therebetween. As examples, the daily dosage of TBHQ may be about 10-20 mg, 20-30 mg, 30-40 mg, 40-50 mg, 50-60 mg, 60-70 mg, 70-80 mg, 80-90 mg, or 90-100 mg. The TBHQ may be administered at a total daily dosage of about 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, or 280 mg and any daily dosage therebetween. As examples, the daily dosage of TBHQ may be about 100-110 mg, 110-120 mg, 120-130 mg, 130-140 mg, 140-150 mg, 150-160 mg, 160-170 mg, 170-180 mg, 180-190 mg, 190-200 mg, 200-210 mg, 210-220 mg, 220-230 mg, 230-240 mg, 240-250 mg, 250-260 mg, 260-270 mg, or 270-280 mg. The potentiating ingredient, i.e., TBHQ, may be administered 1×, 2×, or 3× per day to achieve the daily dosage. Thus, for a daily dose of 5 mg with a once per day administration, only a single administration of 5 mg will be given; for a daily dose of 5 mg with a twice per day administration, two administrations of about 2.5 mg will be given; and for a daily dose of 5 mg with a thrice per day administration, three administrations of about 1.7 mg will be given. Similarly, for a daily dose of 280 mg with a once per day administration, only a single administration of 280 mg will be given; for a daily dose of 280 mg with a twice per day administration, two administrations of about 140 mg will be given; and for a daily dose of 280 mg with a thrice per day administration, three administrations of about 93 mg will be given.

Compositions and methods of the present disclosure may further comprise one or more additional ingredients. The additional ingredients may also potentiate the activity of the active agent, i.e., disulfiram. As such, the additional ingredient may be considered a second potentiating ingredient. The additional ingredient may also assist in the potentiating activity of TBHQ. The additional ingredient may be generally activity inert and, instead, provide other favorable properties to a composition, e.g., acting as a binder, a buffer, a solute, an excipient, and so forth. For example, a composition of the present disclosure may comprise disulfiram and TBHQ and one or more additional ingredients. When a plurality of compositions is useful in the present disclosure, a first composition may comprise disulfiram, a second composition may comprise TBHQ, and an at least third composition may comprise one or more additional ingredients. For methods of the present disclosure, a subject may be administered a composition comprising disulfiram, TBHQ, and one or more additional potentiating ingredients. For other methods of the present disclosure, a subject may be administered a first composition comprising disulfiram, a second composition comprising TBHQ, and an at least third composition comprising one or more additional ingredients.

An additional ingredient, as used herein, is a compound that is generally recognized as safe (GRAS; e.g., by the FDA), is listed in the FDA inactive ingredient database (IID (see, the World Wide Web at accessdata.fda.gov/scripts/cder/iig/index.cfm), and/or is included in the FDA's Substances Added to Food list (see, the World Wide Web at cfsanappsexternal.fda.gov/scripts/fdcc/?set=FoodSubstances and the regulations set forth in 21 CFR 73, 74, 172, 173, 181, 182, and 184, the contents of each of which is incorporated by reference in its entirety). An additional ingredient may be found in a plurality of the above-mentioned lists/databases. In some instances, an additional ingredient is considered an "inactive ingredient". An inactive ingredient is any component of a drug product other than the active ingredient (see, the World Wide Web at fda.gov/drugs/drug-approvals-and-databases/inactive-ingredients-approved-drug-products-search-frequently-asked-questions, the contents of which is incorporated by reference in its entirety). In the present disclosure, the active ingredient is disulfiram. In various embodiments of the present disclosure, an additional ingredient is any substance that can intentionally be added to a food as a food additive and which is generally recognized, among qualified experts, as having been adequately shown to be safe under the conditions of its intended use. In particular, additional ingredients are exempted from the usual Federal Food, Drug, and Cosmetic Act (FFDCA) food additive tolerance requirements. An additional ingredient, as used herein, includes both the specific additional ingredient and any of its metabolites and/or their derivatives. Non-limiting examples of a metabolite includes a salt and ester of the additional ingredient. Other variations may include changes in Chirality, Isomers, Hydration states relative to the specific additional ingredient. The usefulness of a metabolite or a derivative of an additional ingredient that is useful in the present disclosure, is well-within the ability of a skilled artisan; such experiments needed to verify that the metabolite or derivative is useful would be similar to the experiments used to verify that the specific additional ingredient is useful, e.g., in the compositions and methods of the present disclosure.

TABLE 1

| Catalog No | Drug Names | Target | Pathway | Biological Activity | CAS |
|---|---|---|---|---|---|
| HY-101036 | Choline (bitartrate) | mAChR | GPCR/G Protein; Neuronal Signaling | Choline (bitartrate) is an essential nutrient, often associated with the B vitamins but not yet officially defined as a B vitamin. Choline (bitartrate) plays an important role in synthesis of the neurotransmitter acetylcholine. | 87-67-2 |
| HY-101103 | (2-Hydroxypropyl)-β-cyclodextrin | Others | Others | (2-Hydroxypropyl)-β-cyclodextrin is a widely used drug delivery vehicle to improve the stability and bioavailability. | 128446-35-5 |
| HY-101530 | Polyoxyethylene stearate | Others | Others | Polyoxyethylene stearate (POES) is a non-ionic emulsifying agent. | 9004-99-3 |
| HY-10448 | Capsaicin | Bacterial; P-glycoprotein | Anti-infection; Membrane Transporter/Ion Channel | Capsaicin ((E)-Capsaicin) is a mixture of Capsaicin and Dihydrocapsaicin. Capsaici is a TRPV1 agonist with an EC50 of 0.29 μM in HEK293 cells. | 404-86-4 |
| HY-107201 | β-Cyclodextrin | Autophagy; TRP Channel | Autophagy; Membrane Transporter/Ion Channel; Neuronal Signaling | β-Cyclodextrin is a cyclic polysaccharide composed of seven units of glucose (α-D-glucopyranose) linked by α-(1,4) type bonds. β-Cyclodextrin has often been used to enhance the solubility of drugs. β-Cyclodextrin has anti-influenza virus H1N1 activities. | 7585-39-9 |
| HY-107799 | Castor oil | Influenza Virus | Anti-infection | Castor oil is a natural triglyceride and a solvent. Castor oil has a laxative effect and induces labor in pregnant females. Castor oil can be used as a solvent, co-solvent, stabilizing agent and polyol for the formation of polymer-nanoparticle composites. | 8001-79-4 |
| HY-107832 | Ketoisophorone | Others | Others | Ketoisophorone (4-Oxoisophorone) is a key intermediate in the synthesis of carotenoids and flavouring agents. Ketoisophorone is an industrially important cyclic endione. | 1125-21-9 |
| HY-107846 | Xylan | Others | Others | Xylan represents the main hemicellulose component in the secondary plant cell walls of flowering plants. Xylan is a polysaccharide made from units of xylose and contains predominantly β-D-xylose units linked as in cellulose. | 9014-63-5 |
| HY-109521 | Manganous chloride tetrahydrate | Others | Others | | |
| HY-111095 | D-(−)-Lactic acid | Endogenous Metabolite | Metabolic Enzyme/Protease | D-(−)-Lactic acid is a normal intermediate in the fermentation (oxidation, metabolism) of sugar. D-(−)-Lactic acid is identified to be a competitive inhibitor of ProDH (proline dehydrogenase) in plants. | 10326-41-7 |
| HY-111830 | Lignin | Others | Others | Lignin (Ligninе) is a natural complex biopolymer with biodegradable and biocompatible. Lignin is the main component of plant cell walls and is a renewable aromatic polymer. Lignin has strongly antioxidant activity. | 9005-53-2 |
| HY-112624 | Dextran | Others | Others | Dextran (Dextran 40) has an inhibitory effect on thrombocyte aggregation and coagulation factors and is used as a plasma volume expander. | 9004-54-0 |
| HY-113063 | 3-Methyl-2-oxovaleric acid | Endogenous Metabolite | Metabolic Enzyme/Protease | 3-Methyl-2-oxovaleric acid is a neurotoxin, an acidogen, and a metabotoxin, and also an abnormal metabolite that arises from the incomplete breakdown of branched-chain amino acids. | 1460-34-0 |

TABLE 1-continued

Illustrative additional ingredients

| Catalog No | Drug Names | Target | Pathway | Biological Activity | CAS |
|---|---|---|---|---|---|
| HY-114336 | Enocyanin | Phosphatase | Metabolic Enzyme/Protease | Enocyanin is an anthocyanin extracted from grapes. Enocyanin shows inhibitory effect on the leucine aminopeptidase, acid phosphatase, γ-glutamyl transpeptidase and esterase activity. | 11029-12-2 |
| HY-116084 | Trimethylamine N-oxide | Endogenous Metabolite; NOD-like Receptor (NLR); Reactive Oxygen Species; TGF-beta/Smad | Immunology/Inflammation; Metabolic Enzyme/Protease; NF-κB; Stem Cell/Wnt; TGF-beta/Smad | Trimethylamine N-oxide is a gut microbe-dependent metabolite of dietary choline and other trimethylamine-containing nutrients. Trimethylamine N-oxide induces inflammation by activating the ROS/NLRP3 inflammasome. Trimethylamine N-oxide also accelerates fibroblast-myofibroblast differentiation and induces cardiac fibrosis by activating the TGF-β/smad2 signaling pathway. | 1184-78-7 |
| HY-119309 | Sucrose octaacetate | Others | Others | Sucrose octaacetate is an acetylated derivative of sucrose with an intensely bitter tasting and can be used as bitter tasting surrogate. Sucrose octaacetate can be used as food additive and also used as an adhesive and plasticizer. Sucrose octaacetate also used in many pesticides, insecticides, and other toxic products as a deterrent to accidental poisoning. Sucrose octaacetate can also be used as an in situ seed and a soft template to synthesize polyaniline (PANI) nanofibers. | 126-14-7 |
| HY-124190 | Isopropyl myristate | | | | 110-27-0 |
| HY-125861 | Methyl cellulose | Others | Others | Methylcellulose is a natural polymer which gels on heating. Methylcellulose is not toxic. | 9004-67-5 |
| HY-125865 | Casein | | | | 9000-71-9 |
| HY-128454 | Dimethyl trisulfide | Endogenous Metabolite | Metabolic Enzyme/Protease | Dimethyl trisulfide is an organic chemical compound and the simplest organic trisulfide found in garlic, onion, broccoli, and similar plants. Dimethyl trisulfide is a cyanide antidote. | 3658-80-8 |
| HY-13211 | (E)-2-Decenoic acid | Others | Others | (E)-2-Decenoic acid is an interesting fatty acid isolated from royal jelly secretions of honey bees. | 334-49-6 |
| HY-14608 | (S)-Glutamic acid | Apoptosis; Endogenous Metabolite; Ferroptosis; iGluR | Apoptosis; Membrane Transporter/Ion Channel; Metabolic Enzyme/Protease; Neuronal Signaling | (S)-Glutamic acid acts as an excitatory transmitter and an agonist at all subtypes of glutamate receptors (metabotropic, kainate, NMDA, and AMPA). (S)-Glutamic acid shows a direct activating effect on the release of DA from dopaminergic terminals. | 56-86-0 |
| HY-14608A | L-Glutamic acid monosodium salt | Apoptosis; Ferroptosis; iGluR | Apoptosis; Membrane Transporter/Ion Channel; Neuronal Signaling | L-Glutamic acid monosodium salt acts as an excitatory transmitter and an agonist at all subtypes of glutamate receptors (metabotropic, kainate, NMDA, and AMPA). (S)-Glutamic acid shows a direct activating effect on the release of DA from dopaminergic terminals. | 142-47-2 |
| HY-14617 | Paradol | COX | Immunology/Inflammation | Paradol is a pungent phenolic substance found in ginger and other Zingiberaceae plants. Paradol is an effective inhibitor of tumor promotion in mouse skin carcinogenesis, binds to cyclooxygenase (COX)-2 active site. | 27113-22-0 |

TABLE 1-continued

Illustrative additional ingredients

| Catalog No | Drug Names | Target | Pathway | Biological Activity | CAS |
|---|---|---|---|---|---|
| HY-14621 | Zingerone | NF-κB | NF-κB | Zingerone (Vanillylacetone) is a nontoxic methoxyphenol isolated from Zingiber officinale, with potent anti-inflammatory, antidiabetic, antilipolytic, antidiarrhoeic, antispasmodic and anti-tumor properties. Zingerone alleviates oxidative stress and inflammation, down-regulates NF-κB mediated signaling pathways. Zingerone acts as an anti-mitotic agent, and inhibits the growth of neuroblastoma cells. | 122-48-5 |
| HY-15337 | Hesperidin | Autophagy; Endogenous Metabolite; Reactive Oxygen Species | Autophagy; Immunology/Inflammation; Metabolic Enzyme/Protease; NF-κB | Hesperidin (HP) is a bioflavonoid that plays a role in plant defense and is abundant in citrus species, such as grapefruit, lemon and orange. Hesperidin is used effectively as a supplemental agent in complementary therapy protocols, since it possesses biological and pharmacological properties as an effective antioxidant, anti-inflammatory, anti-carcinogenic, and anti-hypertensive agent with lipid-lowering activity in vitro: hesperidin and linarin are two of the main constituent of Valeriana's extract exhibiting a high affinity to KATP channel, which are related to the control of Ca++ concentration and release of GABA in synaptic nerve terminal, mainly on cells of SN in vivo: Hesperidin was dissolved in 1% carboxymethyl cellulose (CMC) and administered orally at a dose of 50 mg/kg for 10 consecutive days. In the control group, rats were treated with the corn oil and 1% CMC vehicle. IC50: hesperidin (IC50 = 116.68 μmo/L)) | 520-26-3 |
| HY-15398 | Cholecalciferol | Endogenous Metabolite; VD/VDR | Metabolic Enzyme/Protease; Vitamin D Related | Cholecalciferol(Vitamin D3) is a naturally occuring form of vitamin D; Reported that upon metabolic activation, Cholecalciferol induces cell differentiation and prevents proliferation of cancer cells. IC50 value: Target: Vitamin D acts through a receptor that is a member of the ligand-dependent transcription factor superfamily. Modulates the proliferation and differentiation of both normal and cancer cells. Has antiproliferative and antimetastatic effects on breast, colon, and prostate cancer cells. Activated vitamin D receptors in intestine and bone maintain calcium absorbance and homeostasis. | 67-97-0 |
| HY-16637 | Folic acid | DNA/RNA Synthesis; Endogenous Metabolite | Cell Cycle/DNA Damage; Metabolic Enzyme/Protease | Folic acid(Vitamin M; Vitamin B9) is a B vitamin; is necessary for the production and maintenance of new cells, for DNA synthesis and RNA synthesis. | 59-30-3 |
| HY-17568 | Nonivamide | TRP Channel | Membrane Transporter/Ion Channel; Neuronal Signaling | Nonivamide is a <b<TRPV1 agonist, which exhibits 4d-EC50 value of 5.1 mg/L in static toxicity tests. | 2444-46-4 |
| HY-22167 | Methyl 2-hydroxy-4-methylvalemte | Others | Others | Methyl 2-hydroxy-4-methylvalemte is one of dominant volatile compounds in Zhenjiang aromatic vinegar. Methyl 2-hydroxy-4-methylvalemte is used for charting flavour biosynthesis networks of vinegar microbiota. | 40348-72-9 |
| HY-23539 | Sodium thiosulfate (pentahydrate) | | | | |
| HY-33518 | 2-Pyridinemethanethiol | | | | |

TABLE 1-continued

Illustrative additional ingredients

| Catalog No | Drug Names | Target | Pathway | Biological Activity | CAS |
|---|---|---|---|---|---|
| HY-34439 | 2,5-Dimethylpyrazine | Endogenous Metabolite | Metabolic Enzyme/Protease | 2,5-Dimethylpyrazine is an endogenous metabolite. | 123-32-0 |
| HY-34465 | 5-Methyl-2-thiophenecarboxaldehyde | Others | Others | 5-Methyl-2-thiophenecarboxaldehyde acts as a candidate to microscopic third order non-linear optical (NLO) material. | 13679-70-4 |
| HY-34544 | 2-Hexylthiophene | | | | 18794-77-9 |
| HY-34751 | 2-Thiophenemethanol | | | | 636-72-6 |
| HY-40135 | L-Hydroxyproline | Endogenous Metabolite | Metabolic Enzyme/Protease | L-Hydroxyproline, one of the hydroxyproline (Hyp) isomers, is a useful chiral building block in the production of many pharmaceuticals. | 51-35-4 |
| HY-41417 | Octanoic acid | Endogenous Metabolite | Metabolic Enzyme/Protease | Octanoic acid is an oily liquid with a slightly unpleasant rancid taste and used commercially in the production of esters used in perfumery and also in the manufacture of dyes. | 124-07-2 |
| HY-41587 | Peracetylated D-glucose | | | | 83-87-4 |
| HY-42680 | (3S,4S,5R)-1,3,4,5,6-Pentahydroxyhexan-2-one | Endogenous Metabolite | Metabolic Enzyme/Protease | (3S,4S,5R)-1,3,4,5,6-Pentahydroxyhexan-2-one is an endogenous metabolite. | 87-81-0 |
| HY-75161 | (-)-Menthol | Endogenous Metabolite; TRP Channel | Membrane Transporter/Ion Channel; Metabolic Enzyme/Protease; Neuronal Signaling | (-)-Menthol is a key component of peppermint oil that binds and activates transient receptor potential melastatin 8 (TRPM8), a Ca2+-permeable nonselective cation channel, to increase [Ca2+]i. Antitumor activity. | 2216-51-5 |
| HY-76063 | Methyl phenylacetate | | | | 101-41-7 |
| HY-76225 | Monoammonium glycyrrhizinate hydrate | Others | Others | Monoammonium glycyrrhizinate hydrate has various pharmacological actions such as anti-inflammatory, antiallergic, antigastriculcer, and antihepatitis activities. | 53956-04-0 |
| HY-76542 | Vitamin D2 | Endogenous Metabolite; VD/VDR | Metabolic Enzyme/Protease; Vitamin D Related | Vitamin D2 (Ergocalciferol) is a form of vitamin D, used as a vitamin D supplement.<br>Target:<br>Ergocalciferol is a secosteroid formed by a photochemical bond breaking of a steroid, specifically, by the action of ultraviolet light on ergosterol. | 50-14-6 |
| HY-77342 | Methyl anthranilate | | | | 134-20-3 |
| HY-77813 | Benzyl isothiocyanate | Antibiotic; Apoptosis; Bacterial | Anti-infection; Apoptosis | Benzyl isothiocyanate is a member of natural isothiocyanates with antimicrobial activity. Benzyl isothiocyanate potent inhibits cell mobility, migration and invasion nature and matrix metalloproteinase-2 (MMP-2) activity of murine melanoma cells. | 622-78-6 |
| HY-77995 | o-Anisaldehyde | | | | 135-02-4 |
| HY-79369 | Succinic anhydride | | | | 108-30-5 |
| HY-A0100 | Thiamine monochloride | Others | Others | Thiamine monochloride (Vitamin B1) is an essential vitamin that plays an important role in cellular production of energy from ingested food and enhances normal neuronal actives. | 59-43-8 |

TABLE 1-continued

Illustrative additional ingredients

| Catalog No | Drug Names | Target | Pathway | Biological Activity | CAS |
|---|---|---|---|---|---|
| HY-A0104 | Hypromellose | Others | Others | Hypromellose is a water-soluble hydrophilic, non-ionic cellulose ether used to form swellable-soluble matrices. | 9004-65-3 |
| HY-B0133 | Natamycin | Antibiotic; Endogenous Metabolite; Fungal | Anti-infection; Metabolic Enzyme/Protease | Natamycin (pimaricin) is an antifungal macrolide polyene that binds to cell membrane sterols.<br>Target: Antifungal<br>Natamycin (INN), also known as pimaricin and sometimes sold as Natacyn, is a naturally occurring antifungal agent produced during fermentation by the bacterium Streptomyces natalensis, commonly found in soil Natamycin has a very low solubility in water; however, natamycin is effective at very low levels. There is an MIC (minimum inhibitory concentration) of less than 10 ppm for most molds. Natamycin is classified as a macrolide polyene antifungal and, as a drug, is used to treat fungal keratitis. It is especially effective against Aspergillus and Fusarium corneal infections. Other common members of the polyene macrolide antifungal family are amphotericin B, nystatin, and filipin. Natamycin is also used in the food industry as a natural preservative. Natamycin is used to treat fungal infections, including Candida, Aspergillus, Cephalosporium, Fusarium and Penicillium. It is applied as a cream, in eyedrops, or (for oral infections) in a lozenge. Natamycin shows negligible absorption into the body when administered in these ways. When taken orally, little or none is absorbed from the gastrointestinal tract, making it inappropriate for systemic infections. | 7681-93-8 |
| HY-B0143 | Niacin | Autophagy; Endogenous Metabolite | Autophagy; Metabolic Enzyme/Protease | Niacin (Vitamin B3) is a water-soluble vitamin and is part of the vitamin B group.<br>Target: Others<br>Niacin (also known as vitamin B3 and nicotinic acid) is an organic compound with the formula C6H5NO2 and, depending on the definition used, one of the 20 to 80 essential human nutrients. Not enough niacin in the diet can cause nausea, skin and mouth lesions, anemia, headaches, and tiredness. Chronic Niacin deficiency leads to a disease called pellagra. The lack of niacin may also be observed in pandemic deficiency disease which is caused by a lack of five crucial vitamins. niacin,vitamin C, thiamin, vitamin D and vitamin A, and is usually found in areas of widespread poverty and malnutrition.<br>Niacin has been used for over 50 years to increase levels of HDL in the blood and has been found to decrease the risk of cardiovascular events modestly in a number of controlled human trials. Niacin cannot be directly converted to nicotinamide, but both compounds could be converted to and are precursors of NAD and NADP in vivo.Nicotinic acid, nicotinamide, and tryptophan (via quinoline acid) are co-factors for nicotinamide adenine dinucleotide (NAD) and nicotinamide adenine dinucleotide phosphate (NADP). NAD converts to NADP by phosphorylation in the presence of the enzyme NAD + kinase NADP and NAD are coenzyme for many dehydrogenases, participating in many hydrogen transfer processes. NAD is important in catabolism of fat, carbohydrate, protein, and alcohol, as well as cell signaling and DNA repair, and NADP mostly in anabolism reactions such as fatty acid and cholesterol synthesis.High energy requirements (brain) or high turnover rate (gut, skin) organs are usually the most susceptible to their deficiency. | 59-67-6 |

TABLE 1-continued

Illustrative additional ingredients

| Catalog No | Drug Names | Target | Pathway | Biological Activity | CAS |
|---|---|---|---|---|---|
| HY-B0150 | Nicotinamide | Endogenous Metabolite; Sirtuin | Cell Cycle/DNA Damage; Epigenetics; Metabolic Enzyme/Protease | Nicotinamide is a form of vitamin B3 that plays essential roles in cell physiology through facilitating NAD+ redox homeostasis and providing NAD+ as a substrate to a class of enzymes that catalyze non-redox reactions. Nicotinamide is an inhibitor of SIRT1. | 98-92-0 |
| HY-B0166 | L-Ascorbic acid | Apoptosis; Reactive Oxygen Species | Apoptosis; Immunology/Inflammation; Metabolic Enzyme/Protease; NF-κB | L-Ascorbic acid is an effective reducing agent and donor antioxidant. | 50-81-7 |
| HY-B0166A | L-Ascorbic acid sodium salt | Apoptosis; Reactive Oxygen Species | Apoptosis; Immunology/Inflammation; Metabolic Enzyme/Protease; NF-κB | L-Ascorbic acid sodium salt is a more bioavailable form of vitamin C that is an antioxidant agent. | 134-03-2 |
| HY-B0167 | Salicylic acid | Apoptosis; Autophagy; COX; Endogenous Metabolite; Mitophagy | Apoptosis; Autophagy; Immunology/Inflammation; Metabolic Enzyme/Protease | Salicylic acid (2-Hydroxybenzoic acid) inhibits cyclo-oxygenase-2 (COX-2) activity independently of transcription factor (NF-κB) activation. | 69-72-7 |
| HY-B0302 | Etidronic acid | Apoptosis | Apoptosis | Etidronic acid (HEDPA) is a bisphosphonate used in detergents, water treatment, cosmetics and pharmaceutical treatment.<br>Target: Others<br>Etidronic acid (HEDPA) is a chelating agent and may be added to bind to or counter the effects of substances such as iron, or other metal ions that can occur in the presence of some soaps. Etidronic acid also acts to retard oxidation of fatty acids. For clarification, a chelator, or chelating agent is a binding component added to many cosmetics, beauty products, and water softeners to form multiple bonds with a single metal ion and neutralize it. | 2809-21-4 |
| HY-B0314 | Talc | Others | Others | Talc, a naturally occurring mineral composed primarily of magnesium, silicon and oxygen, is used in many cosmetics, from baby powder to blush. | 14807-96-6 |
| HY-B0315 | Vitamin B12 | Endogenous Metabolite | Metabolic Enzyme/Protease | Vitamin B12 is a water soluble vitamin with a key role in the normal functioning of the brain and nervous system, and for the formation of blood. | 68-19-9 |
| HY-B0342 | Meglumine | Others | Others | Meglumine is an amino sugar derived from sorbitol.<br>Target: Others<br>Meglumine is often used as an excipient in pharmaceuticals and in conjunction with iodinated compounds in contrast media such as diatrizoate meglumine and iodipamide meglumine. | 6284-40-8 |
| HY-B0351 | Taurine | Autophagy; Endogenous Metabolite | Autophagy; Metabolic Enzyme/Protease | Taurine is an organic acid widely distributed in animal tissues.<br>Target: Others<br>Taurine is a major constituent of bile and can be found in the large intestine and accounts for approximately 0.1% of total human body weight. Taurine is present in high concentration in algae and in the | 107-35-7 |

TABLE 1-continued

Illustrative additional ingredients

| Catalog No | Drug Names | Target | Pathway | Biological Activity | CAS |
|---|---|---|---|---|---|
| | | | | animals including insects and arthropods, but is generally absent or present in traces in the bacterial and plant kingdoms. In cardiac tissue alone, taurine levels of 20 mM or higher may be found. Taurine availability protects against cholestasis induced by monohydroxy bile acids remains confined to guinea pigs. Oral supplementation of taurine results in increased plasma taurine concentrations and is associated with normalization of left ventricular function in both groups of cats. Myocardial concentrations of taurine are directly related to plasma concentrations and low plasma concentrations are found to be associated with myocardial failure in cats, proposing a direct link occurs between decreased taurine concentration in the myocardium and decreased myocardial mechanical function. | |
| HY-B0361 | Aspartame | Others | Others | Aspartame (SC-18862) is an artificial, non-saccharide sweetener used as a sugar substitute in some foods and beverages. | 22839-47-0 |
| HY-B0389 | Dextrose | Endogenous Metabolite | Metabolic Enzyme/Protease | Dextrose, a simple sugar (monosaccharide), is an important carbohydrate in biology.<br>Target: Others<br>Dextrose(D-glucose), a simple sugar (monosaccharide), is an important carbohydrate in biology. | 50-99-7 |
| HY-B0399 | L-Carnitine | Endogenous Metabolite | Metabolic Enzyme/Protease | L-carnitine (Levocarnitine) is constituent of striated muscle and liver. It is used therapeutically to stimulate gastric and pancreatic secretions and in the treatment of hyperlipoproteinemias.<br>Target: Others<br>L-carnitine (Levocarnitine) is an endogenous molecule involved in fatty acid metabolism, biosynthesized within the human body using amino acids: L-lysine and L-methionine, as substrates.<br>L-carnitine (Levocarnitine) can also be found in many foods, but red meats, such as beef and lamb, are the best choices for adding carnitine into the diet. Administering L-carnitine (510 mg/day) to patients with the disease.<br>L-carnitine (Levocarnitine) treatment significantly improved the total time for dozing off during the daytime, calculated from the sleep logs, compared with that of placebo-treated periods.<br>L-carnitine (Levocarnitine) efficiently increased serum triglycerides concentration.<br>L-carnitine (Levocarnitine) and its derivatives show promise in the treatment of chronic conditions and diseases associated with mitochondrial dysfunction but further translational studies are needed to fully explore their potential. | 541-15-1 |
| HY-B0400 | D-Sorbitol | Endogenous Metabolite | Metabolic Enzyme/Protease | D-Sorbitol is a sugar alcohol that is commonly used as a sugar substitute.<br>Target: Others<br>D-Sorbitol occurs naturally and is also produced synthetically from glucose. The food industry uses D-sorbitol as an additive in the form of a sweetener, humectant, emulsifier, thickener, or dietary supplement. D-Sorbitol has also been found in cosmetics, paper, and pharmaceuticals. Naturally, D-sorbitol occurs widely in plants via photosynthesis, ranging from algae to higher order fruits of the family Rosaceae. From Wikipedia. | 50-70-4 |
| HY-B0430A | D-Pantothenic acid (sodium) | Apoptosis | Apoptosis | D-Pantothenic acid sodium (Sodium pantothenate) is an essential trace nutrient that functions as the obligate precursor of coenzyme A (CoA). D- | 867-81-2 |

TABLE 1-continued

Illustrative additional ingredients

| Catalog No | Drug Names | Target | Pathway | Biological Activity | CAS |
|---|---|---|---|---|---|
| HY-B0456 | Riboflavin | Endogenous Metabolite | Metabolic Enzyme/Protease | Pantothenic acid sodium plays key roles in myriad biological processes, including many that regulate carbohydrate, lipid, protein, and nucleic acid metabolism.<br>Riboflavin is an easily absorbed micronutrient with a key role in maintaining health in humans and other animals<br>Target: Others<br>Riboflavin (vitamin B2) is the direct precursor of redox enzyme cofactors flavin mononucleotide (FMN) and flavin adenine dinucleotide (FAD), which are essential for multiple cell physiology. Urinary excretion of riboflavin contributes to one-half of the overall removal of riboflavin from plasma. No sex differences were observed for any of the pharmacokinetic variables (P > 0.05). Riboflavin, similar to other vitamins of the B complex, presents anti-inflammatory activity but its full characterization has not yet been carried out. Riboflavin (25, 50 or 100 mg/kg, i.p.), administered immediately and 2 h after the injection of carrageenan, induced antiedema and antinociceptive effects. The antinociceptive effect was not inhibited by the pretreatment with cadmium sulfate (1 mg/kg), an inhibitor of flavokinase Riboflavin (50 or 100 mg/kg, i.p., 0 and 2 h) also inhibited the fever induced by lipopolysaccharide (LPS) in rats. Riboflavin is a safe drug, is approved for clinical use and exacerbates the antinociceptive effect of morphine, may warrant clinical trials to assess its potential in the treatment of different painful or inflammatory conditions. | 83-88-5 |
| HY-B0511 | Biotin | Others | Others | Biotin is an enzyme co-factor present in minute amounts in every living cell.<br>Target: Others<br>Biotin is necessary for cell growth, the production of fatty acids, and the metabolism of fats and amino acids. It plays a role in the citric acid cycle, which is the process by which biochemical energy is generated during aerobic respiration. Biotin is a coenzyme for carboxylase enzymes, involved in the synthesis of fatty acids, isoleucine, and valine, and in gluconeogenesis. In addition, biotin is widely used throughout the biotechnology industry to conjugate proteins for biochemical assays. The dietary biotin intake in Western populations has been estimated to be 35 to 70 microg/d (143-287 nmol/d). Recent studies suggest that humans absorb biotin nearly completely. Conditions that may increase biotin requirements in humans include pregnancy, lactation, and therapy with anticonvulsants or lipoic acid. | 58-85-5 |
| HY-B0647 | Butylphthalide | Others | Others | Butylphthalide(3-n-Butylphthalide) is an anti-cerebral-ischemia drug; first isolated from the seeds of celery, showed efficacy in animal models of stroke.<br>IC50 value:<br>Target:<br>3-n-butylphthalide alleviates oxidative stress caused by chronic cerebral ischemia, improves cholinergic function, and inhibits amyloid beta accumulation, thereby improving cerebral neuronal injury and cognitive deficits. Intragastric NBP administration to 4-month-old SAMP8 mice for 2 months significantly improved spatial learning and memory ability. Moreover, the loss of choline acetyltransferase (ChAT)-positive neurons | 6066-49-5 |

TABLE 1-continued

Illustrative additional ingredients

| Catalog No | Drug Names | Target | Pathway | Biological Activity | CAS |
|---|---|---|---|---|---|
| | | | | in the medial septal nucleus and the vertical limb of the diagonal band in SAMP8 mice was slowed down, as was the decline in the protein and mRNA expression of ChAT in the hippocampus, cerebral cortex, and forebrain. | |
| HY-B0717 | Tocofersolan | Others | Others | Tocofersolan is a synthetic polyethylene glycol derivative of α-tocopherol. | 9002-96-4 |
| HY-B0892 | Benzyl alcohol | Others | Others | Benzyl alcohol is an aromatic alcohol; a colorless liquid with a mild pleasant aromatic odor. | 100-51-6 |
| HY-B0896 | Triacetin | Endogenous Metabolite; Fungal | Anti-infection; Metabolic Enzyme/Protease | Triacetin is an artificial chemical compound, is the triester of glycerol and acetic acid, and is the second simplest fat after triformin. | 102-76-1 |
| HY-B0914 | 10-Undecenoic acid | Antibiotic; Endogenous Metabolite; Fungal | Anti-infection; Metabolic Enzyme/Protease | 10-Undecenoic acid was used as a starting reagent in the syntheses of Pheromone (11Z)-hexadecenal. | 112-38-9 |
| HY-B0934 | Ethylparaben | Bacterial | Anti-infection | Ethylparaben is the ethyl ester of p-hydroxybenzoic acid, used as an antifungal preservative, and food additive | 120-47-8 |
| HY-B0935 | Benzyl benzoate | Parasite | Anti-infection | Benzyl benzoate is used for treatment of paediatric scabies. | 120-51-4 |
| HY-B0940 | Ethylvanillin | Others | Others | Ethylvanillin is a flavornit, about three times as potent as vanillin and is used in the production of chocolate. | 121-32-4 |
| HY-B0964 | Riboflavin (phosphate sodium) | Endogenous Metabolite | Metabolic Enzyme/Protease | Riboflavin phosphate sodium significantly increases in corneal biomechanical stiffness | 130-40-5 |
| HY-B0985 | Phenazopyridine (hydrochloride) | Others | Others | Phenazopyridine hydrochloride is a chemical, which has a local analgesic effect, often used to alleviate the pain, irritation, discomfort, or urgency caused by urinary tract infections, surgery, or injury to the urinary tract. | 136-40-3 |
| HY-B0987 | Ascorbyl palmitate | Endogenous Metabolite; Reactive Oxygen Species | Immunology/Inflammation; Metabolic Enzyme/Protease; NF-κB | Ascorbyl palmitate is an ester formed from ascorbic acid and palmitic acid creating a fat-soluble form of vitamin C, it is also used as an antioxidant food additive. | 137-66-6 |
| HY-B1008 | 4-Aminobenzoic acid | Endogenous Metabolite | Metabolic Enzyme/Protease | 4-Aminobenzoic acid is an intermediate in the synthesis of folate by bacteria, plants, and fungi. | 150-13-0 |
| HY-B1066 | Butylhydroxyanisole | Ferroptosis; Reactive Oxygen Species | Apoptosis; Immunology/Inflammation; Metabolic Enzyme/Protease; NF-κB | Butylhydroxyanisole is an antioxidant, consisting of a mixture of two isomeric organic compounds, used as a food additive preservative | 25013-16-5 |
| HY-B1092 | Gluconate (Calcium) | Others | Others | Gluconate Calcium (Calcium D-gluconate) is a mineral supplement, manufactured by the neutralization of gluconic acid with lime or calcium carbonate. | 299-28-5 |
| HY-B1092A | Gluconate (sodium) | Endogenous Metabolite | Metabolic Enzyme/Protease | Gluconate sodium (D-Gluconic acid sodium salt) is a corrosion and scale inhibitor of ordinary steel in simulated cooling water. | 527-07-1 |
| HY-B1131 | Taurocholic acid (sodium salt hydrate) | Endogenous Metabolite | Metabolic Enzyme/Protease | Taurocholic acid sodium salt hydrate (Sodium taurocholate hydrate) is a bile acid involved in the emulsification of fats. | 345909-26-4 |

TABLE 1-continued

Illustrative additional ingredients

| Catalog No | Drug Names | Target | Pathway | Biological Activity | CAS |
|---|---|---|---|---|---|
| HY-B1173 | (+)-Camphor | Bacterial | Anti-infection | (+)-Camphor is an ingredient in cooking, and as an embalming fluid for medicinal purposes. | 464-49-3 |
| HY-B1211 | Dehydroacetic acid | Bacterial; Fungal | Anti-infection | Dehydroacetic acid (Biocide 470F), a pyrone derivative acts as an antibacterial and antifungal agent. Dehydroacetic acid possess phytotoxic activity. | 520-45-6 |
| HY-B1263 | Chlorobutanol | Bacterial; Fungal | Anti-infection | Chlorobutanol is a pharmaceutical preservative with sedative-hypnotic actions. Chlorobutanol is active against a wide variety of Gram-positive and Gram-negative bacteria, and several mold spores and fungi. | 57-15-8 |
| HY-B1268 | Docusate (Sodium) | HSV | Anti-infection | Docusate Sodium (Dioctyl sulfosuccinate sodium salt) is a laxative used to for the research of constipation, for constipation due to the use of opiates it may be used with a stimulant laxative, can be taken by mouth or rectally. | 577-11-7 |
| HY-B1278 | D-α-Tocopherol acetate | Endogenous Metabolite | Metabolic Enzyme/Protease | D-α-Tocopherol acetate (D-Vitamin E acetate) can be hydrolyzed to d-alpha-tocopherol (VE) and absorbed in the small intestine. | 58-95-7 |
| HY-B1289 | Cetylpyridinium chloride monohydrate | Bacterial | Anti-infection | Cetylpyridinium chloride monohydrate is a cationic quaternary ammonium compound, used in some types of mouthwashes, toothpastes, throat and nasal sprays, is an antiseptic that kills bacteria and other microorganisms, effective in preventing dental plaque and reducing gingivitis. | 6004-24-6 |
| HY-B1337 | Choline (chloride) | Others | Others | Choline chloride is an organic compound and a quaternary ammonium salt, an acyl group acceptor and choline acetyltransferase substrate, also is an important additive in feed especially for chickens where it accelerates growth. | 67-48-1 |
| HY-B1342 | Vitamin A | Endogenous Metabolite | Metabolic Enzyme/Protease | Retinol, also known as Vitamin A1, has pleiotropic functions including vison, immunity, hematopoiesis, reproduction, cell differentiation/growth, and development. | 68-26-8 |
| HY-B1384 | Retinyl palmitate | Endogenous Metabolite | Metabolic Enzyme/Protease | Retinyl palmitate is an ester of Retinol and is the major form of vitamin A found in the epidermis. Retinyl palmitate has been widely used in pharmaceutical and cosmetic formulations. | 79-81-2 |
| HY-B1389 | Lactitol (monohydrate) | Others | Others | Lactitol monohydrate is a disaccharide analogue of lactulose. It has been widely used in the treatment of constipation & hepatic encephalopathy. Lactitol is sugar alcohol used as replacement sweeteners. | 81025-04-9 |
| HY-B1391 | D-Panthenol | Endogenous Metabolite | Metabolic Enzyme/Protease | D-Panthenol is the biologically-active alcohol of pantothenic acid, which leads to an elevation in the amount of coenzyme A in the cell. | 81-13-0 |
| HY-B1411 | i-Inositol | Endogenous Metabolite | Metabolic Enzyme/Protease | i-Inositol is a chemical compound, associated lipids are found in many foods, in particular fruit, especially cantaloupe and oranges. | 87-89-8 |
| HY-B1425 | Ethoxyquin | HSP; Reactive Oxygen Species | Cell Cycle/DNA Damage; Immunology/Inflammation; Metabolic Enzyme/Protease; NF-κB | Ethoxyquin is an antioxidant which has been used in animal feed for many years and also an inhibitor of heat shock protein 90 (Hsp90). | 91-53-2 |
| HY-B1431 | Butylparaben | Bacterial; Endogenous Metabolite | Anti-infection; Metabolic Enzyme/Protease | Butylparaben is an organic compound, has proven to be a highly successful antimicrobial preservative in cosmetics, also used in medication suspensions, and as a flavoring additive in food. | 94-26-8 |
| HY-B1465 | 1-Hexadecanol | Endogenous Metabolite | Metabolic Enzyme/Protease | 1-Hexadecanol is a fatty alcohol, a lipophilic substrate. | 36653-82-4 |

TABLE 1-continued

Illustrative additional ingredients

| Catalog No | Drug Names | Target | Pathway | Biological Activity | CAS |
|---|---|---|---|---|---|
| HY-B1521 | Aluminum Hydroxide | Others | Others | Aluminum Hydroxide is an orally active main form of aluminum used as adjuvant. Aluminum hydroxide-based adjuvant researches including the repository effect, pro-phagocytic effect, and activation of the pro-inflammatory NLRP3 pathway. Aluminum Hydroxide also acts as adjuvant to compensate low inherent immunogenicity of subunit vaccines. | 21645-51-2 |
| HY-B1550 | Benzoin | | | | 119-53-9 |
| HY-B1610 | Sodium citrate (dihydrate) | Bacterial | Anti-infection | Sodium citrate dehydrate is an anticoagulant and also used as a buffer and food preservatives. | 6132-04-3 |
| HY-B1620 | Polyvinylpyrrolidone | Others | Others | Polyvinylpyrrolidone is a compound which has been widely tested and used in human and veterinary medicine as an effective wound healing accelerator and disinfectant when combined with iodine and other compounds. | 9003-39-8 |
| HY-B1645 | Ferric Ammonium Citrate | | | | 1185-57-5 |
| HY-B1651 | Iron(II) fumarate | Others | Others | Iron(II) fumarate (Ferrous fumarate) is the iron (II) salt of fumaric acid. Iron(II) fumarate is an orally active dietary supplement and has the potential for iron deficiency anemia treatment. | 141-01-5 |
| HY-B1659 | Glycerol | Endogenous Metabolite | Metabolic Enzyme/Protease | Glycerol is a clear, colourless, viscous, sweet-tasting liquid. Glycerol is used in sample preparation and gel formation for polyacrylamide gel electrophoresis. | 56-81-5 |
| HY-B1673 | Pharmatose DCL 14 | Endogenous Metabolite | Metabolic Enzyme/Protease | Pharmatose DCL 14 is an endogenous metabolite. | 64044-51-5 |
| HY-B1695 | Methyl nicotinate | Others | Others | Methyl nicotinate, the methyl ester of Niacin found in alcoholic beverages, that is used as an active ingredient as a rubefacient in over-the-counter topical prepantions indicated for muscle and joint pain. | 93-60-7 |
| HY-B1731 | Phenyl Salicylate | | | | 118-55-8 |
| HY-B1732 | DL-3-Phenylalanine | | | | 150-30-1 |
| HY-B1779 | Sucrose | Endogenous Metabolite | Metabolic Enzyme/Protease | Sucrose is a disaccharide which is composed of two monosaccharides, glucose and fructose. | 57-50-1 |
| HY-B1804 | Tricaprilin | Endogenous Metabolite | Metabolic Enzyme/Protease | Tricaprilin (Trioctanoin) is used in study for patients with mild to moderate Alzheimer's disease and has a role as an anticonvulsant and a plant metabolite. | 538-23-8 |
| HY-B1812 | 1,2-Dimethoxybenzene | Others | Others | 1,2-Dimethoxybenzene is an naturally occurring insect attractant. | 91-16-7 |
| HY-B1960 | Canthaxanthin | Reactive Oxygen Species | Immunology/Inflammation; Metabolic Enzyme/Protease; NF-κB | Canthaxanthin is a red-orange carotenoid with various biological activities, such as antioxidant, antitumor properties. | 514-78-3 |
| HY-B2118 | Pancreatin | Others | Others | Pancreatin is the porcine pancreas extract (PPE) which contains the main pancreatic digestive enzymes. | 8049-47-6 |
| HY-B2122 | Maltitol | Others | Others | Maltitol is a sugar alcohol used as a sugar substitute. It has 75-90% of the sweetness of sucrose (table sugar) and nearly identical properties. Maltitol may also be used as a plasticizer in gelatin capsules, as an emollient, and as a humectant. | 585-88-6 |

TABLE 1-continued

Illustrative additional ingredients

| Catalog No | Drug Names | Target | Pathway | Biological Activity | CAS |
|---|---|---|---|---|---|
| HY-B2123 | Lactose | Endogenous Metabolite | Metabolic Enzyme/Protease | Lactose, a major sugar in the milk of most species, could regulate human's intestinal microflora. | 63-42-3 |
| HY-B2136 | Tannic acid | Potassium Channel | Membrane Transporter/Ion Channel | Tannic acid is a novel hERG channel blocker with IC50 of 3.4 μM. | 1401-55-4 |
| HY-B2163 | Astaxanthin | PPAR; Reactive Oxygen Species | Cell Cycle/DNA Damage; Immunology/Inflammation; Metabolic Enzyme/Protease; NF-κB | Astaxanthin, a red dietary carotenoid isolated from Haematococcus pluvialis, is a modulator of PPARγ and a potent antioxidant with antiproliferative, neuroprotective and anti-inflammatory activity. Astaxanthin has potential in the study of various diseases, such as cancers and Parkinson's disease, cardiovascular disease. Due to its bright red colour, Astaxanthin could be used as a food colorant in animal feeds. | 472-61-7 |
| HY-B2200 | Calcium citrate tetrahydrate | | | | 5785-44-4 |
| HY-B2201 | Trisodium citrate | | | | 68-04-2 |
| HY-B2203 | Calcium glycerol phosphate | | | | 27214-00-2 |
| HY-B2205 | Magnesium silicate | | | | 1343-88-0 |
| HY-B2217 | Calcium hydroxide | | | | 1305-62-0 |
| HY-B2218 | Magnesium hydroxide | | | | 1309-42-8 |
| HY-B2219 | Stearic acid | Endogenous Metabolite | Metabolic Enzyme/Protease | Stearic acid is a long chain dietary saturated fatty acid which exists in many animal and vegetable fats and oils. | 57-11-4 |
| HY-B2221 | Cellulose | | | | 9004-34-6 |
| HY-B2221B | Hydroxyethyl cellulose | Others | Others | Hydroxyethyl cellulose is a non-ionic, water soluble, modified cellulose polymer used as a thickening agent for aqueous cosmetic and personal care formulations. | 9004-62-0 |
| HY-B2223 | Thiamine nitrate | Others | Others | Thiamine nitrate is an essential vitamin which can enhance normal neuronal actives. | 532-43-4 |
| HY-B2225 | Starch | | | | 9005-25-8 |
| HY-B2226 | Sodium copper chlorophyllin B | HIV; Influenza Virus | Anti-infection | Sodium copper chlorophyllin B exerts antiviral activities against Influenza virus and HIV with IC50s of 50 to 100 μM for both of them. | 28302-36-5 |
| HY-B2227A | Calcium lactate | | | | 814-80-2 |
| HY-B2228 | Proteinase | Others | Others | Proteinase refers to the enzymes with proteolytic activity. | 9001-92-7 |
| HY-B2232 | Benzalkonium (chloride) | Bacterial | Anti-infection | Benzalkonium chloride is a potent anti-microbial agent, used as a preservative in eye drops. | 8001-54-5 |
| HY-B2235 | Lecithin | Endogenous Metabolite | Metabolic Enzyme/Protease | Lecithin is regarded as a safe, conventional phospholipid source. Phospholipids are reported to alter the fatty acid composition and microstructure of the membranes in animal cells. | 8002-43-5 |
| HY-B2237 | Lysozyme from chicken egg white | Bacterial | Anti-infection | Lysozyme from chicken egg white is a bactericidal enzyme present in chicken eggs, and it lyses gram-positive bacteria. IC50 & Target: Bacteria In vitro: Lysozyme is an ubiquitous enzyme. The hen egg is the most abundant source of lysozyme, which constitutes approximately 3.4% of | 12650-88-3 |

TABLE 1-continued

Illustrative additional ingredients

| Catalog No | Drug Names | Target | Pathway | Biological Activity | CAS |
|---|---|---|---|---|---|
| HY-B2241 | Aluminum potassium disulfate dodecahydrate | | | the albumen proteins. Lysozyme is a natural antimicrobial that hydrolyzes the β(1-4) glycosidic linkage between N-acetylmuramic acid and N-acetylglucosamine found in the peptidoglycan layer of the bacterial cell wall and causing cell lysis. The bactericidal effect of lysozyme is primarily limited to gram-positive bacteria, including pathogens such as Listeria monocytogenes and certain Clostridium species as well as some spoilage organisms, including thermophilic spore-forming bacteria and certain yeasts. The gram-negative bacteria are more resistant to lysozyme action because of their complex cell wall structure. | 7784-24-9 |
| HY-B2242 | Calcium phosphate | | | | 7757-93-9 |
| HY-B2243 | Dihydrogen monosodium phosphate | | | | 7558-80-7 |
| HY-D0195 | Acesulfame (potassium) | | | | 55589-62-3 |
| HY-D0227 | Trometamol | Others | Others | Trometamol is a biologically inert amino alcohol of low toxicity, which buffers carbon dioxide and acids in vitro and in vivo. Trometamol is an effective amine compound for pH control in the physiological range. | 77-86-1 |
| HY-D0249 | Sunset Yellow FCF | Others | Others | Sunset Yellow FCF is a petroleum-derived orange azo dye with a pH dependent maximum absorption at about 480 nm at pH 1 and 443 nm at pH 13. Sunset Yellow is used in food, cosmetics, and drugs. | 2783-94-0 |
| HY-D0257 | Tartrazine | Others | Others | Tartrazine is a synthetic lemon yellow azo dye primarily used as a food coloring. Tartrazine is water-soluble and has a maximum absorbance in an aqueous solution at 425 nm. | 1934-21-0 |
| HY-D0259 | Erythrosine B | Others | Others | Erythrosine B is an artificial dye widely used in the food and textile industries. Erythrosine B is also a novel photosensitizer which has been used to develop animal models. | 16423-68-0 |
| HY-D0307A | Amaranth | Others | Others | Amaranth is a dark red to purple azo dye used as a food dye and to color cosmetics. Amaranth is an anionic dye. It can be applied to natural and synthetic fibers, leather, paper, and phenol-formaldehyde resins. | 915-67-3 |
| HY-D0833 | Calcium orthophosphate Hydroxylapatite | | | | 7758-87-4 |
| HY-D0835 | Disodium 5'-inosinate | Others | Others | Disodium 5'-inosinate, obtained from bacterial fermentation of sugars, is as a food additive and often found in a variety of other snacks. | 4691-65-0 |
| HY-D0887 | | | | | |
| HY-D0914 | Fast Green FCF | Others | Others | Fast Green FCF is a sea green triarylmethane food dye. Fast Green FCF is used as a quantitative stain for histones at alkaline pH after acid extraction of DNA. It is also used as a protein stain in electrophoresis. Its absorption maximum is at 625 nm. | 2353-45-9 |
| HY-D0915 | Brilliant Blue FCF | Others | Others | Brilliant Blue FCF has the appearance of a reddish-blue powder. It is soluble in water, and the solution has a maximum absorption at about 628 nanometers. It is a synthetic dye produced using aromatic hydrocarbons from petroleum, is a colorant for foods and other substances. | 3844-45-9 |

TABLE 1-continued

Illustrative additional ingredients

| Catalog No | Drug Names | Target | Pathway | Biological Activity | CAS |
|---|---|---|---|---|---|
| HY-D1005 | Poloxamer 407 | Others | Others | Poloxamer 407 is a nonionic surfactant that is 100% active and relatively non-toxic to cells at low concentrations, and frequently used with dye AM esters such as Indo-1 AM, Fura-2 AM, Calcein AM, Fluo-3 AM, Fluo-4 AM, Quest Fluo-8? AM and Quest Rhod-4? AM, etc. to improve their water solubility. | 9003-11-6 |
| HY-D1005A | Poloxamer 188 | Others | Others | Poloxamer 188 is a nonionic linear copolymer with surfactant properties. Poloxamer 188 exhibits anti-thrombotic, anti-inflammatory, and cytoprotective activities in various tissue injury models. | 691397-13-4 |
| HY-ER013 | Sodium carbonate | | | | 497-19-8 |
| HY-I0301 | D-(+)-Glucono-1,5-lactone | Endogenous Metabolite; Reactive Oxygen Species | Immunology/ Inflammation; Metabolic Enzyme/Protease; NF-κB | D-(+)-Glucono-1,5-lactone is a polyhydroxy (PHA) that is capable of metal chelating, moisturizing and antioxidant activity. | 90-80-2 |
| HY-I0501 | 2'-Aminoacetophenone | Bacterial | Anti-infection | 2'-Aminoacetophenone is an aromatic compound containing a ketone substituted by one alkyl group, and a phenyl group. 2'-Aminoacetophenone can be used as a breath biomarker for the detection of Ps. Aeruginosa infections in the cystic fibrosis lung. | 551-93-9 |
| HY-N0060A | Ferulic acid (sodium) | Endogenous Metabolite; FGFR; Reactive Oxygen Species | Immunology/ Inflammation; Metabolic Enzyme/Protease; NF-κB; Protein Tyrosine Kinase/RTK | Ferulic acid sodium is a novel fibroblast growth factor receptor 1 (FGFR1) inhibitor with IC50s of 3.78 and 12.5 μM for FGFR1 and FGFR2, respectively. | 24276-84-4 |
| HY-N0098 | Vanillin | Endogenous Metabolite | Metabolic Enzyme/Protease | Vanillin (p-Vanillin) is a single molecule extracted from vanilla beans and also a popular odor used widely in perfume, food and medicine. | 121-33-5 |
| HY-N0119 | Naringin Dihydrochalcone | NF-κB | NF-κB | Naringin Dihydrochalcone is an artificial sweetener derived from naringin. Naringin is a major flavanone glycoside obtained from tomatoes, grapefruits, and many other citrus fruits. Naringin exhibits biological properties such as antioxidant, anti-inflammatory, and antiapoptotic activities. Naringin suppresses NF-κB signaling pathway. | 18916-17-1 |
| HY-N0129 | Sclareolide | Bacterial | Anti-infection | Sclareolide is isolated from the flower of Salvia sclarea with antibacterial and cytotoxic activities. | 564-20-5 |
| HY-N0138 | Theobromine | Adenosine Receptor; Endogenous Metabolite | GPCR/G Protein; Metabolic Enzyme/Protease | Theobromine is a methylxanthine found in cacao beans which can inhibit adenosine receptor A1 (AR1) signaling | 83-67-0 |
| HY-N0142 | Phloretin | Endogenous Metabolite; GLUT; SGLT | Membrane Transporter/Ion Channel; Metabolic Enzyme/Protease | Phloretin (NSC 407292; RJC 02792) is a flavonoid extracted from Prunus mandshurica, has anti-inflammatory activities. Phloridzin is a specific, competitive and orally active inhibitor of sodium/glucose cotransporters in the intestine (SGLT1) and kidney (SGLT2). Phloretin inhibits Yeast-made GLUT1 as well as Human erythrocyte GLUT1 with IC50 values of 49 μM and 61 μM, respectively. Phloretin has the potential for the treatment of rheumatoid arthritis (RA) and allergic airway inflammation. | 60-82-2 |

TABLE 1-continued

Illustrative additional ingredients

| Catalog No | Drug Names | Target | Pathway | Biological Activity | CAS |
|---|---|---|---|---|---|
| HY-N0144 | Piperine | Autophagy; Endogenous Metabolite; P-glycoprotein | Autophagy; Membrane Transporter/Ion Channel; Metabolic Enzyme/Protease | Piperine, a natural alkaloid isolated from Piper nigrum L, inhibits P-glycoprotein and CYP3A4 activities with an IC50 value of 61.94 ± 0.054 μg/mL in HeLa cell. | 94-62-2 |
| HY-N0148 | Rutin | Autophagy; Endogenous Metabolite; Influenza Virus; Reactive Oxygen Species | Anti-infection; Autophagy; Immunology/Inflammation; Metabolic Enzyme/Protease; NF-κB | Rutin, a naturally occurring flavonoid glycoside, has antioxidant, anti-inflammatory, anti-allergic, anti-angiogenic and antiviral properties. | 153-18-4 |
| HY-N0154 | Neohesperidin dihydrochalcone | Reactive Oxygen Species | Immunology/Inflammation; Metabolic Enzyme/Protease; NF-κB | Neohesperidin dihydrochalcone is a synthetic glycoside chalcone, is added to various foods and beverages as a low caloric artificial sweetener. | 20702-77-6 |
| HY-N0163 | Magnolol | Autophagy; Bacterial; PPAR; RAR/RXR | Anti-infection; Autophagy; Cell Cycle/DNA Damage; Metabolic Enzyme/Protease | Magnolol, a natural lignan isolated from the stem bark of Magnolia officinalis, is a dual agonist of both RXRα and PPARγ, with EC50 values of 10.4 μM and 17.7 μM, respectively. | 528-43-8 |
| HY-N0168 | Hesperetin | Apoptosis; Autophagy; p38 MAPK | Apoptosis; Autophagy; MAPK/ERK Pathway | Hesperetin is a natural flavanone, and acts as a potent and broad-spectrum inhibitor against human UGT activity. Hesperetin induces apoptosis via p38 MAPK activation. | 520-33-2 |
| HY-N0184 | Glycyrrhizic acid | Virus Protease | Anti-infection | Glycyrrhizic acid is a triterpenoid saponin, acting as a direct HMGB1 antagonist, with anti-tumor, anti-diabetic activities. | 1405-86-3 |
| HY-N0198 | Nordihydroguaiaretic acid | Autophagy; Ferroptosis; Lipoxygenase | Apoptosis; Autophagy; Metabolic Enzyme/Protease | Nordihydroguaiaretic acid is a 5-lipoxygenase (5LOX) (IC50 = 8 μM) and tyrosine kinase inhibitor. | 500-38-9 |
| HY-N0215 | L-Phenylalanine | Calcium Channel; Endogenous Metabolite; iGluR | Membrane Transporter/Ion Channel; Metabolic Enzyme/Protease; Neuronal Signaling | L-Phenylalanine ((S)-2-Amino-3-phenylpropionic acid) is an essential amino acid isolated from Escherichia coli. L-Phenylalanine is α2δ subunit of voltage-dependent Ca+ channels antagonist with a Ki of 980 nM. L-phenylalanine is a competitive antagonist for the glycine- and glutamate-binding sites of N-methyl-D-aspartate receptors (NMDARs) (KB of 573 μM ) and non-NMDARs, respectively. L-Phenylalanine is widely used in the production of food flavors and pharmaceuticals. | 63-91-2 |
| HY-N0216 | Benzoic acid | Bacterial; Endogenous Metabolite; Fungal | Anti-infection; Metabolic Enzyme/Protease | Benzoic acid is an aromatic alcohol existing naturally in many plants and is a common additive to food, drinks, cosmetics and other products. It acts as preservatives through inhibiting both bacteria and fungi. | 65-85-0 |
| HY-N0229 | L-Alanine | Endogenous Metabolite | Metabolic Enzyme/Protease | L-Alanine is a non-essential amino acid, involved in sugar and acid metabolism, increases immunity, and provides energy for muscle tissue, brain, and central nervous system. | 56-41-7 |

TABLE 1-continued

Illustrative additional ingredients

| Catalog No | Drug Names | Target | Pathway | Biological Activity | CAS |
|---|---|---|---|---|---|
| HY-N0230 | β-Alanine | Endogenous Metabolite | Metabolic Enzyme/Protease Apoptosis | β-Alanine is a non-essential amino acid that is shown to be metabolized into carnosine, which functions as an intracellular buffer. | 107-95-9 |
| HY-N0264 | Tetramethylpyrazine | Apoptosis | | Tetramethylpyrazine (Ligustrazine), an alkylpyrazine isolated from Ligusticum wallichii (Chuan Xiong), is present in french fries, bread, cooked meats, tea, cocoa, coffee, beer, spirits, peanuts, filberts, dairy products and soy products as fragrance and flavouring ingredients exhibits. Tetramethylpyrazine (Ligustrazine) also has potential nootropic and anti-inflammatory activities in rats. | 1124-11-4 |
| HY-N0287 | Lycopene | Reactive Oxygen Species | Immunology/ Inflammation; Metabolic Enzyme/Protease; NF-κB | Lycopene is naturally occurring carotenoids found in tomato, tomato products, and in other red fruits and vegetables; exhibits antioxidant effects. | 502-65-8 |
| HY-N0294 | Protocatechuic acid | Others | Others | Protocatechuic acid is a phenolic compound which exhibits neuroprotective effect. | 99-50-3 |
| HY-N0324 | Cholic acid | Endogenous Metabolite | Metabolic Enzyme/Protease | Cholic acid is a major primary bile acid produced in the liver and usually conjugated with glycine or taurine. It facilitates fat absorption and cholesterol excretion. | 81-25-4 |
| HY-N0325 | DL-Methionine | Endogenous Metabolite | Metabolic Enzyme/Protease | L-Methionine is the L-isomer of Methionine, an essential amino acid for human development. Methionine acts as a hepatoprotectant. | 59-51-8 |
| HY-N0326 | L-Methionine | | | | 63-68-3 |
| HY-N0336 | 3-Butylidenephthalide | Parasite | Anti-infection | 3-Butylidenephthalide (Butylidenephthalide) is a phthalic anhydride derivative identified in Ligusticum chuanxiong Hort, and has larvicidal activity (LC50 of 1.56 mg/g for Spodoptera litum larvae). | 551-08-6 |
| HY-N0337 | Eugenol | Apoptosis; Bacterial; Ferroptosis; Parasite; Reactive Oxygen Species | Anti-infection; Apoptosis; Immunology/ Inflammation; Metabolic Enzyme/Protease; NF-κB | Eugenol is an essential oil found in cloves with antibacterial, anthelmintic and antioxidant activity. Eugenol is shown to inhibit lipid peroxidation. | 97-53-0 |
| HY-N0349 | Methyl Paraben | Bacterial; Endogenous Metabolite | Anti-infection; Metabolic Enzyme/Protease | Methyl Paraben, isolated from the barks of Tsuga dumosa the methyl ester of p-hydroxybenzoic acid, is a standardized chemical allergen. Methyl Paraben is a stable, non-volatile compound used as an antimicrobial preservative in foods, drugs and cosmetics. The physiologic effect of Methyl Paraben is by means of increased histamine release, and cell-mediated immunity. | 99-76-3 |
| HY-N0367 | Trans-Anethole | Endogenous Metabolite | Metabolic Enzyme/Protease | Trans-Anethole ((E)-Anethole), a phenylpropene derivative isolated from Pimpinella, shows estrogenic activity at lower concentrations and cytotoxic at higher concentrations in cancer cell lines. Trans-Anethole ((E)-Anethole) contributes a large component of the odor and flavor of anise and fennel, anise myrtle, liquorice, camphor, magnolia blossoms, and star anise. | 4180-23-8 |

TABLE 1-continued

Illustrative additional ingredients

| Catalog No | Drug Names | Target | Pathway | Biological Activity | CAS |
|---|---|---|---|---|---|
| HY-N0368 | Linalool | Apoptosis; Endogenous Metabolite; iGluR | Apoptosis; Membrane Transporter/Ion Channel; Metabolic Enzyme/Protease; Neuronal Signaling | Linalool is natural monoterpene in essential oils of coriander, acts as a competitive antagonist of N-methyl d-aspartate (NMDA) receptor, with anti-tumor, anti-cardiotoxicity activity. Linalool is a PPARα ligand that reduces plasma TG levels and rewires the hepatic transcriptome and plasma metabolome. | 78-70-6 |
| HY-N0378 | D-Mannitol | Apoptosis; Endogenous Metabolite | Apoptosis; Metabolic Enzyme/Protease | D-Mannitol is an osmotic diuretic agent and a weak renal vasodilator. Target: Others D(−)Mannitol is a sugar alcohol that can be used as an inert osmotic control substance. The uptake and phosphorylation of d-mannitol is catalyzed by the mannitol-specific phosphoenolpyruvate-dependent phosphotransferase systems (PTS) Mannitol can interact with neutrophils and monocytes. Experiments have shown that it is able to decrease neutrophil apoptosis in vitro. The compound has been used in studies as a stimulator of cecal microbial growth and cellulolytic activity in rabbits. It has been observed that mannitol can lower the fat digestibility and body fat accumulation in both normal and cecectomized rats, as well as upregulate monocyte HLA-DR, monocyte and neutrophil CD11b. Studies show that the mannitol operon is repressed by the transcription factor, mannitol operon repressor (MtlR) in Escherichia coli. | 69-65-8 |
| HY-N0390 | L-Glutamine | Endogenous Metabolite; Ferroptosis; mGluR | Apoptosis; GPCR/G Protein; Metabolic Enzyme/Protease; Neuronal Signaling | L-Glutamine is a non-essential amino acid present abundantly throughout the body and is involved in gastrointestinal disorders. Target: mGluR Glutamine (abbreviated as Gln or Q) is one of the 20 amino acids encoded by the standard genetic code. It is not recognized as an essential amino acid, but may become conditionally essential in certain situations, including intensive athletic training or certain gastrointestinal disorders. Its side-chain is an amide formed by replacing the side-chain hydroxyl of glutamic acid with an amine functional group, making it the amide of glutamic acid. Its codons are CAA and CAG. In human blood, glutamine is the most abundant free amino acid, with a concentration of about 500-900 μmol/L. Glutamine is synthesized by the enzyme glutamine synthetase from glutamate and ammonia. The most relevant glutamine-producing tissue is the muscle mass, accounting for about 90% of all glutamine synthesized. Glutamine is also released, in small amounts, by the lung and the brain. Although the liver is capable of relevant glutamine synthesis, its role in glutamine metabolism is more regulatory than producing, since the liver takes up large amounts of glutamine derived from the gut. The most eager consumers of glutamine are the cells of intestines, the kidney cells for the acid-base balance, activated immune cells, and manycancer cells. In respect to the last point mentioned, different glutamine analogues, such as DON, Azaserine or Acivicin, are tested as anticancer drugs. | 56-85-9 |
| HY-N0394 | L-Cystine | Endogenous Metabolite; Ferroptosis | Apoptosis; Metabolic Enzyme/Protease | L-Cystine is an amino acid and intracellular thiol, which plays a critical role in the regulation of cellular processes. | 56-89-3 |

TABLE 1-continued

Illustrative additional ingredients

| Catalog No | Drug Names | Target | Pathway | Biological Activity | CAS |
|---|---|---|---|---|---|
| HY-N0411 | β-Carotene | Endogenous Metabolite | Metabolic Enzyme/Protease | β-Carotene (Provitamin A) is an organic compound and classified as a terpenoid. It is a precursor (inactive form) of vitamin A. | 7235-40-7 |
| HY-N0420 | Succinic acid | Endogenous Metabolite | Metabolic Enzyme/Protease | Succinic acid is an intermediate product of the tricarboxylic acid cycle, as well as one of fermentation products of anaerobic metabolism. | 110-15-6 |
| HY-N0445 | 2-Hydroxy-4-methoxybenzaldehyde | Tyrosinase | Metabolic Enzyme/Protease | 2-Hydroxy-4-methoxybenzaldehyde, a chemical compound and an isomer of Vanillin, could be used to synthesis Urolithin M7. 2-hydroxy-4-methoxybenzaldehyde is a potent tyrosinase inhibitor from three East African medicinal plants, *Mondia whitei*, *Rhus vulgaris* Meikle, and *Sclerocarya caffra* Sond. | 673-22-3 |
| HY-N0455 | L-Arginine | Endogenous Metabolite; NO Synthase | Immunology/Inflammation; Metabolic Enzyme/Protease | L-Arginine is the nitrogen donor for synthesis of nitric oxide, a potent vasodilator that is deficient during times of sickle cell crisis. Target: Others L-Arginine is an α-amino acid. It was first isolated in 1886. The L-form is one of the 20 most common natural amino acids. At the level of molecular genetics, in the structure of the messenger ribonucleic acid mRNA, CGU, CGC, CGA, CGG, AGA, and AGG, are the triplets of nucleotide bases or codons that code for arginine during protein synthesis. In mammals, arginine is classified as a semiessential or conditionally essential amino acid, depending on the developmental stage and health status of the individual. L-Arginine is associated with a decrease in cardiac index while stroke index is maintained in patients with severe sepsis. Resolution of shock at 72 hours is achieved by 40% and 24% of the patients in the L-Arginine and placebo cohorts, respectively. L-Arginine (450 mg/kg during a 15-minute period) amplifies and sustains the hyperemia (38%) and increases absolute brain blood flow after eNOS upregulation by chronic simvastatin treatment (2 mg/kg subcutaneously, daily for 14 days) in SV-129 mice. | 74-79-3 |
| HY-N0466 | Rebaudioside A | Endogenous Metabolite; Glucosidase | Metabolic Enzyme/Protease | Rebaudioside A is a steviol glycoside, α-glucosidase inhibitor with IC50 of 35.01 μg/ml. can inhibit ATP-sensitive K+-channels. Target: α-glucosidase IC 50: 35.01 ug/mL In vitro: rebaudioside A stimulat the insulin secretion from MIN6 cells in a dose- and glucose-dependent manner. In conclusion, the insulinotropic effect of rebaudioside A is mediated via inhibition of ATP-sensitive K+-channels and requires the presence of high glucose. In vivo: in vivo mouse micronucleus test at doses up to 750 mg/kg bw and an unscheduled DNA synthesis test in rats at doses up to 2000 mg/kg bw, rebaudioside A do not cause any genotoxic effects at any of the doses tested. | 58543-16-1 |
| HY-N0467 | Rebaudioside C | Endogenous Metabolite | Metabolic Enzyme/Protease | Rebaudioside C(Dulcoside B) is used as natural sweeteners to diabetics and others on carbohydrate-controlled diets. | 63550-99-2 |
| HY-N0469 | L-Lysine | Endogenous Metabolite; Virus Protease | Anti-infection; Metabolic Enzyme/Protease | L-lysine is an essential amino acid with important roles in connective tissues and carnitine synthesis, energy production, growth in children, and maintenance of immune functions. | 56-87-1 |
| HY-N0473 | L-Tyrosine | Endogenous Metabolite | Metabolic Enzyme/Protease | L-Tyrosine is a non-essential amino acid which can inhibit citrate synthase activity in the posterior cortex. | 60-18-4 |
| HY-N0486 | L-Leucine | mTOR | PI3K/Akt/mTOR | L-Leucine is an essential branched-chain amino acid (BCAA), which activates the mTOR signaling pathway. | 61-90-5 |

TABLE 1-continued

Illustrative additional ingredients

| Catalog No | Drug Names | Target | Pathway | Biological Activity | CAS |
|---|---|---|---|---|---|
| HY-N0524 | Propyl gallate | Others | Others | Propyl gallate is a common food antioxidant. Propyl gallate can inhibit the production of acrolein, glyoxal and methylglyoxal. | 121-79-9 |
| HY-N0537 | Xylose | Endogenous Metabolite | Metabolic Enzyme/Protease | Xylose, a natural product, can be catalyzed into xylulose by xylose isomerase, and it is the key step for anaerobic ethanolic fermentation of xylose. | 58-86-6 |
| HY-N0538 | Xylitol | Autophagy; Endogenous Metabolite | Autophagy; Metabolic Enzyme/Protease | Xylitol is a chemical categorized as a polyalcohol or sugar alcohol. Target: Others Xylitol is a chemical categorized as a polyalcohol or sugar alcohol (alditol). Xylitol has the formula (CHOH)3(CH2OH)2 and is an achiral isomer of pentane-1,2,3,4,5-pentol. Xylitol is used as a diabetic sweetener which is roughly as sweet as sucrose with 33% fewer calories. Unlike other natural or synthetic sweeteners, xylitol is actively beneficial for dental health by reducing caries to a third in regular use and helpful to remineralization. Xylitol is naturally found in low concentrations in the fibers of many fruits and vegetables, and can be extracted from various berries, oats, and mushrooms, as well as fibrous material such as corn husks and sugar cane bagasse and birch. | 87-99-0 |
| HY-N0593 | Deoxycholic acid | Endogenous Metabolite; GPCR19 | GPCR/G Protein; Metabolic Enzyme/Protease | Deoxycholic acid is specifically responsible for activating the G protein-coupled bile acid receptor TGR5 that stimulates brown adipose tissue (BAT) thermogenic activity. | 83-44-3 |
| HY-N0609 | Cinnamaldehyde | Apoptosis; Bacterial | Anti-infection; Apoptosis | Cinnamaldehyde is a major and a bioactive compound isolated from the leaves of Cinnamomum osmophloeum kaneh. Cinnamaldehyde is a cytokine production inhibitor. Cinnamaldehyde has anti-bacteria, anti-oxidation, and anti-inflammatory properties. | 104-55-2 |
| HY-N0610A | Cinnamic acid | Endogenous Metabolite | Metabolic Enzyme/Protease | Cinnamic acid has potential use in cancer intervention, with IC50s of 1-4.5 mM in glioblastoma, melanoma, prostate and lung carcinoma cells. | 621-82-9 |
| HY-N0614 | Sucralose | Endogenous Metabolite | Metabolic Enzyme/Protease | Sucralose is an intense organochlorine artificial sweetener. | 56038-13-2 |
| HY-N0623 | L-Tlyptophan | Endogenous Metabolite | Metabolic Enzyme/Protease | L-Tlyptophan (Tryptophan) is an essential amino acid that is the precursor of serotonin, melatonin, and vitamin B3. | 73-22-3 |
| HY-N0626 | Sorbic acid | Antibiotic; Bacterial; Endogenous Metabolite; Fungal | Anti-infection; Metabolic Enzyme/Protease | Sorbic acid, isolated from Sorbus aucuparia, is a naturally occurring, highly efficient, and nonpoisonous?food preservative.?Sorbic acid generally is an effective inhibitor of most molds and yeasts and some bacteria. | 110-44-1 |
| HY-N0633 | Muscone | Interleukin Related; NF-κB; NOD-like Receptor (NLR); TNF Receptor | Apoptosis; Immunology/Inflammation; NF-κB | Muscone is the main active monomer of traditional Chinese medicine musk. Muscone inhibits NF-κB and NLRP3 inflammasome activation. Muscone remarkably decreases the levels of inflammatory cytokines (IL-1β, TNF-α and IL-6), and ultimately improves cardiac function and survival rate. | 541-91-3 |
| HY-N0650 | L-Serine | Endogenous Metabolite | Metabolic Enzyme/Protease | L-Serine ((−)-Serine; (S)-Serine), one of the so-called non-essential amino acids, plays a central role in cellular proliferation. | 56-45-1 |
| HY-N0658 | L-Threonine | Endogenous Metabolite | Metabolic Enzyme/Protease | L-Threonine is a natural amino acid, can be produced by microbial fermentation, and is used in food, medicine, or feed. | 72-19-5 |
| HY-N0666 | L-Aspartic acid | Endogenous Metabolite | Metabolic Enzyme/Protease | L-Aspartic acid is an amino acid, shown to be a suitable prodrug for colon-specific drug delivery. | 56-84-8 |

TABLE 1-continued

Illustrative additional ingredients

| Catalog No | Drug Names | Target | Pathway | Biological Activity | CAS |
|---|---|---|---|---|---|
| HY-N0667 | L-Asparagine | Endogenous Metabolite | Metabolic Enzyme/Protease | L-Asparagine ((−)-Asparagine) is a non-essential amino acid that is involved in the metabolic control of cell functions in nerve and brain tissue. | 70-47-3 |
| HY-N0679 | Retinyl acetate | Others | Others | Retinyl acetate is a synthetic acetate ester form derived from retinol and has potential antineoplastic and chemo preventive activities. | 127-47-9 |
| HY-N0680 | Thiamine hydrochloride | Apoptosis; Endogenous Metabolite; HBV | Anti-infection; Apoptosis; Metabolic Enzyme/Protease | Thiamine hydrochloride is an essential micronutrient needed as a cofactor for many central metabolic enzymes. | 67-03-8 |
| HY-N0681 | D-Pantothenic acid (hemicalcium salt) | Apoptosis; Endogenous Metabolite | Apoptosis; Metabolic Enzyme/Protease | D-Pantothenic acid hemicalcium salt (Vitamin B5 calcium salt), a vitamin, can reduce the patulin content of the apple juice. IC50 value: Target: In vitro: In human dermal fibroblasts from three different donors, D-Pantothenic acid hemicalcium salt accelerates the wound healing process by increasing the number of migrating cells, their distance and hence their speed. In addition, cell division is increased and the protein synthesis changed. In vivo: | 137-08-6 |
| HY-N0682 | Pyridoxine (hydrochloride) | Endogenous Metabolite; Keap1-Nrf2 | Metabolic Enzyme/Protease; NF-κB | Pyridoxine hydrochloride (Pyridoxol; Vitamin B6) is a pyridine derivative. Pyridoxine (Pyridoxol; Vitamin B6) exerts antioxidant effects in cell model of Alzheimer's disease via the Nrf-2/HO-1 pathway. | 58-56-0 |
| HY-N0708 | Vanillic acid | Bacterial; Endogenous Metabolite; NF-κB | Anti-infection; Metabolic Enzyme/Protease; NF-κB | Vanillic acid is a flavoring agent found in edible plants and fruits Vanillic acid inhibits NF-κB activation. Anti-inflammatory, antibacterial, and chemopreventive effects. | 121-34-6 |
| HY-N0709 | Coumarin | Influenza Virus | Anti-infection | Coumarin is the primary bioactive ingredient in Radix Glehniae, named Beishashen in China, which possesses many pharmacological activities, including anticancer, anti-inflammation and antivirus activities. | 91-64-5 |
| HY-N0711 | Carvacrol | Apoptosis; Endogenous Metabolite; Fungal; Notch | Anti-infection; Apoptosis; Metabolic Enzyme/Protease; Neuronal Signaling; Stem Cell/Wnt | Carvacrol is a monoterpenoid phenol isolated from Lamiaceae family plants, with antioxidant, anti-inflammatory and anticancer properties. Carvacrol causes cell cycle arrest in G0/G1, downregulates Notch-1, and Jagged-1, and induces apoptosis. | 499-75-2 |
| HY-N0717 | L-Valine | Endogenous Metabolite | Metabolic Enzyme/Protease | L-Valine is one of 20 proteinogenic amino acids. L-Valine is an essential amino acid. | 72-18-4 |
| HY-N0729 | Linoleic acid | Endogenous Metabolite | Metabolic Enzyme/Protease | Linoleic acid is a critical component of polyunsaturated fatty acids. | 60-33-3 |
| HY-N0756 | Bornyl acetate | Apoptosis | Apoptosis | Bornyl acetate is a potent odorant, exhibiting one of the highest flavor dilution factor (FD factor). | 76-49-3 |
| HY-N0771 | L-Isoleucine | Endogenous Metabolite | Metabolic Enzyme/Protease | L-isoleucine is a nonpolar hydrophobic amino acid. L-Isoleucine is an essential amino acid. | 73-32-5 |
| HY-N0830 | Palmitic acid | Endogenous Metabolite | Metabolic Enzyme/Protease | Palmitic acid is a long-chain saturated fatty acid commonly found in both animals and plants. | 57-10-3 |

TABLE 1-continued

Illustrative additional ingredients

| Catalog No | Drug Names | Target | Pathway | Biological Activity | CAS |
|---|---|---|---|---|---|
| HY-N0832 | L-Histidine | Endogenous Metabolite; Mitochondrial Metabolism | Metabolic Enzyme/Protease | L-Histidine is an essential amino acid for infants. L-Histidine is an inhibitor of mitochondrial glutamine transport. | 71-00-1 |
| HY-N1096 | Veratraldehyde | Others | Others | Veratraldehyde is an important chemical used in perfumery, agrochemical, and pharmaceutical industries. | 120-14-9 |
| HY-N1132A | D-(+)-Trehalose dihydrate | Others | Others | D-(+)-Trehalose dihydrate, isolated from Saccharomyces cerevisiae, can be used as a food ingredient and pharmaceutical excipient. | 6138-23-4 |
| HY-N1390 | Syringaldehyde | COX | Immunology/Inflammation | Syringaldehyde is a polyphenolic compound belonging to the group of flavonoids and is found in different plant species like Manihot esculenta and Magnolia officinalis. Syringaldehyde moderately inhibits COX-2 activity with an IC50 of 3.5 μg/mL. Anti-hyperglycemic and anti-inflammatory activities. | 134-96-3 |
| HY-N1393 | 2-Methoxybenzoic acid | Endogenous Metabolite | Metabolic Enzyme/Protease | 2-Methoxybenzoic acid (NSC 3778) is used as an internal standard of salicylic acid and its putative biosynthetic precursors in cucumber leaves. Another known use is in the synthesis of Benextramine. | 579-75-9 |
| HY-N1394 | p-Anisic acid | Bacterial; Endogenous Metabolite | Anti-infection; Metabolic Enzyme/Protease | p-Anisic acid (4-Methoxybenzoic acid) is one of the isomers of anisic acid, with anti-bacterial and antiseptic properties. | 100-09-4 |
| HY-N1406 | 6-Methylcoumarin | Others | Others | 6-Methylcoumarin is a synthetic fragrance widely used in cosmetics. | 92-48-8 |
| HY-N1415 | β-Caryophyllene | Cannabinoid Receptor; Endogenous Metabolite | GPCR/G Protein; Metabolic Enzyme/Protease; Neuronal Signaling | β-Caryophyllene is a CB2 receptor agonist. | 87-44-5 |
| HY-N1420 | Rhamnose | Endogenous Metabolite | Metabolic Enzyme/Protease | Rhamnose (L-Rhamnose) is a monosaccharide found in plants and bacteria. Rhamnose-conjugated immunogens is used in immunotherapies. Rhamnose crosses the epithelia via the transcellular pathway and acts as a marker of intestinal absorption. | 3615-41-6 |
| HY-N1423 | Glycocholic acid | Bcl-2 Family; Endogenous Metabolite | Apoptosis; Metabolic Enzyme/Protease | Glycocholic acid is a bile acid with anticancer activity, targeting against pump resistance-related and non-pump resistance-related pathways. | 475-31-0 |
| HY-N1426 | Raspberry ketone | PPAR | Cell Cycle/DNA Damage | Raspberry ketone is a major aromatic compound of red raspberry, widely used as a fragrance in cosmetics and as a flavoring agent in foodstuff; also shows PPAR-α agonistic activity. | 5471-51-2 |
| HY-N1428 | Citric acid | Antibiotic; Apoptosis; Bacterial; Endogenous Metabolite | Anti-infection; Apoptosis; Metabolic Enzyme/Protease | Citric acid is a weak organic tricarboxylic acid found in citrus fruits. Citric acid is a natural preservative and food tartness enhancer. | 77-92-9 |
| HY-N1428A | 2-Hydroxy-1,2,3-propanetricarboxylic acid monohydrate | | | | |

TABLE 1-continued

Illustrative additional ingredients

| Catalog No | Drug Names | Target | Pathway | Biological Activity | CAS |
|---|---|---|---|---|---|
| HY-N1446 | Oleic acid | Apoptosis; Endogenous Metabolite; Na+/K+ ATPase | Apoptosis; Membrane Transporter/Ion Channel; Metabolic Enzyme/Protease | Oleic acid is an abundant monounsaturated fatty acid. Oleic acid is a Na+/K+ ATPase activator. | 112-80-1 |
| HY-N1500 | Pulegone | Endogenous Metabolite; TRP Channel | Membrane Transporter/Ion Channel; Metabolic Enzyme/Protease; Neuronal Signaling | Pulegone, the major chemical constituent of Calamintha nepeta (L.) Savi essential oil which is an aromatic heth with a mint-oregano flavor, is one of avian repellents. The molecular target for the repellent action of Pulegone in avian species is nociceptive TRP ankyrin 1 (TRPA1). Pulegone stimulates both TRPM8 and TRPA1 channel in chicken sensory neurons and suppresses the former but not the latter at high concentrations. | 89-82-7 |
| HY-N1925 | Tea polyphenol | Others | Others | Tea polyphenol is the floorboard of phenolic compounds in tea. Tea polyphenol exhibits biological activity including antioxidant and anti-cancer activities, inhibition of cell proliferation, induction of apoptosis, cell cycle arrest and modulation of carcinogen metabolism. | 84650-60-2 |
| HY-N1926 | Dihydrocoumarin | Sirtuin | Cell Cycle/DNA Damage; Epigenetics | Dihydrocoumarin is a compound found in Melilotus officinalis. Dihydrocoumarin is a yeast Sir2p inhibitor. Dihydrocoumarin also inhibits human SIRT1 and SIRT2 with IC50s of 208 µM and 295 µM, respectively. | 119-84-6 |
| HY-N1944 | Nerolidol | Bacterial; Endogenous Metabolite; Fungal; Parasite | Anti-infection; Metabolic Enzyme/Protease | Nerolidol is a natural membrane-active sesquiterpene, with antitumor, antibacterial, antifungal and antiparasitic activity. | 7212-44-4 |
| HY-N2011 | Octyl gallate | Bacterial; HSV; Influenza Virus; Reactive Oxygen Species | Anti-infection; Immunology/Inflammation; Metabolic Enzyme/Protease; NF-κB | Octyl gallate (Progallin O) is widely used as a food additive, with antimicrobial and antioxidant activity. Octyl gallate (Progallin O) shows selective and sensitive fluorescent property. Octyl gallate shows a marked antiviral effect against HSV-1, vesicular stomatitis virus (VSV) and poliovirus. | 1034-01-1 |
| HY-N2024 | Maltose | | | | 69-79-4 |
| HY-N2026 | Propylparaben | Bacterial; Endogenous Metabolite | Anti-infection; Metabolic Enzyme/Protease | Propylparaben is an antimicrobial agent, preservative, flavouring agent. | 94-13-3 |
| HY-N2041 | Myristic acid | Endogenous Metabolite | Metabolic Enzyme/Protease | Myristic acid is a saturated 14-carbon fatty acid occurring in most animal and vegetable fats, particularly butterfat and coconut, palm, and nutmeg oils. | 544-63-8 |
| HY-N2067 | Vanillyl alcohol | Apoptosis | Apoptosis | Vanillyl alcohol (p-(Hydroxymethyl)guaiacol), derived from vanillin, is a phenolic alcohol and is used as a flavoring agent in foods and beverages. | 498-00-0 |
| HY-N2071 | Cedrol | Cytochrome P450; Fungal | Anti-infection; Metabolic Enzyme/Protease | Cedrol is a bioactive sesquiterpene, a potent competitive inhibitor of cytochrome P-450 (CYP) enzymes. Cedrol inhibits CYP2B6-mediated bupropion hydroxylase and CYP3A4-mediated midazolam hydroxylation with Ki of 0.9 µM and 3.4 µM, respectively. Cedrol also has weak inhibitory effect on CYP2C8, CYP2C9, and CYP2C19 enzymes. Cedrol is found in cedar essential oil and poetesses anti-septic, anti-inflammatory, anti-spasmodic, tonic, astringent, diuretic, sedative, insecticidal, and anti-fungal activities. | 77-53-2 |

TABLE 1-continued

Illustrative additional ingredients

| Catalog No | Drug Names | Target | Pathway | Biological Activity | CAS |
|---|---|---|---|---|---|
| HY-N2086 | Ethyl palmitate | Others | Others | | 628-97-7 |
| HY-N2195 | Nootkatone | Others | Others | Nootkatone, a neuroprotective agent from Alpiniae Oxyphyllae Fructus, has antioxidant and anti-inflammatory effects. Nootkatone improves cognitive impairment in lipopolysaccharide-induced mouse model of Alzheimer's disease. | 4674-50-4 |
| HY-N2362 | Alanine | | | | 302-72-7 |
| HY-N3025 | Zinc sulfate (heptahydrate) | Others | Others | Zinc sulfate heptahydrate is a hydrate that is the heptahydrate form of zinc sulfate. Zinc sulfate heptahydrate is a dietary supplement used for zinc deficiency and to prevent the condition in those at high risk. | 7446-20-0 |
| HY-N3075 | Phytol | Bacterial; Parasite | Anti-infection | Phytol ((E)-?Phytol), a diterpene alcohol from chlorophyll widely used as a food additive and in medicinal fields, possesses promising antischistosomal properties. Phytol has antinociceptive and antioxidant activitiesas well as anti-inflammatory and antiallergic effects. Phytol has antimicrobial activity against *Mycobacterium tuberculosis* and *Staphylococcus aureus*. | 150-86-7 |
| HY-N3544 | Caryophyllene oxide | Endogenous Metabolite | Metabolic Enzyme/Protease | Caryophyllene oxide, isolated from from Annona squamosa L. bark, possesses analgesic and anti-inflammatory activity. | 1139-30-6 |
| HY-N4100 | Trilobatin | HIV; SGLT | Anti-infection; Membrane Transporter/Ion Channel | Trilobatin, a natural sweetener derived from?Lithocarpus polystachyus?Rehd, Trilobatin?is an HIV-1 entry inhibitor targeting the HIV-1 Gp41 envelope. Neuroprotective effects. Trilobatin is also a SGLT1/2 inhibitor that selectively induces the proliferation of human hepatoblastoma cells. | 4192-90-9 |
| HY-N5132 | (−)-Fenchone | Others | Others | (−)-Fenchone, a bicyclic monoterpene, is widely distributed in plants and found in essential oils from Thuja occidentalis. (−)-Fenchone is oxidized to 6-endo-hydroxyfenchone, 6-exo-hydroxyfenchone and 10-hydroxyfenchone derivatives by CYP2A6 and CYP2B6 in human liver microsomes with CYP2A6 playing a more important role than CYP2B6. | 7787-20-4 |
| HY-N5142 | α-Terpineol | Bacterial | Anti-infection | α-Terpineol is isolated from *Eucalyptus globulus* Labill, exhibits strong antimicrobial activity against periodontopathic and cariogenic bacteria. α-Terpineol possesses antifungal activity against *T. mentagrophytes*, and the activity might lead to irreversible cellular disruption. | 98-55-5 |
| HY-N6056 | Pentanoic acid | | | | 109-52-4 |
| HY-N6655 | DL-Methionine methylsulfonium (chloride) | Others | Others | DL-methionine methylsulfonium chloride is a naturally occurring methionine derivative. DL-methionine methylsulfonium chloride protects gastric mucosal from ethanol-induced damage. | 3493-12-7 |
| HY-N6810 | Thymol | Bacterial | Anti-infection | Thymol is the main monoterpene phenol occurring in essential oils isolated from plants belonging to the Lamiaceae family, and other plants such as those belonging to the Verbenaceae, Scrophulariaceae, Ranunculaceae and Apiaceae families. Thymol has antioxidant, anti-inflammatory, antibacterial and antifungal effects. | 89-83-8 |
| HY-N6952 | Geraniol | Endogenous Metabolite; Fungal | Anti-infection; Metabolic Enzyme/Protease | Geraniol, an olefinic terpene, was found to inhibit growth of *Candida albicans* and *Saccharomyces cerevisiae* strains. | 106-24-1 |
| HY-N6996 | Methyl Eugenol | Others | Others | Methyl Eugenol, a phenylpropanoid chemical in leaves, fruits, stems, and/or roots, may be released when that corresponding part of a plant is damaged as a result of feeding by an herbivore. Methyl Eugenol is used for male annihilation of the oriental fruit fly. | 93-15-2 |

TABLE 1-continued

Illustrative additional ingredients

| Catalog No | Drug Names | Target | Pathway | Biological Activity | CAS |
|---|---|---|---|---|---|
| HY-N7000 | Perillyl alcohol | Apoptosis; Endogenous Metabolite | Apoptosis; Metabolic Enzyme/Protease | Perillyl alcohol is a monoterpene isolated from the essential oils of lavendin, peppermint, spearmint, cherries, celery seeds, and several other plants. Perillyl alcohol is active in inducing apoptosis in tumor cells without affecting normal cells. | 536-59-4 |
| HY-N7063 | Nerol | Apoptosis; Endogenous Metabolite; Fungal; Mitochondrial Metabolism; Reactive Oxygen Species | Anti-infection; Apoptosis; Immunology/Inflammation; Metabolic Enzyme/Protease; NF-κB | Nerol is a constituent of neroli oil. Nerol Nerol triggers mitochondrial dysfunction and induces apoptosis via elevation of Ca2+ and ROS. Antifungal activity. | 106-25-2 |
| HY-N7079 | Erythorbic acid | Others | Others | Erythorbic acid (D-Isoascorbic acid), produced from sugars derived from different sources, such as beets, sugar cane, and corn, is a food additive used predominantly in meats, poultry, and soft drinks. | 89-65-6 |
| HY-N7079A | Sodium erythorbate | Others | Others | Sodium erythorbate (D-Isoascorbic acid sodium), produced from sugars derived from different sources, such as beets, sugar cane, and corn, is a food additive used predominantly in meats, poultry, and soft drinks. | 6381-77-7 |
| HY-N7083 | Citral | Others | Others | Citral is a monoterpene found in Cymbopogon citratus essential oil, with antihyperalgesic, anti-nociceptive and anti-inflammatory effects. | 5392-40-5 |
| HY-N7090 | Benzyl cinnamate | | | | 57-48-7 |
| HY-N7092 | D-Fructose | Others | Others | D-Fructose (D(−)-Fructose) is a naturally occurring monosaccharide found in many plants. | 470-67-7 |
| HY-N7117 | 1,4-Cineole | Endogenous Metabolite; TRP Channel | Membrane Transporter/Ion Channel; Metabolic Enzyme/Protease; Neuronal Signaling | 1,4-Cineole is a widely distributed, natural, oxygenated monoterpene. 1,4-Cineole, present in eucalyptus oil, activates both human TRPM8 and human TRPA1. | |
| HY-N7124 | Benzyl acetate | Others | Others | Benzyl acetate is a constituent of jasmin and of the essential oils of ylang-ylang and neroli. Natural sources of Benzyl acetate include varieties of flowers like jasmine (Jasminum), and fruits like pear, apple. | 140-11-4 |
| HY-N7393 | Isomalt | Lactate Dehydrogenase | Metabolic Enzyme/Protease | Isomalt (Palatinitol), a well-tolerated, non-toxic polyol and a protein-stabilizing excipient, stabilizes lactate dehydrogenase (LDH) moderately during freeze-drying, and performs better during storage. Isomalt is traditionally used as a sweetening agent in the food industry and as a tabletting excipient for pharmaceutical purposes. | 64519-82-0 |
| HY-P1645 | Papain | Cathepsin | Metabolic Enzyme/Protease | Papain is a cysteine protease of the peptidase C1 family, which is used in food, pharmaceutical, textile, and cosmetic industries. | 9001-73-4 |
| HY-W001132 | Indole | Endogenous Metabolite | Metabolic Enzyme/Protease | Indole is an endogenous metabolite. | 120-72-9 |
| HY-W001245 | 4-Methylthiazole | | | | 693-95-8 |
| HY-W002045 | 1-(4-Methoxyphenyl) propan-2-one | | | | 122-84-9 |

TABLE 1-continued

Illustrative additional ingredients

| Catalog No | Drug Names | Target | Pathway | Biological Activity | CAS |
|---|---|---|---|---|---|
| HY-W002097 | 1-(5-Methylthiophen-2-yl)ethan-1-one | | | | 13679-74-8 |
| HY-W004058 | (Tetrahydrofuran-2-yl)methanol | | | | 97-99-4 |
| HY-W004282 | Undecanoic acid | Endogenous Metabolite; Fungal | Anti-infection; Metabolic Enzyme/Protease | Undecanoic acid (Undecanoate) is a monocarboxylic acid with antimycotic property, which inhibits the production of exocellular keratinase, lipase and the biosynthesis of several phospholipids in *T. rubrum*. | 112-37-8 |
| HY-W004283 | Pentadecanoic acid | Endogenous Metabolite | Metabolic Enzyme/Protease | Pentadecylic acid is a saturated fatty acid with a 15-carbon backbone. | 1002-84-2 |
| HY-W004292 | 1-Undecanol | Others | Others | 10-Undecen-1-ol, converted from ricinoleic acid, can be used as a comonomer for the introduction of functional groups. | 112-42-5 |
| HY-W004298 | 10-Undecen-1-ol | | | | 112-43-6 |
| HY-W004842 | Benzo[b]furan-2-carboxaldehyde | | | | 4265-16-1 |
| HY-W004975 | 5-Methylquinoxaline | | | | 13708-12-8 |
| HY-W005288 | 4-Vinylphenol | | | | 2628-17-3 |
| HY-W005344 | Ethyl 2-(2-methyl-1,3-dioxolan-2-yl)acetate | | | | 6413-10-1 |
| HY-W005513 | Benzo[b]furan-2-carboxaldehyde N,N-Bis(2-hydroxyethyl)dodecanamide | | | | 120-40-1 |
| HY-W006057 | 3-Methyl-2-oxobutanoic acid | Endogenous Metabolite | Metabolic Enzyme/Protease | 3-Methyl-2-oxobutanoic acid is a precursor of pantothenic acid in *Escherichia coli*. | 759-05-7 |
| HY-W007355 | Skatole | Aryl Hydrocarbon Receptor; Autophagy; Bacterial; Endogenous Metabolite; Fungal; p38 MAPK | Anti-infection; Autophagy; Immunology/Inflammation; MAPK/ERK Pathway; Metabolic Enzyme/Protease | Skatole is produced by intestinal bacteria, regulates intestinal epithelial cellular functions through activating aryl hydrocarbon receptors and p38. | 83-34-1 |
| HY-W007446 | 3-Phenylpropanal | | | | 104-53-0 |
| HY-W007606 | Tyramine | Endogenous Metabolite | Metabolic Enzyme/Protease | Tyramine is an amino acid that helps regulate blood pressure. Tyramine occurs naturally in the body, and it's found in certain foods. | 51-67-2 |
| HY-W007617 | Ethyl 3-oxo-3-phenylpropanoate | | | | 94-02-0 |
| HY-W007692 | Acetylpyrazine | Others | Others | Acetylpyrazine (2-Acetylpyrazine) is fused to form many polycyclic compounds, as useful structures in pharmaceuticals and perfumes. Acetylpyrazine is a component of the folates (vitamin B compounds). | 22047-25-2 |

TABLE 1-continued

Illustrative additional ingredients

| Catalog No | Drug Names | Target | Pathway | Biological Activity | CAS |
|---|---|---|---|---|---|
| HY-W007704 | Methyl cyclohexanecarboxylate | | | | 4630-82-4 |
| HY-W007828 | Methyl 3-phenylpropanoate | | | | 103-25-3 |
| HY-W007888 | 2-Hydroxy-4-methylbenzaldehyde | | | | 698-27-1 |
| HY-W007926 | 2-Oxobutanoic acid | Endogenous Metabolite | Metabolic Enzyme/Protease | 2-Oxobutanoic acid is a product in the enzymatic cleavage of cystathionine. | 600-18-0 |
| HY-W008270 | 2(5H)-Furanone | | | | 497-23-4 |
| HY-W008591 | 2-Methoxypyridine | | | | 1628-89-3 |
| HY-W009156 | Hydroxycitric acid (tripotassium hydrate) | | | | 6100-05-6 |
| HY-W009384 | 1,4-Dioxacyclohept adecane-5,17-dione | | | | 105-95-3 |
| HY-W009417 | Cedryl acetate | Glucosidase | Metabolic Enzyme/Protease | Cedryl acetate is a tricyclic sesquiterpene isolated from the plant Psidium caudatum. Cedryl acetate shows α-glucosidase inhibitory activity. | 77-54-3 |
| HY-W009516 | Dibenzyl disulfide | | | | 150-60-7 |
| HY-W009811 | Tridecan-2-one | | | | 593-08-8 |
| HY-W009948 | Vanillin acetate | Others | Others | Vanillin acetate is easily synthesized from vanillin by treatment with acetic anhydride. | 881-68-5 |
| HY-W010054 | 2-Ethoxynaphthalene | | | | 93-18-5 |
| HY-W010141 | 1-(4-Isopropylphenyl) ethanone | | | | 645-13-6 |
| HY-W010201 | Citronellol | Reactive Oxygen Species | Immunology/ Inflammation; Metabolic Enzyme/Protease; NF-κB | Citronellol ((±)-Citronellol) is a monoterpene Pelargonium capitatum. Citronellol ((±)-Citronellol) induces necroptosis of cancer cell via up-regulating TNF-α, RIP1/RIP3 activities, down-regulating caspase-3/caspase-8 activities and increasing ROS (reactive oxygen species) accumulation. | 106-22-9 |
| HY-W010293 | Ethyl 4-oxopentanoate | | | | 539-88-8 |
| HY-W010320 | Ethyl maltol | | Others | Ethyl maltol (2-Ethyl-3-hydroxy-4H-pyran-4-one), an odor-active (OA) compound, is an important food additive and the main component of a type of incense added to food. | 4940-11-8 |
| HY-W010392 | Ethyl 2-methylbutanoate | | | | 7452-79-1 |
| HY-W010435 | Sulcatone | | | | 110-93-0 |
| HY-W010476 | 2,3,5-Trimethylpyrazine | | | | 14667-55-1 |
| HY-W010483 | 2-Phenylethylamine | | | | 64-04-0 |
| HY-W010489 | 2-Phenylacetaldehyde | Endogenous Metabolite | Metabolic Enzyme/Protease | 2-Phenylacetaldehyde is an endogenous metabolite. | 122-78-1 |

TABLE 1-continued

Illustrative additional ingredients

| Catalog No | Drug Names | Target | Pathway | Biological Activity | CAS |
|---|---|---|---|---|---|
| HY-W010531 | trans-Hex-2-enoic acid | | | | 13419-69-7 |
| HY-W010533A | 2-Methyl-2-pentenoic acid | | | | 3142-72-1 |
| HY-W010540 | 4,5-Dimethylthiazole | | | | 3581-91-7 |
| HY-W010542 | Azepan-2-one | | | | 105-60-2 |
| HY-W010553 | 2,5-Dimethyl-3(2H)-furnone | Others | Others | 2,5-Dimethyl-3(2H)-furanone is a flavouring substance without genotoxicity. | 14400-67-0 |
| HY-W010562 | 2-Methoxypyrazine | | | | |
| HY-W010594 | Tetrahydrothiophen-3-one | Endogenous Metabolite | Metabolic Enzyme/Protease | Tetrahydrothiophen-3-one is an endogenous metabolite. | 1003-04-9 |
| HY-W010607 | cis-3-Hexen-1-ol | Others | Others | cis-3-Hexen-1-ol ((Z)-3-Hexen-1-ol) is a green grassy smelling compound found in many fresh fruits and vegetables. cis-3-Hexen-1-ol is widely used as an added flavor in processed food to provide a fresh green quality. cis-3-Hexen-1-ol is an attractant to various insects. | 928-96-1 |
| HY-W010611 | 3-Methylbut-2-enoic acid | Endogenous Metabolite | Metabolic Enzyme/Protease | 3-Methylbut-2-enoic acid is an endogenous metabolite. | 541-47-9 |
| HY-W010627 | 2,5-Dimethyl-1H-pyrrole | | | | 14400-67-0 |
| HY-W010970 | 5-Guanylic acid (disodium salt) | Endogenous Metabolite | Metabolic Enzyme/Protease | 5'-Guanylic acid disodium salt (5'-GMP disodium salt) is composed of guanine, ribose, and phosphate moieties and it is a nucleotide monomer in messenger RNA. Guanosine derivatives are involved in intracellular signal transduction and have been identified in repetitive genomic sequences in telomeres, in ribosomal DNA, immunoglobulin heavy-chain switch regions, and in the control regions of proto-oncogenes. | 5550-12-9 |
| HY-W011053 | Neotame | | | | 165450-17-9 |
| HY-W011678 | Octadecan-1-amine | | | | 124-30-1 |
| HY-W012499 | N-Acetyl-L-methionine | Endogenous Metabolite | Metabolic Enzyme/Protease | N-Acetyl-L-methionine, a human metabolite, is nutritionally and metabolically equivalent to L-methionine. L-methionine is an indispensable amino acid required for normal growth and development. | 65-82-7 |
| HY-W012530 | 2-Oxo-3-phenylpropanoic acid | Endogenous Metabolite | Metabolic Enzyme/Protease | 2-Oxo-3-phenylpropanoic acid is used in the synthesis of 3-phenyllactic acid (PLA) by lactate dehydrogenase. | 156-06-9 |
| HY-W012556 | Ethyl 3-hydroxyhexanoate | | | | 2305-25-1 |
| HY-W012575 | 2,4-Dihydroxybenzoic acid | Endogenous Metabolite | Metabolic Enzyme/Protease | 2,4-Dihydroxybenzoic acid is a degradation product of cyaniding glycoside from tart cherries in cell culture. | 89-86-1 |
| HY-W012595 | Benzylideneacetone | | | | 122-57-6 |
| HY-W012634 | Benzo[d]thiazole | | | | 95-16-9 |
| HY-W012653 | 4-Methylacetophenone | | | | 122-00-9 |
| HY-W012657 | 4-Ethylbenzaldehyde | | | | 4748-78-1 |
| HY-W012658 | 2-Methylacetophenone | Endogenous Metabolite | Metabolic Enzyme/Protease | 2-Methylacetophenone is an endogenous metabolite. | 577-16-2 |

TABLE 1-continued

Illustrative additional ingredients

| Catalog No | Drug Names | Target | Pathway | Biological Activity | CAS |
|---|---|---|---|---|---|
| HY-W012701 | Ethyl 3-hydroxybutyrate | | | | 5405-41-4 |
| HY-W012722 | 4-Methyl-2-oxopentanoic acid | Endogenous Metabolite | Metabolic Enzyme/Protease | 4-Methyl-2-oxopentanoic acid, an abnormal metabolite, is both a neurotoxin and a metabotoxin. | 816-66-0 |
| HY-W012732 | Isoquinoline | | | | 118-71-8 |
| HY-W012788 | Maltol | Endogenous Metabolite | Metabolic Enzyme/Protease | Maltol, a type of aromatic compound, exists in high concentrations in red ginseng. Maltol is a potent antioxidative agent and typically is used to enhance flavor and preserve food. | 1193-79-9 |
| HY-W012813 | 1-(5-Methylfurnn-2-yl)ethanone | | | | 1192-62-7 |
| HY-W012836 | 4-Ethylphenol | Endogenous Metabolite | Metabolic Enzyme/Protease | 4-Ethylphenol is a volatile phenolic compound associated with off-odour in wine. | 123-07-9 |
| HY-W012889 | DL-Valine | | | | 516-06-3 |
| HY-W012956 | 1-(1H-Pyrrol-2-yl)ethanone | | | | 1072-83-9 |
| HY-W012980 | 3-Methylbutanoic acid | Endogenous Metabolite | Metabolic Enzyme/Protease | 3-Methylbutanoic acid is a natural fatty acid and known to effect on neonatal death and possible Jamaican vomiting sickness in human. | 503-74-2 |
| HY-W012995 | 5-Hexen-1-ol | | | | 821-41-0 |
| HY-W012999 | Tiglic acid | Endogenous Metabolite | Metabolic Enzyme/Protease | Tiglic acid is a monocarboxylic unsaturated organic acid found in croton oil and in several other natural products. Tiglic aci has a role as a plant metabolite. | 80-59-1 |
| HY-W013014 | 3-Methyl-2-cyclopenten-1-one | Endogenous Metabolite | Metabolic Enzyme/Protease | 3-Methyl-2-cyclopenten-1-one is an endogenous metabolite. | 2758-18-1 |
| HY-W013035 | 3-Methyl-2-buten-1-ol | Endogenous Metabolite | Metabolic Enzyme/Protease | 3-Methyl-2-buten-1-ol is an endogenous metabolite. | 556-82-1 |
| HY-W013040 | Pyrazine | | | | 290-37-9 |
| HY-W013573 | S-Allyl-L-cysteine | Apoptosis | Apoptosis | S-Allyl-L-cysteine, one of the organosulfur compounds found in AGE, possess various biological effects including neurotrophic activity, anti-cancer activity, anti-inflammatory activity. | 21593-77-1 |
| HY-W013627 | (2E,4E)-Deca-2,4-dienal | | | | 25152-84-5 |
| HY-W013636 | 2-Ketoglutaric acid | Endogenous Metabolite; Tyrosinase | Metabolic Enzyme/Protease | 2-Ketoglutaric acid (Alpha-Ketoglutaric acid) is an intermediate in the production of ATP or GTP in the Krebs cycle. 2-Ketoglutaric acid also acts as the major carbon skeleton for nitrogen-assimilatory reactions. 2-Ketoglutaric acid is a reversible inhibitor of tyrosinase (IC50 = 15 mM). | 328-50-7 |
| HY-W013807 | Dibutyl sebacate | Others | Others | Dibutyl sebacate (Dibutyl decanedioate) is a dibutyl ester of sebacic acid, mainly used as a plasticizer in production of plastics. | 109-43-3 |
| HY-W014102 | L-Alanyl-L-glutamine | Endogenous Metabolite | Metabolic Enzyme/Protease | L-Alanyl-L-glutamine, a glutamine dipeptide, is benefit for the antioxidant system, attenuating inflammation, and may modulate the heat shock protein (HSP) response in catabolic situations. | 39537-23-0 |

TABLE 1-continued

Illustrative additional ingredients

| Catalog No | Drug Names | Target | Pathway | Biological Activity | CAS |
|---|---|---|---|---|---|
| HY-W014207 | Ethyl undecanoate | | | | 627-90-7 |
| HY-W014325 | TRPM8 antagonist WS-3 | TRP Channel | Membrane Transporter/Ion Channel; Neuronal Signaling | TRPM8 antagonist WS-3 is an agonist of TRPM8 with an EC50 of 3.7 µM. | 39711-79-0 |
| HY-W014388 | 1,3-Diphenylpropan-2-one | | | | 102-04-5 |
| HY-W015301 | Dimethyl adipate | | | | 627-93-0 |
| HY-W015309 | Decanoic acid | Endogenous Metabolite | Metabolic Enzyme/Protease | Decanoic acid belongs to the class of organic compounds known as medium-chain fatty acids. | 334-48-5 |
| HY-W015342 | Methyl anisate | | | | 121-98-2 |
| HY-W015371 | Ethyl phenylacetate | | | | 101-97-3 |
| HY-W015410 | Disodium succinate | Others | Others | Disodium succinate is the disodium salt of Succinic acid. Succinic acid is an intermediate product of the tricarboxylic acid cycle, as well as one of fermentation products of anaerobic metabolism. | 150-90-3 |
| HY-W015611 | L-(+)-Arabinose | Endogenous Metabolite | Metabolic Enzyme/Protease | L-(+)-Arabinose selectively inhibits intestinal sucrase activity in a noncompetitive manner and suppresses the plasma glucose increase due to sucrose ingestion. | 5328-37-0 |
| HY-W015618 | 2,4'-Dimethylacetophenone | | | | 89-74-7 |
| HY-W015695 | 4-Methyl-5-thiazoleethanol | | | | 137-00-8 |
| HY-W015709 | Ethyl hex-3-enoate | | | | 2396-83-0 |
| HY-W015777 | (4-Methoxyphenyl)methanol | | | | 105-13-5 |
| HY-W015780 | 1,4-Dimethoxybenzene | | | | 150-78-7 |
| HY-W015786 | 4-Ethoxyphenol | | | | 622-62-8 |
| HY-W015820 | Isobenzofuran-1(3H)-one | | | | 87-41-2 |
| HY-W015861 | p-Tolylmethanol | | | | 589-18-4 |
| HY-W015883 | Fumaric acid | Endogenous Metabolite | Metabolic Enzyme/Protease | Fumaric acid, associated with fumarase deficiency, is identified as an oncometabolite or an endogenous, cancer causing metabolite. | 110-17-8 |
| HY-W016081 | Allyl cinnamate | | | | 1866-31-5 |
| HY-W016089 | Ethyl 2-(2,4-dimethyl-1,3-dioxolan-2-yl)acetate | | | | 6290-17-1 |
| HY-W016319 | (S)-2-aminopentanedioic acid hydrochloride | | | | 138-15-8 |

TABLE 1-continued

Illustrative additional ingredients

| Catalog No | Drug Names | Target | Pathway | Biological Activity | CAS |
|---|---|---|---|---|---|
| HY-W016610 | 2-Ethoxy-5-propenylphenol | | | | 94-86-0 |
| HY-W016806 | Sodium 4-(methoxycarbonyl)phenolate | | | | |
| HY-W016976 | Allyl heptanoate | | | | 142-19-8 |
| HY-W017018 | L-Ornithine (hydrochloride) | Endogenous Metabolite | Metabolic Enzyme/Protease | L-Ornithine hydrochloride is a free amino acid that plays a central role in the urea cycle and is also important for the disposal of excess nitrogen. | 3184-13-2 |
| HY-W017077 | 4-Methylbiphenyl | Endogenous Metabolite | Metabolic Enzyme/Protease | 4-Methylbiphenyl is an endogenous metabolite. | 644-08-6 |
| HY-W017140 | 2-(sec-Butyl)-3-methoxypyrazine | | | | 24168-70-5 |
| HY-W017141 | 2-Isobutyl-3-methoxypyrazine | | | | 24683-00-9 |
| HY-W017212 | Methyl cinnamate | AMPK; Bacterial; Tyrosinase | Anti-infection; Epigenetics; Metabolic Enzyme/Protease; PI3K/Akt/mTOR | Methyl cinnamate (Methyl 3-phenylpropenoate), an active component of Zanthoxylum armatum, is a widely used natural flavor compound. Methyl cinnamate (Methyl 3-phenylpropenoate) possesses antimicrobial activity and is a tyrosinase inhibitor that can prevent food browning. Methyl cinnamate (Methyl 3-phenylpropenoate) has antiadipogenic activity through mechanisms mediated, in part, by the CaMKK2-AMPK signaling pathway. | 103-26-4 |
| HY-W017232 | 6-Methoxyquinoline | | | | 5263-87-6 |
| HY-W017278 | 2-((Isopropylthio)methyl)furan | | | | 1883-78-9 |
| HY-W017316 | Terpinen-4-ol | Endogenous Metabolite | Metabolic Enzyme/Protease | Terpinen-4-ol (4-Carvomenthenol), a naturally occurring monoterpene, is the main bioactive component of tea-tree oil. Terpinen-4-ol suppresses inflammatory mediator production by activated human monocytes. Terpinen-4-ol significantly enhances the effect of several chemotherapeutic and biological agents. | 562-74-3 |
| HY-W017370 | Carveol | | | | 99-48-9 |
| HY-W017371 | p-Dithiane-2,5-diol | | | | 40018-26-6 |
| HY-W017374 | 4-Ethyl-2-methoxyphenol | | | | 2785-89-9 |
| HY-W017428 | 4-Ethoxybenzaldehyde | | | | 10031-82-0 |
| HY-W017522 | Adipic acid | Endogenous Metabolite | Metabolic Enzyme/Protease | Adipic acid is found to be associated with HMG-CoA lyase deficiency, carnitine-acylcarnitine translocase deficiency, malonyl-Coa decarboxylase deficiency, and medium Chain acyl-CoA dehydrogenase deficiency, which are inborn errors of metabolism. | 124-04-9 |
| HY-W017562 | 5-Butyldihydrofuran-2(3H)-one | | | | 104-50-7 |
| HY-W017592 | 2-(Methylthio)phenol | | | | 1073-29-6 |

TABLE 1-continued

Illustrative additional ingredients

| Catalog No | Drug Names | Target | Pathway | Biological Activity | CAS |
|---|---|---|---|---|---|
| HY-W017611 | 4-Propylphenol | | | | 645-56-7 |
| HY-W017613 | 2-(Ethoxymethyl)benzene | | | | 539-30-0 |
| HY-W018501 | Methyl p-tert-butylphenylacetate | | | | 3549-23-3 |
| HY-W018653 | Cyclohexaneacetic acid | | | | 5292-21-7 |
| HY-W018758 | 1-Phenylpropane-1,2-dione | Others | Others | 1-Phenylpropane-1,2-dione, isolated from young Ephedra sinica Stapf (Ephedraceae), is biosynthetic precursors of the ephedrine alkaloids. | 579-07-7 |
| HY-W018772 | D-Ribose(mixture of isomers) | Endogenous Metabolite | Metabolic Enzyme/Protease | D-Ribose(mixture of isomers) is an energy enhancer, and acts as a sugar moiety of ATP, and widely used as a metabolic therapy supplement for chronic fatigue syndrome or cardiac energy metabolism. D-Ribose(mixture of isomers) is active in protein glycation, induces NF-κB inflammation in a RAGE-dependent manner. | 50-69-1 |
| HY-W019711 | trans-Cinnamaldehyde | Endogenous Metabolite | Metabolic Enzyme/Protease | trans-Cinnamaldehyde can be used to prepare highly polyfunctionalized furan ring by reaction of alkyl isocyanides with dialkyl acetylenedicalboxylate. trans-Cinnamaldehyde can be used to synthesize trans-cinnamaldehyde-β-cyclodextrin complex, an antimicrobial edible coating that increases the shelf life of fresh-cut fruits. | 14371-10-9 |
| HY-W019894 | Manganese dichloride | | | | 7773-01-5 |
| HY-W019901 | Anhydrous calcium sulfate | | | | 7778-18-9 |
| HY-W020014 | Pyruvic aldehyde | | | | 78-98-8 |
| HY-W026742 | Ethyl anthranilate | | | | 87-25-2 |
| HY-W027751 | 2-Methylanisole | | | | 578-58-5 |
| HY-W027872 | Piperonyl acetone | | | | 55418-52-5 |
| HY-W032013 | 1-Octanol | Calcium Channel; Endogenous Metabolite | Membrane Transporter/Ion Channel; Metabolic Enzyme/Protease; Neuronal Signaling | 1-Octanol (Octanol), a saturated fatty alcohol, is a T-type calcium channels (T-channels) inhibitor with an IC50 of 4 μM for native T-currents. 1-Octanol is a highly attractive biofuel with diesel-like properties. | 111-87-5 |
| HY-W035362 | Cyclopentadecanolide | | | | 106-02-5 |
| HY-W038287 | 2-Methylbenzoxazole | | | | 95-21-6 |
| HY-W039157 | 2-Acetyl-3-ethylpyrazine | | | | 32974-92-8 |
| HY-W039718 | 1-(2,4-Dimethylthiazol-5-yl)ethan-1-one | | | | 38205-60-6 |

TABLE 1-continued

Illustrative additional ingredients

| Catalog No | Drug Names | Target | Pathway | Biological Activity | CAS |
|---|---|---|---|---|---|
| HY-W040226 | Indigo carmine | Others | Others | Indigo carmine is an efficient reagent for the determination of ozone by chemlluminescence (CL). | 860-22-0 |
| HY-W040240 | (3S,4R,5S)-1,3,4,5,6-Pentahydroxyhexan-2-one | Endogenous Metabolite | Metabolic Enzyme/Protease | (3S,4R,5S)-1,3,4,5,6-Pentahydroxyhexan-2-one is an endogenous metabolite. | 87-79-6 |
| HY-W040790 | 2,6-Dimethylpymzine | | | | 108-50-9 |
| HY-W040948 | 2-Ethylpyrazine | | | | 13925-00-3 |
| HY-W040971 | Creosol | Endogenous Metabolite | Metabolic Enzyme/Protease | Creosol is an endogenous metabolite. | 93-51-6 |
| HY-W041301 | 4,4,7a-Trimethyl-5,6,7,7a-tetrnhydrobenzo furan-2(4H)-one | | | | 15356-74-8 |
| HY-W041470 | 4-Methyl-1-phenyl-2-pentanone | | | | 5349-62-2 |
| HY-W041533 | 5,6,7,8-Tetrahydroquin oxaline | | | | 34413-35-9 |
| HY-W041912 | Ethyl 2-benzylidene-3-oxobutanoate | | | | 620-80-4 |
| HY-W052009 | Methyl 2-hydroxyethyl cellulose | | | | |
| HY-W067358 | 2-Methylpymzine | | | | 109-08-0 |
| HY-W067695 | Octahydro-2H-chromen-2-one | | | | 4430-31-3 |
| HY-W086991 | 3-Methyl-2-cyclohexenone | | | | 1193-18-6 |
| HY-W087045 | Benzyl formate | | | | 104-57-4 |
| HY-W087922 | Tridodecylamine | | | | 102-87-4 |
| HY-W087943 | Methyl octanoate | | | | 111-11-5 |
| HY-W087984 | Heptane-1-thiol | | | | 1639-09-4 |
| HY-W087985 | Isopentyl isobutyrmte | | | | 2050-01-3 |
| HY-W087987 | 2-Pentylthiophene | | | | 4861-58-9 |
| HY-W088065 | Sodium formate | | | | 141-53-7 |
| HY-W088319 | Butyrnnide | | | | 541-35-5 |
| HY-W088425 | Methyl 3-(methylthio) propanoate | | | | 13532-18-8 |

TABLE 1-continued

Illustrative additional ingredients

| Catalog No | Drug Names | Target | Pathway | Biological Activity | CAS |
|---|---|---|---|---|---|
| HY-W088436 | 1-(1-Methyl-1H-pyrrol-2-yl)ethan-1-one | Others | Others | | 932-16-1 |
| HY-Y0016 | Rhodamine B | | | Rhodamine B is a staining fluorescent dye, commonly used for dyeing textiles, paper, soap, leather, and drugs. | 81-88-9 |
| HY-Y0035 | 4,4-Dimethoxy-2-butanone | | | | 5436-21-5 |
| HY-Y0045 | 2-Acetylthiazole | | | | 24295-03-2 |
| HY-Y0073 | 4-Hydroxyacetophenone | HBV | Anti-infection | 4-Hydroxyacetophenone (P-hydroxyacetophenone) is a key hepatoprotective and choleretic compound in *Artemisia capillaris* and *A. morrisonensis*, also has an anti-hepatitis B virus effect and anti-inflammatory effect. | 99-93-4 |
| HY-Y0078 | Cinnamyl Alcohol | PPAR | Cell Cycle/DNA Damage | Cinnamyl Alcohol is an active component from chestnut flower, inhibits increased PPARγ expression, with anti-obesity activity. | 104-54-1 |
| HY-Y0110 | 2-Naphthol | Endogenous Metabolite | Metabolic Enzyme/Protease | 2-Naphthol is a metabolite of naphthalene, catalyzed by cytochrome P450 (CYP) isozymes (CYP 1A1, CYP 1A2, CYP 2A1, CYP 2E1 and CYP 2F2). | 135-19-3 |
| HY-Y0121 | SemaSORB 9827 | | | | 103-36-6 |
| HY-Y0172 | Butylated hydroxytoluene | Ferroptosis | Apoptosis | Butylated hydroxytoluene is an antioxidant widely used in foods and in food-related products. Butylated hydroxytoluene is a Ferroptosis inhibitor. | 128-37-0 |
| HY-Y0189 | Methyl Salicylate | COX | Immunology/Inflammation | Methyl Salicylate (Wintergreen oil) is a topical analgesic and anti-inflammatory agent. Also used as a pesticide, a denaturant, a fragrance ingredient, and a flavoring agent in food and tobacco products. A systemic acquired resistance (SAR) signal in tobacco. A topical nonsteroidal anti-inflammatory drug (NSAID). Methyl salicylate lactoside is a COX inhibitor. | 119-36-8 |
| HY-Y0190 | (2R,3R)-Diethyl 2,3-dihydroxy succinate | | | | 87-91-2 |
| HY-Y0248A | Farnesol | Antibiotic; Bacterial; Endogenous Metabolite | Anti-infection; Metabolic Enzyme/Protease | Farnesol is a sesquiterpene alcohol that modulates cell-to-cell communication in Candida albicans, and has the activity in inhibiting bacteria. | 4602-84-0 |
| HY-Y0252 | L-Proline | Endogenous Metabolite | Metabolic Enzyme/Protease | L-Proline is one of the twenty amino acids used in living organisms as the building blocks of proteins. | 147-85-3 |
| HY-Y0264 | 4-Hydroxybenzoic acid | Bacterial; Endogenous Metabolite | Anti-infection; Metabolic Enzyme/Protease | 4-Hydroxybenzoic acid, a phenolic derivative of benzoic acid, could inhibit most gram-positive and some gram-negative bacteria, with an IC50 of 160 μg/mL. | 99-96-7 |
| HY-Y0267 | Phenoxyacetic acid | Endogenous Metabolite | Metabolic Enzyme/Protease | Phenoxyacetic acid is an endogenous metabolite. | 122-59-8 |
| HY-Y0271 | Urea | Endogenous Metabolite | Metabolic Enzyme/Protease | Urea is a powerful protein denaturant via both direct and indirect mechanisms. A potent emollient and keratolytic agent. Used as a diuretic agent. Blood urea nitrogen (BUN) has been utilized to evaluate renal function. Widely used in fertilizers as a source of nitrogen and is an important raw material for the chemical industry. | 57-13-6 |

TABLE 1-continued

Illustrative additional ingredients

| Catalog No | Drug Names | Target | Pathway | Biological Activity | CAS |
|---|---|---|---|---|---|
| HY-Y0272 | Saccharin | Bacterial | Anti-infection | Saccharin is an orally active, non-caloric artificial sweeteners (NAS). Saccharin has bacteriostatic and microbiome-modulating properties. | 81-07-2 |
| HY-Y0283 | Antistrumin | | | | 7681-11-0 |
| HY-Y0284 | Diethylphthalate | | | | 84-66-2 |
| HY-Y0287 | Carbonate (calcium) | | | | 471-34-1 |
| HY-Y0289 | 1-Dodecanol | | | | 112-53-8 |
| HY-Y0293 | L-Tartaric acid | Endogenous Metabolite | Metabolic Enzyme/Protease | L-Tartaric acid (L-(+)-Tartaric acid) is an endogenous metabolite. | 87-69-4 |
| HY-Y0308 | Hydrogen disodium phosphate | | | | 7558-79-4 |
| HY-Y0313 | p-Hydroxybenzaldehyde | Endogenous Metabolite; GABA Receptor | Membrane Transporter/Ion Channel; Metabolic Enzyme/Protease; Neuronal Signaling | p-Hydroxybenzaldehyde is a one of the major components in Dendrocalamus asper bamboo shoots, with antagonistic effect on GABAA receptor of the α1β2γ2S subtype at high concentrations. | 123-08-0 |
| HY-Y0316 | Sodium dodecyl sulfate | | | | 151-21-3 |
| HY-Y0319B | Acetic acid (potassium) | | | | 127-08-2 |
| HY-Y0337 | L-Cysteine | Endogenous Metabolite; Ferroptosis | Apoptosis; Metabolic Enzyme/Protease | L-Cysteine is a thiol-containing non-essential amino acid that is oxidized to form cystine. | 52-90-4 |
| HY-Y0337A | L-Cysteine (hydrochloride) | Endogenous Metabolite | Metabolic Enzyme/Protease | L-Cysteine hydrochloride is a conditionally essential amino acid, which acts as a precursor for biologically active molecules such as hydrogen sulphide (H2S), glutathione and taurine. L-Cysteine hydrochloride suppresses ghrelin and reduces appetite in rodents and humans | 52-89-1 |
| HY-Y0344 | Sodium chloride | | | | 7647-14-5 |
| HY-Y0366 | Lauric acid | Bacterial; Endogenous Metabolite | Anti-infection; Metabolic Enzyme/Protease | Lauric acid is a middle chain-free fatty acid with strong bactericidal properties. The EC50s for *P. acnes*, *S. aureus*, *S. epidermidis*, are 2, 6, 4 μg/mL, respectively. | 143-07-7 |
| HY-Y0367 | Maleic Acid | Bacterial; Endogenous Metabolite | Anti-infection; Metabolic Enzyme/Protease | Maleic Acid is a Glutamate Decarboxylase (GAD) inhibitor of *E. coli* and *L. monocytogenes*. | 110-16-7 |
| HY-Y0479 | L-Lactic acid | Antibiotic; Bacterial; Endogenous Metabolite | Anti-infection; Metabolic Enzyme/Protease | L-Lactic acid is a building block which can be used as a precursor for the production of the bioplastic polymer poly-lactic acid. | 79-33-4 |
| HY-Y0481A | Stannous dichloride (dihydrate) | | | | |
| HY-Y0498 | Aluminum oxide | | | | |
| HY-Y0537 | Potassium chloride | | | | 7447-40-7 |

TABLE 1-continued

Illustrative additional ingredients

| Catalog No | Drug Names | Target | Pathway | Biological Activity | CAS |
|---|---|---|---|---|---|
| HY-Y0543 | 5-Methylfurfural | Others | Others | 5-Methylfurfural is a naturally occurring substance, found in cigarette smoke condensate, licorice essential oil, stored dehydrated orange powder, baked potato flour, volatile compounds of roast beef, aroma concentrate of sponge cake, bread and in coffee, tea and cocoa. A flavoring agent. | 620-02-0 |
| HY-Y0546 | Benzophenone | | | | 119-61-9 |
| HY-Y0569 | D-Gluconic acid | Endogenous Metabolite | Metabolic Enzyme/Protease | D-Gluconic acid is the carboxylic acid by the oxidation with antiseptic and chelating properties. | 526-95-4 |
| HY-Y0600 | Thioanisole | | | | 100-68-5 |
| HY-Y0624 | 4-Pentenoic acid | | | | 591-80-0 |
| HY-Y0682 | Ethylenediamin etetraacetic acid | | | | |
| HY-Y0682A | Ethylenediamin etetraacetic acid disodium salt dihydrate | | | | 6381-92-6 |
| HY-Y0703 | Sodium carboxymethyl cellulose (Viscosity:800-1200 mPa.S) | Others | Others | Sodium carboxymethyl cellulose (Viscosity:800-1200 mPa.S) is the sodium salt of cellulose arboxymethyl and frequently used as viscous agent, paste and barrier agent. | 9004-32-4 |
| HY-Y0708 | Calcium hydrogen phosphate dihydrate | | | | |
| HY-Y0740 | 4-Methoxybenzaldehyde | Endogenous Metabolite | Metabolic Enzyme/Protease | 4-Methoxybenzaldehyde is a naturally occurring fragrant phenolic compound that is soluble in acetone. 4-Methoxybenzaldehyde has been found in many plant species including horseradish, anise, star anise. 4-Methoxybenzaldehyde is a possible neurotoxicant and it has shown effects that include mortality, attractancy, and interference with host seeking. | 123-11-5 |
| HY-Y0743 | 1-(Pyridin-2-yl)ethan-1-one | | | | 1122-62-9 |
| HY-Y0751 | 1-(Pyridin-3-yl)ethanone | | | | 350-03-8 |
| HY-Y0756 | Carbonic acid monosodium salt | | | | 144-55-8 |
| HY-Y0760 | 3-Methoxybenzoic acid | Endogenous Metabolite | Metabolic Enzyme/Protease | 3-Methoxybenzoic acid can be used in the synthesis of 3-methoxybenzoates of europium (III) and gadolinium (III). | 586-38-9 |
| HY-Y0781 | Pyruvic acid | Endogenous Metabolite | Metabolic Enzyme/Protease | Pyruvic acid is an intermediate metabolite in the metabolism of carbohydrates, proteins, and fats. | 127-17-3 |
| HY-Y0790 | Cuminaldehyde | Endogenous Metabolite | Metabolic Enzyme/Protease | Cuminaldehyde is the major component of Cuminum cyminum, a natural aldehyde with inhibitory effect on alpha-synuclein fibrillation and cytotoxicity. Cuminaldehyde shows anticancer activity. | 122-03-2 |

TABLE 1-continued

Illustrative additional ingredients

| Catalog No | Drug Names | Target | Pathway | Biological Activity | CAS |
|---|---|---|---|---|---|
| HY-Y0808 | Dimethyl succinate | | | | 106-65-0 |
| HY-Y0813 | Iron | | | | 7439-89-6 |
| HY-Y0836 | Diethyl succinate | Others | Others | Diethyl succinate (Diethyl Butanedioate) is used at physiological pH and crosses biological membranes, incorporates into cells in tissue culture and is metabolized by the TCA cycle. Diethyl succinate is known to be non-toxic and used in fragrances and flavoring. | 123-25-1 |
| HY-Y0839 | Levulinic acid | Endogenous Metabolite | Metabolic Enzyme/Protease | Levulinic acid is a precursor for the synthesis of biofuels, such as ethyl levulinate. | 123-76-2 |
| HY-Y0873 | PEG300 | Others | Others | PEG300 (Polyethylene glycol 300), a neutral polymer of molecular weight 300, is a water-soluble, low immunogenic and biocompatible polymer formed by repeating units of ethylene glycol. | 25322-68-3 |
| HY-Y0892 | 4-Hydroxybenzyl alcohol | Apoptosis; Endogenous Metabolite | Apoptosis; Metabolic Enzyme/Protease | 4-Hydroxybenzyl alcohol is a phenolic compound widely distributed in various kinds of plants. Anti-inflammatory, anti-oxidant, anti-nociceptive activity. Neuroprotective effect. Inhibitor of tumor angiogenesis and growth | 623-05-2 |
| HY-Y0921 | (±)-1,2-Propanediol | Others | Others | (±)-1,2-Propanediol is an aliphatic alcohol and frequently used as an excipient in many drug formulations to increase the solubility and stability of drugs. | 57-55-6 |
| HY-Y0932 | Isophorone | | | | 78-59-1 |
| HY-Y0946 | Acetamide | Endogenous Metabolite | Metabolic Enzyme/Protease | Acetamide is used primarily as a solvent and a plasticizer. | 60-35-5 |
| HY-Y0949 | Methyl 2-furoate | Endogenous Metabolite | Metabolic Enzyme/Protease | Methyl 2-furoate (Methyl furan-2-carboxylate) is a building block in chemical synthesis. A flavoring agent in food. Found in cranberries, guava fruits, raisins and other fruits. Also present in baked potato, roasted filberts, roasted peanut, tomatoes, coffee, cocoa, okra, etc. | 611-13-2 |
| HY-Y0961 | Copper(I) iodide | | | | 7681-65-4 |
| HY-Y0966 | Glycine | Endogenous Metabolite; iGluR | Membrane Transporter/Ion Channel; Metabolic Enzyme/Protease; Neuronal Signaling | Glycine is an inhibitory neurotransmitter in the CNS and also acts as a co-agonist along with glutamate, facilitating an excitatory potential at the glutaminergic N-methyl-D-aspartic acid (NMDA) receptors. | 56-40-6 |
| HY-Y0989 | Acetophenone | | | | 98-86-2 |
| HY-Y1011 | 2-Ethylhexan-1-ol | | | | |
| HY-Y1069 | (S)-2-Hydroxysuccinic acid | Endogenous Metabolite | Metabolic Enzyme/Protease | (S)-2-Hydroxysuccinic acid is a dicarboxylic acid in naturally occurring form, contributes to the pleasantly sour taste of fruits and is used as a food additive. | 97-67-6 |
| HY-Y1088 | Hydrocinnamic acid | Endogenous Metabolite | Metabolic Enzyme/Protease | Hydrocinnamic acid is the major rhizospheric compound with known growth regulatory activities. | 501-52-0 |
| HY-Y1093 | Ethyl acetoacetate | | | | 141-97-9 |
| HY-Y1103 | Iron(II) sulfate heptahydrate | | | | 7782-63-0 |
| HY-Y1116 | Magnesium oxide | | | | 1309-48-4 |

TABLE 1-continued

Illustrative additional ingredients

| Catalog No | Drug Names | Target | Pathway | Biological Activity | CAS |
|---|---|---|---|---|---|
| HY-Y1177 | Diphenyl disulfide | | | | 882-33-7 |
| HY-Y1220 | Dipotassium carbonate | | | | 584-08-7 |
| HY-Y1311 | Malic acid | Endogenous Metabolite | Metabolic Enzyme/Protease | Malic acid is a dicarboxylic acid that is naturally found in fruits such as apples and pears. It plays a role in many sour or tart foods. | 6915-15-7 |
| HY-Y1316 | Sodium benzoate | | | | 532-32-1 |
| HY-Y1362 | Ethyl pyruvate | | | | 617-35-6 |
| HY-Y1366 | Hydroxyacetone | | | | 116-09-6 |
| HY-Y1373 | Cyclohexanecarboxylic acid | Endogenous Metabolite | Metabolic Enzyme/Protease | Cyclohexanecarboxylic acid is a Valproate structural analogue with anticonvulsant action. | 98-89-5 |
| HY-Y1426 | 2-Hydroxyacetophenone | Others | Others | 2′-Hydroxyacetophenone is found in alcoholic beverages. 2′-Hydroxyacetophenone is present in tomato, cassia, fried beef, rum, whiskey, cocoa, coffee and black tea. 2′-Hydroxyacetophenone is a flavouring ingredient. Building block in chemical synthesis. | 118-93-4 |
| HY-Y1673 | Potassium bromide | | | | 7758-02-3 |
| HY-Y1683 | DL-Menthol | GABA Receptor | Membrane Transporter/Ion Channel; Neuronal Signaling | DL-Menthol is a relative configuration of (−)-Menthol. DL-Menthol induces surgical anesthesia for fish that relates to the activation of GABAA receptor. | 89-78-1 |
| HY-Y1718 | NSC 25955 | Endogenous Metabolite | Metabolic Enzyme/Protease | NSC 25955 is an endogenous metabolite. | 638-53-9 |
| HY-Y1809 | 1-Hydroxyoctadecane | Endogenous Metabolite | Metabolic Enzyme/Protease | 1-Hydroxyoctadecane is an endogenous metabolite. | 112-92-5 |
| HY-Y1829 | Hydratropaldehyde | | | | 93-53-8 |
| HY-Y1878 | Copper sulfate | | | | 7758-98-7 |
| HY-Y1879 | Manganese sulfate | | | | 7785-87-7 |
| HY-Y1880 | Carbonic acid sodium salt, hydrate | | | | |
| HY-Y1883 | Hydrol SW | | | | 9002-93-1 |
| HY-Y1885 | Tetrasodium pyrophosphate | | | | 7722-88-5 |
| HY-Y1888 | Corn oil | Others | Others | Corn oil, extracted from the germ of corn, can be used as a carrier for drug molecules. | 8001-30-7 |
| HY-Y1890 | Cremophor EL | Others | Others | Cremophor EL is a polyethoxylated surfactant. | 61791-12-6 |
| HY-Y1891 | Tween 80 | Others | Others | Tween 80 is a surfactant which can also reduce bacterial attachment and inhibit biofilm formation. | 9005-65-6 |
| HY-Y1892 | Gelucire 44/14 | Others | Others | Gelucire 44/14 is a potential and safe absorption enhancer for improving the absorption of poorly absorbable drugs including insulin and calcitonin by pulmonary delivery. | 121548-04-7 |
| HY-Z0041 | Benzaldehyde dimethyl acetal | | | | 1125-88-8 |
| HY-Z0453 | Methyl 2-methoxybenzoate | | | | 606-45-1 |

TABLE 1-continued

Illustrative additional ingredients

| Catalog No | Drug Names | Target | Pathway | Biological Activity | CAS |
|---|---|---|---|---|---|
| HY-Z0478 | (−)-Limonene | Others | Others | (−)-Limonene ((S)-(−)-Limonene) is a monoterpene found in many pine-needle oils and in turpentine. (−)-Limonene can induce a mild bronchoconstrictive effect. | 5989-54-8 |
| TCG0275 | Copper (II) Gluconate | | | | 527-09-3 |

Additional information about the additional ingredients listed in Table 1 (e.g., the ingredient's target, pathway, and/or biological activity) can be determined from publicly available databases and websites. As an example, the American Chemical Society's website (see, the World Wide Web at cas.org), the Chemical Book (at the World Wide Web chemicalbook.com), and/or Med Chem Express (see, the World Wide Web at medchemexpress.com) provide relevant information for the additional ingredients; this information can be obtained by searching the website using an ingredient's name or CAS number. The contents of these websites, with respect to the additional ingredients listed in Table 1, are incorporated by references in their entireties.

Compositions of the present disclosure are formulated to be suitable for in vivo administration to a mammal. Such compositions can optionally comprise a suitable amount of a pharmaceutically acceptable excipient so as to provide the form for proper administration. Pharmaceutical excipients can be aqueous liquids, such as water or saline. Pharmaceutical excipients can be lipid based, e.g., comprising a liquid or solid oil. In addition, auxiliary, stabilizing, thickening, lubricating, and coloring agents can be used. The pharmaceutically acceptable excipients are sterile when administered to a subject. Water is a useful excipient when any composition described herein is administered parentally or in some oral formulations. In embodiments, the compositions described herein are suspended in a saline buffer (including, without limitation Ringer's, TBS, PBS, HEPES, HBSS, and the like). Saline solutions and aqueous dextrose and glycerol solutions can also be employed as liquid excipients, specifically for injectable solutions. Suitable pharmaceutical excipients also include starch, glucose, lactose, sucrose, glycerol monostearate, mannitol, sodium chloride, dried skim milk, glycerol, propylene, glycol, water, ethanol and the like. Any composition described herein, if desired, can also comprise pH buffering agents.

In embodiments, the compositions of the present disclosure are formulated for oral administration, for injection, or for topical administration. Administering the composition may comprise intravenous injection or infusion, intraperitoneal injection, intramuscular injection, or subcutaneous injection.

The compositions suitable for parenteral administration (e.g., intravenous injection or infusion, intraarterial injection or infusion, intramuscular injection, intraperitoneal injection, subcutaneous injection, and intra-arterial injection or infusion) include, for example, solutions, suspensions, dispersions, emulsions, and the like, or in another acceptable format used in methods well known in the art.

Compositions suitable for enteral administration (e.g., oral administration) may be formulated as a liquid, a suspension, a gel, a geltab, a semisolid, a tablet, a sachet, a lozenge, a pill, or a capsule, or in another acceptable format used in methods well known in the art.

In some embodiments, the active ingredient (disulfiram) and the potentiating ingredient (TBHQ) are formulated into a single composition, e.g., for oral administration. In some cases, disulfiram and TBHQ are combined into a single tablet or pill during manufacturing of the tablet or pill or by a compounding company/laboratory. Alternately, disulfiram and TBHQ are combined into a single capsule by combining the contents of capsules containing disulfiram and capsules containing TBHQ. Additionally, powders or pellets of disulfiram and TBHQ may be otherwise obtained and compounded into pills/tablets or combined into capsules.

As described above, a composition of the present disclosure may further comprise one or more additional ingredients (e.g., from Table 1). The one or more additional ingredients may be formulated into the single tablet, pill, or capsule with disulfiram and TBHQ.

In other embodiments, the active ingredient that is disulfiram and potentiating ingredient that is TBHQ are formulated into distinct compositions, e.g., for oral administration. In some cases, disulfiram is present in a single tablet, pill, or capsule and the TBHQ is present in another tablet, pill, or capsule. Further, a third composition, tablet, pill, or capsule may include one or more additional ingredients (e.g., from Table 1).

When the composition is for oral administration and is in solid form (e.g., a pill, tablet, or capsule), the composition may comprise delay-release components. For example, a pill, tablet, or capsule may comprise a coating that slows release of the agents and/or prevents release of disulfiram and/or the one or more additional ingredients until the pill, tablet, or capsule has arrived at a desired location of the mammal's digestive system.

Compositions suitable for topical administration can be formulated in a solution, gel, lotion, ointment, cream, suspension, paste, liniment, powder, tincture, aerosol, patch, or the like in a pharmaceutically or cosmetically acceptable format used in methods well known in the art.

Compositions may be suitable for administration via inhalation. Such formulation will likely be in liquid form and will be delivered in a spray bottle, in an inhaler, or in a nebulizer. Inhaled compositions are particularly suited for diseases and disorder, including infections, that affect the mammal's respiratory system and/or are transmitted via the mammal's respiratory system.

The dosage of any herein-disclosed composition or compositions can depend on several factors including the characteristics of the mammal to be administered. Examples of characteristics include species, strain, breed, sex, age, weight, size, health, and/or disease status. Moreover, the dosage may depend on whether the administration is the first time the subject received a composition of the present disclosure or if the subject has previously received a composition of the present disclosure. Additionally, pharmacogenomic (the effect of genotype on the pharmacokinetic, pharmacodynamic or efficacy profile of a composition) information about a particular subject may affect dosage used. Furthermore, the exact individual dosages can be adjusted somewhat depending on a variety of factors, including the specific composition being administered, the time of administration, the route of administration, the nature of the formulation, and the rate of excretion. Some variations in the dosage can be expected.

Moreover, the dosage may depend on the specific ingredients administered.

In embodiments, the active agent (disulfiram) and/or the potentiating ingredient (TBHQ) are encapsulated in a microcapsules. Disulfiram may be encapsulated in one microcapsule and TBHQ may be encapsulated into another microcapsule. Disulfiram and TBHQ may be encapsulated into one microcapsule. Disulfiram may be encapsulated in one microcapsule and TBHQ may not be encapsulated. Disulfiram may not be encapsulated and TBHQ may be encapsulated in a microcapsule. The microcapsule may be a liposome, an albumin microsphere, a microemulsion, a nanoparticle (e.g., a lipid nanoparticle), and a nanocapsule. In embodiments, microcapsules, e.g., lipid nanoparticles and liposomes, include lipids selected from one or more of the following categories: cationic lipids; anionic lipids; neutral lipids; multi-valent charged lipids; and zwitterionic lipids. In some cases, a cationic lipid and/or cationic polymer may be used to facilitate a charge-charge interaction with disulfiram and/or the one or more additional ingredients. The microcapsule may comprise a PEGylated lipid. Examples of microcapsules and methods for manufacturing the same are described in the art. See, e.g., Prui et al., Crit Rev Ther Drug Carrier Syst., 2009; 26(6): 523-580; Wakasar, J Drug Target, 2018, 26(4):311-318, Langer, 1990, Science 249:1527-1533; Treat et al., in "Liposomes in the Therapy of Infectious Disease and Cancer", Lopez-Berestein and Fidler (eds.), Liss, New York, pp. 353-365 (1989); Pelaz et al. "Diverse applications of nanomedicine." (2017): 2313-2381; the contents of each of which is incorporated herein by reference in its entirety.

Further, one or more additional ingredients (e.g., from Table 1) may be encapsulated and the disulfiram and/or TBHQ may be encapsulated, the one or more additional ingredients may be unencapsulated and disulfiram and/or TBHQ may be unencapsulated, and/or combinations thereof.

In embodiments, a composition may comprise one or more of capralactone, polylactide (PLA), polylactic-co-glycolic (PLGA), polyethylene glycol (PEG), polylactic-co-hydroxymethylglycolic acid (PLHMGA), carboxymethylcellulose, hydroxylmethylcellulose, gelatin-microcapsules, a poloxamer, or polymethylmethacrylate.

Disulfiram, as active agent, and TBHQ, as potentiating ingredient, may be administered to a subject in need thereof once per day, twice per day, or thrice per day. Disulfiram and TBHQ may be administered to a subject in need thereof once a week, twice a week, three times a week, four times a week, five times a week, or six times a week. Disulfiram and TBHQ may be administered to a subject in need thereof once a month, twice a month, three times a month, or four times a month.

When disulfiram and TBHQ are administered separately, i.e., in distinct compositions, the administration route of the first composition and the second composition may be the same or may be different. In one example, the first composition and the second composition are administered orally. In one example, the first composition and the second composition are administered by inhalation. In another example, the first composition is administered orally and the second composition is by injection, inhalation, or topically. In yet another example, the first composition is administered by inhalation and the second composition is by injection, orally, or topically.

Another aspect of the present disclosure is a composition comprising disulfiram as active agent and TBHQ as potentiating ingredient for use in any herein disclosed method. Yet another aspect of the present disclosure is a first composition comprising disulfiram and a second composition comprising TBHQ for use in any herein disclosed method.

Compositions of the present disclosure are formulated to be suitable for contacting a cell or an immune cell in vitro or ex vivo. In such embodiments, disulfiram and the one or more additional ingredients are formulated into a solution. The solute chosen depends on characteristics of the compound. For example, a water-soluble compound may be included in an aqueous solution, which comprises water or saline. A water-insoluble compound may be included in a non-aqueous solution, e.g., which comprises a lipid-based fluid or other hydrocarbon-based fluid. Disulfiram and the one or more additional ingredients may be formulated into a single solution. Alternately, disulfiram and the one or more additional ingredients may be formulated into distinct solutions.

Effectiveness of disulfiram and a specific additional ingredients may be validated in a pyroptosis inhibition assay. See, e.g., Example 3.

Illustrative Metal Additional Ingredients

In embodiments, the one or more additional ingredients is a metal. The metal may be selected from aluminum, calcium, copper, iron, magnesium, manganese, potassium, sodium, or zinc. Disulfiram has been shown to chelate certain metals and/or to be useful in the context of cancer treatments. See, e.g., Viola-Rhenals et al. "Recent Advances in Antabuse (Disulfiram): The Importance of its Metal-binding Ability to its Anticancer Activity", Curr Med Chem. 2018 Feb. 12; 25(4): 506-524; WO2018081309A1; and WO2019094053A1. The contents of each of which is incorporated herein by reference in its entirety.

The metal may be in the form of any metal salt or metal ester described in the present FDA's list of food additives, e.g., as listed in Table 1.

In embodiments, the metal is aluminum, calcium, copper, iron, magnesium, manganese, potassium, sodium, or zinc.

In embodiments, aluminum is in the form of aluminum hydroxide, aluminum oxide, or aluminum potassium disulfate dodecahydrate.

In embodiments, calcium is in the form of anhydrous calcium sulfate, calcium carbonate, calcium citrate tetrahydrate, calcium gluconate, calcium glycerol phosphate, calcium hydrogen phosphate dihydrate, calcium hydroxide, calcium lactate, calcium orthophosphate, or calcium phosphate.

In embodiments, copper is in the form of copper (II) gluconate, copper sulfate, or copper (I) iodide.

In embodiments, iron is in the form of ferric ammonium citrate, iron, iron (II) fumarate, or iron (II) sulfate heptahydrate.

In embodiments, magnesium is in the form of magnesium hydroxide, magnesium oxide, or magnesium silicate.

In embodiments, manganese is in the form of manganese dichloride or manganese sulfate.

In embodiments, potassium is in the form of dipotassium carbonate, potassium bromide, or potassium chloride.

In embodiments, sodium is in the form of disodium 5'-inosinate, disodium succinate, sodium benzoate, sodium carbonate, sodium chloride, sodium citrate (dihydrate), sodium dodecyl sulfate, sodium formate, sodium gluconate, sodium thiosulfate (pentahydrate), or trisodium citrate.

In embodiments, zinc is in the form of zinc sulfate (heptahydrate).

In some embodiments, the dosage of disulfiram may be about 0.1-60 units and the amount of the one or more additional ingredients, which is a metal, may be about 1 unit, where disulfiram ranges from 5-500 mg. The amount of a metal (is an above-described form) may between 0.1 mg to 30 mg. In an embodiment, the amount of the metal is between 1.5 mg and 3 mg. In embodiments, the metal is copper or zinc and approximately 1.5 mg of the metal is administered.

Illustrative Methods

The present disclosure provides a method for increasing lifespan in a mammal, for preventing or treating disease including an aging-related disorder in a mammal, for reducing a symptom of aging in a mammal, and/or boosting an immune system in a mammal. The methods comprise administering to the mammal a therapeutically effective amount of disulfiram as active agent and TBHQ as potentiating ingredient. Disulfiram and TBHQ may be administered with one or more of the additional ingredients listed in Table 1.

In embodiments, route of administration is oral, by injection, inhalation, or topical. In embodiments, the injection is intravenous injection or infusion, intraperitoneal injection, intramuscular injection, or subcutaneous injection.

In embodiments, one composition comprising disulfiram is administered and a second composition comprising TBHQ is administered. In other embodiments, one composition comprising both disulfiram and TBHQ is administered.

In embodiments, the mammal is near or has reached maturity.

In embodiments, the mammal is nearing or has reached halfway to its expected lifespan for the mammal's species, size, sex, age, and/or health status. In embodiments, the mammal has reached an age that is at least 60%, 70%, 80%, 90%, or 100% of its expected lifespan for the mammal's species, size, sex, age, and/or health status.

In embodiments, increasing lifespan comprises an at least 5% increase in lifespan relative to the expected or median lifespan of a mammal of similar species, sex, age, and/or health status. In embodiments, increasing lifespan comprises an at least 10%, at least 15%, at least 20%, or at least 25% increase in lifespan.

In embodiments, the mammal is a human, mouse, rat, guinea pig, dog, cat, horse, cow, pig, rabbit, sheep, or non-human primate, such as a monkey, chimpanzee, or baboon. In embodiments, the mammal is a human.

Without wishing to be bound by theory, the active agent disulfiram and the potentiating ingredient TBHQ (with or without one or more additional ingredients, e.g., of Table 1) mitigates dysfunction of or rejuvenates a signaling pathway disrupted by aging where the dysfunction can ultimately lead to aging-related disorders. In embodiments, the aging-related disorder or symptom of aging selected from one or more of actinic keratosis, age-related macular degeneration (AMD), alopecia, Alzheimer's disease, arthritis, atherosclerosis and cardiovascular disease, benign prostatic hyperplasia (BPH), bone atrophy, cachexia, cancer (e.g., a skin cancer such as basal cell carcinoma (BCC) and squamous cell carcinoma (SCC)), cardiomyopathy, cataracts, chronic obstructive pulmonary disease (COPD), idiopathic pulmonary fibrosis, constipation, decrease in overall energy, decrease in visual acuity, delirium, dementia, depression, dermal atrophy (thinning of the skin), diminished peripheral vision, dry eye, greater risk of heat stroke or hypothermia, hearing loss, hypertension, increased susceptibility to infection (including influenza and pneumonia), lentigines (aging spots), memory loss, metabolic syndrome, muscle atrophy (e.g., Sarcopenia and myopenia), frailty, muscle repair or rejuvenation deficiency, muscular dystrophy, osteoarthritis, osteoporosis, periodontitis, photoaging, reduced metabolism (including increased risk for obesity), reduced reflexes and coordination including difficulty with balance, respiratory disease (including acute lung injury (ALI) and/or acute respiratory distress syndrome (ARDS)), rheumatoid arthritis, sarcopenic obesity, sexual dysfunction, shingles, type 2 diabetes, urologic changes (including incontinence), vaginal atrophy, whitening or graying of hair, prolonged/inefficient wound healing, wrinkling/sagging skin (including loss of skin elasticity), and xerosis cutis (skin dryness). In embodiments, the aging-related disorder or symptom of aging is actinic keratosis, dermal atrophy (thinning of the skin), lentigines (aging spots), photoaging, vaginal atrophy, prolonged/inefficient wound healing, wrinkles, and/or xerosis cutis (skin dryness) and the administration route is oral or topical. In embodiments, the mammal has at least one aging-related disorder or symptom of aging. A non-human mammal may have an aging-related disorder or symptom of aging that is homologous to the aging-related disorder or symptom of aging listed above.

In an embodiment, a composition comprising disulfiram and TBHQ, or distinct compositions of a first composition comprising disulfiram and a second composition comprising TBHQ (with or without one or more additional ingredients, e.g., of Table 1) are administered to a mammal, e.g., a human, for preventing or treating a respiratory disease or disorder, e.g., acute lung injury (ALI) and/or acute respiratory distress syndrome (ARDS). Administration of the composition(s) is by intravenous injection or infusion, intraperitoneal injection, intramuscular injection, or subcutaneous injection, with a dose depending on the quantity of composition(s) needing to be administered. Alternately, the composition(s) are administered orally, by inhalation, or topically. Combinations of administration routes may be used. Treatment is identified as an improvement in the administered mammal in one or more of the following symptoms severe shortness of breath, labored and unusually rapid breathing, low blood pressure, and confusion and extreme tiredness. The improvement may be relative to the pre-administration state for the mammal. The underlying cause for the ALI and/or ARDS may be sepsis (e.g., a serious and widespread infection of the bloodstream); inhalation of a harmful substance (e.g., smoke, chemical fumes, asbestos, dust, particulates, vomit, and water); viral or bacterial pneumonia (which may affect up to all five lobes of the lungs) and other respiratory disorders including those caused by a coronavirus (e.g., SARS, MERS, and COVID-19), influenzas (influenza A, influenza B, or parainfluenza), pneumococcal infection, adenovirus, respiratory syncytial virus (RSV), enterovirus and/or other respiratory viral infections; and a head, chest or other major injury; or another cause (e.g., pancreatitis which is inflammation of the pancreas, a massive blood transfusion, and severe burns). In some embodiments, ALI differs from ARDS in that ALI exists during early stage of a respiratory disease and ARDS exists during a later state of the respiratory disease. In some, the composition or compositions prevent or treat idiopathic pulmonary fibrosis and/or chronic obstructive pulmonary disease.

In an embodiment, a composition comprising disulfiram and TBHQ, or distinct compositions of a first composition comprising disulfiram and a second composition comprising TBHQ (with or without one or more additional ingredients, e.g., of Table 1) are administered to a mammal, e.g., a human, for treating dry eye. The composition(s) may be administered topically (e.g., via eye drops or an eye ointment), with a dose depending on the quantity of composition(s) needing to be administered.

In an embodiment, a composition comprising disulfiram and TBHQ, or distinct compositions of a first composition comprising disulfiram and a second composition comprising TBHQ (with or without one or more additional ingredients, e.g., of Table 1) are administered to a mammal, e.g., a human, for treating alopecia. The composition(s) may be administered topically (e.g., gel, lotion, ointment, cream, suspension, paste, liniment, powder, tincture, or aerosol or via an impregnated solid support (e.g., a patch)), with a dose depending on the quantity of composition(s) needing to be administered. The composition may be administered orally, by injection, or by inhalation.

In an embodiment, a composition comprising disulfiram and TBHQ, or distinct compositions of a first composition comprising disulfiram and a second composition comprising TBHQ (with or without one or more additional ingredients, e.g., of Table 1) are administered to a mammal, e.g., a human, for treating a skin disorder, e.g., wrinkles, which may be a result of photoaging or related to actinic keratosis. Other skin disorders include dermal atrophy (thinning of the skin), lentigines (aging spots), vaginal atrophy, prolonged/inefficient wound healing, and/or xerosis cutis (skin dryness). The composition(s) may be formulated as a gel, lotion, ointment, cream, suspension, paste, liniment, powder, tincture, or aerosol or administered via an impregnated solid support (e.g., a patch)). The composition(s) may be administered orally or topically, with a dose depending on the quantity of composition(s) needing to be administered. Alternately, the composition(s) may be administered by injection or by inhalation. Combinations of administration routes may be used.

In an embodiment, a composition comprising disulfiram and TBHQ, or distinct compositions of a first composition comprising disulfiram and a second composition comprising TBHQ (with or without one or more additional ingredients, e.g., of Table 1) are administered to a mammal, e.g., a human, for treating a skin cancer, e.g., (e.g., basal cell carcinoma (BCC) and squamous cell carcinoma (SCC)). The compositions may be administered topically, with a dose depending on the quantity of composition needing to be administered. The compositions may be formulated as a gel, lotion, ointment, cream, suspension, paste, liniment, powder, tincture, or aerosol or administered via an impregnated solid support (e.g., a patch)). Alternately, the composition may be administered orally, by injection, or by inhalation. Combinations of administration routes may be used.

In embodiments, a therapeutically effective amount of disulfiram as active agent and TBHQ as potentiating ingredient (with or without one or more additional ingredients, e.g., of Table 1) treats or prevents a disease or a symptom thereof; as examples, the disease may be asthma, deafness, or a viral infections and a symptom thereof may be sepsis.

In embodiments, a therapeutically effective amount of the active agent disulfiram and the potentiating ingredient TBHQ (with or without one or more additional ingredients, e.g., of Table 1) boosts the immune system in the mammal.

As shown in Example 2, cells from older donors treated with disulfiram exhibited phenotypes of younger cells in response to viral infection. Further, disulfiram reduced inflammasome-mediated pyroptotic cell death. Importantly, the combination of disulfiram and TBHQ showed a synergistic effect on reduction of inflammasome activation, as shown in Example 3.

In embodiments, boosting the immune system increases an effective immune response against an infectious agent. In embodiments, the infectious agent is a virus, a bacterium, a fungus, a protozoan, a helminth, a prion, or a parasite. In embodiments, the bacterium is *Bordatella pertussis* or *Streptococcocus pneumoniae* or the virus is a Chickenpox virus, Coronavirus, Hepatitis A virus, Hepatitis B virus, Human papillomavirus, Human immunodeficiency virus (HIV), influenza, Japanese encephalitis virus, Measles, mumps, or rubella virus, Poliovirus, Rabies virus, Respiratory syncytial virus (RSV), Rotavirus, Shingles virus, Smallpox, Varicella virus, or Yellow fever virus. In embodiments, the Coronavirus is Sars-CoV-2. In embodiments, when the infectious agent affects the mammal's respiratory system or is transmitted via the mammal's respiratory system and the route of administration is by inhalation.

In embodiments, the route of administration is oral or by inhalation.

In embodiments, the mammal has a healthy immune system. In embodiments, the mammal has an unhealthy immune system, dysfunctional immune system, and/or weakened immune system.

The present disclosure provides an in vivo method for increasing lifespan of a cell and/or boosting activity of an immune cell comprising contacting the cell or the immune cell with disulfiram as active agent and TBHQ as potentiating ingredient. In some embodiments, the immune cell is contacted with disulfiram and TBHQ and one or more of the additional ingredients listed in Table 1. In such in vivo methods, disulfiram and TBHQ (with or without one or more additional ingredients) are administered to a subject, e.g., parenterally or enterally, and disulfiram and TBHQ (with or without the one more additional ingredients) contacts the cell or immune cell within the subject, e.g., by being carried through the subject's blood stream or the subject's lymphatic system or within extracellular spaces.

The present disclosure provides an in vitro or ex vivo method for increasing lifespan of a cell and/or boosting activity of an immune cell, the method comprises contacting the cell or the immune cell with a disulfiram as active agent and TBHQ as potentiating ingredient (with or without one or more of the additional ingredients listed in Table 1). Here, the cell or the immune cell is in a culturing vessel, e.g., a petri dish, tissue culture plate, or culture flask, and disulfiram and TBHQ (at least) are added to a medium (e.g., growth medium or buffer solution) surrounding the cell or immune cell.

In some methods, the one or more additional ingredients is a metal (e.g., copper and zinc).

Boosting the Immune System

Another aspect of the present disclosure is a method for boosting the immune system in a mammal.

The method for boosting an immune system in a mammal comprises administering to the mammal a therapeutically effective amount of disulfiram as active agent and TBHQ as potentiating ingredient, with or without one or more of the additional ingredients listed in Table 1.

In embodiments, boosting the immune system increases an effective immune response against an infectious agent. In embodiments, the infectious agent is a virus, a bacterium, a fungus, a protozoan, a helminth, a prion, or a parasite. In embodiments, the bacterium is *Bordatella pertussis* or *Streptococcocus pneumoniae*. In embodiments, the virus is selected from Alphavirus, BK virus, Bunyaviridae, Chickenpox virus, Colorado tick fever virus (CTFV), Coronaviruse, Crimean-Congo hemorrhagic fever virus, Cytomegalovirus, Dengue viruses (DEN-1, DEN-2, DEN-3 and DEN-4), Ebolavirus (EBOV), Enteroviruses, mainly Coxsackie A virus and enterovirus 71 (EV71), Epstein-Barr virus (EBV), Flaviviruses, Guanarito virus, Heartland virus, Hendra virus, Hepatitis A virus, Hepatitis B virus, Hepatitis C virus, Hepatitis D Virus, Hepatitis E virus, Herpes simplex virus 1 and 2 (HSV-1 and HSV-2), Human bocavirus (HBoV), Human herpesvirus 6 (HHV-6) and human herpesvirus 7 (HHV-7), Human immunodeficiency virus (HIV), Human metapneumovirus (hMPV), Human papillomaviruses (HPV), Human parainfluenza viruses (HPIV), Influenza, Japanese encephalitis virus, JC virus, Junin virus, Lassa virus, Lymphocytic choriomeningitis virus (LCMV), Machupo virus, Marburg virus, Measles virus, Middle East respiratory syndrome coronavirus, Molluscum contagiosum virus (MCV), Monkeypox virus, Mumps virus, Nipah virus, Norovirus, Orthomyxoviridae species, Parvovirus B19, Poliovirus, Rabies virus, Respiratory syncytial virus (RSV), Rhinovirus, Rift Valley fever virus, Rotavirus, Rubella virus, Sabia virus, SARS coronavirus, Severe acute respiratory syndrome coronavirus 2 (SARS-CoV-2), Shingles virus, Sin Nombre virus, Smallpox, Varicella zoster virus (VZV), Variola major or Variola minor, Venezuelan equine encephalitis virus, West Nile virus, Yellow fever virus, and Zika virus. In embodiments, the Coronavirus is Sars-CoV-2.

In embodiments, when the infectious agent affects the mammal's respiratory system or is transmitted via the mammal's respiratory system and the route of administration is by inhalation.

In embodiments, the route of administration is oral or by inhalation.

In some cases, the mammal has a healthy immune system. In other cases, the mammal has an unhealthy immune system, dysfunctional immune system, and/or weakened immune system.

In embodiments, the term dysfunctional immune system may be an overactive immune system, e.g., resulting in a cytokine storm; such overactive immune systems are observed in certain viral infections, e.g., in some severe coronavirus patients. In various embodiments, "boosting the immune system", relates to "boosting" a proper (e.g., non-pathological) immune response. That is, minimizing an overactive immune response.

In embodiments, the mammal is nearing or has reached halfway to its expected lifespan for the mammal's species, size, sex, age, and/or health status. In embodiments, the aged mammal has reached an age that is at least 60%, 70%, 80%, 90%, or 100% of its expected lifespan for the mammal's species, size, sex, age, and/or health status.

Of course, any mammal may benefit from a boost in the immune system. Thus, the compositions and methods for boosting the immune system can be used with aged and with non-aged mammals.

In embodiments, the route of administration is oral, by injection, inhalation, or topical. The administration route may comprise intravenous injection or infusion, intraperitoneal injection, intramuscular injection, or subcutaneous injection.

In embodiments, one composition comprising the active agent that is disulfiram is administered and a second composition comprising the potentiating ingredient that is TBHQ. In other embodiments, one composition comprising both disulfiram and TBHQ is administered. In some embodiments, one or more additional ingredients, e.g., of Table 1, is included in the composition with disulfiram and TBHQ, in the composition with disulfiram, in the composition with TBHQ, or in a composition without disulfiram or TBHQ.

In methods for boosting the immune system in a mammal, the one or more additional ingredients may be a metal (e.g., copper and zinc).

Improving a Vaccine Response

The present disclosure also provides a method for improving effectiveness of a vaccine in a mammal in need thereof. The method comprises administering a therapeutically effective amount of disulfiram as active agent and TBHQ as potentiating ingredient, with or without one or more of the additional ingredients listed in Table 1. Here, the mammal may contemporaneously and/or subsequently be administered a vaccine.

In embodiments, disulfiram and TBHQ (with or without one or more additional ingredients, e.g., of Table 1) and the vaccine are administered contemporaneously. In embodiments, the vaccine is administered subsequent to administering disulfiram and TBHQ, with or without one or more additional ingredients.

In embodiments, a therapeutically effective amount of disulfiram and TBHQ (with or without the one or more of the additional ingredients) boosts the immune system in the mammal. In embodiments, boosting the immune system increases an immune response against a component contained in the vaccine. In embodiments, the increased immune response promotes future immunity against the component contained in the vaccine.

It has been reported in the art that aged mammals respond less strongly to vaccines than mammal who are less aged. Accordingly, methods for improving effectiveness of a vaccine in an aged mammal are needed.

In embodiments, an aged mammal is nearing or has reached halfway to its expected lifespan for the mammal's species, size, sex, age, and/or health status. In embodiments, the aged mammal has reached an age that is at least 60%, 70%, 80%, 90%, or 100% of its expected lifespan for the mammal's species, size, sex, age, and/or health status.

Influenza is problematic in older adults with increased risk for serious complications and hospitalization. In addition, approximately 90% of flu-related deaths occur in this population, with influenza and pneumonia being the eighth leading cause of death among persons over 65 years of age in the United States. Even when death is avoided, older adults have an increased risk for secondary complications and morbidities from flu infection. Depending on how successful the WHO predicts the influenza strains causing seasonal epidemics, the produced vaccines show efficacy rates between 60% and 90%. However, vaccine effectiveness in adults aged 65 and older is usually significantly lower, ranging from an average of 28% protection against fatal and nonfatal complications (with large dispersion), 39% protection against typical influenza-like illness, and 49% protection against disease with confirmed virus infection. Influenza vaccine effectiveness is a significant problem in elderly as compared to young individuals and is associated with high rates of complicated illness including pneumonia, heart attacks, and strokes in the >65-year-old population.

Furthermore, the outbreak of the novel coronavirus (SARS-CoV-2) has had devastating effects on the aged and those with pre-existing health conditions. A mammal would particularly benefit from a composition of the present disclosure and methods of administering the same to improve effectiveness of a SARS-CoV-2 vaccine.

Of course, mammals who are not aged may benefit from improved effectiveness of a vaccine. Thus, the compositions and methods for improving effectiveness of a vaccine can be used with non-aged mammals.

In some cases, the mammal has an unhealthy immune system, dysfunctional immune system, and/or weakened immune system. In other cases, the mammal has a healthy immune system.

In embodiments, the term dysfunctional immune system may be an overactive immune system, e.g., resulting in a cytokine storm; such overactive immune systems are observed in certain viral infections, e.g., in some severe coronavirus patients. In various embodiments, "improving a vaccine response", relates to "improving" a proper (e.g., non-pathological) immune response to a vaccine and, later, when a subject is contacted with an infectious agent. That is, minimizing an overactive immune response and promoting a proper immune response.

In embodiments, the increased immune response promotes future immunity against the component contained in the vaccine. In embodiments, the component contained in the vaccine is an antigen obtained from, related to, homologous to, or expressed by an infectious agent.

In embodiments, the vaccine is a Chickenpox vaccine, Coronavirus vaccine, Diphtheria vaccine, Hepatitis A vaccine, Hepatitis B vaccine, *Haemophilus influenzae* type b vaccine, Human Immunovirus (HIV) vaccine, Human papillomavirus vaccine, influenza vaccine, Japanese encephalitis vaccine, Measles, mumps, or rubella (including MMR combined vaccine) vaccine, Meningococcal disease vaccine, Pneumococcal disease vaccine, Polio vaccine, Rabies vaccine, Respiratory syncytial virus (RSV) vaccine, Rotavirus vaccine, Shingles vaccine, Smallpox vaccine, Tetanus vaccine, Varicella virus vaccine, Whooping cough (part of the DTaP combined vaccine) vaccine, or Yellow fever vaccine. In embodiments, the vaccine is a coronavirus vaccine, e.g., directed against Sars-CoV-2.

In embodiments, disulfiram and TBHQ (with or without one or more of the additional ingredients) is administered orally, by injection, by inhalation, or topically. In embodiments, the vaccine is administered orally, by injection, by inhalation, or topically. In embodiments, the injection is intravenous injection or infusion, intraperitoneal injection, intramuscular injection, or subcutaneous injection.

In embodiments, one composition comprising disulfiram as active agent is administered and a second composition comprising TBHQ as potentiating ingredient is administered. Here, a third composition comprising on or more additional ingredients, e.g., of Table 1, is administrated. In other embodiments, one composition comprising both disulfiram and TBHQ (with or without the one or more additional ingredients) is administered.

In methods for improving effectiveness of a vaccine, the one or more additional ingredients may be a metal (e.g., copper and zinc).

2. Reducing the Predicted Age of Cell

An aspect of the present disclosure is a method for reducing a predicted biological age of a cell. The method comprises contacting the cell with a therapeutically effective amount of the active agent disulfiram and the potentiating ingredient TBHQ, with or without one or more additional ingredients listed in Table 1.

As shown in Example 2, cells from older donors treated with disulfiram exhibited phenotypes similar to younger donors. For instance, disulfiram significantly reduced several proinflammatory cytokines and significantly reduced the percentage of mitochondria with reticular shape. In addition, T cells from older donors treated with disulfiram exhibited a younger phenotype as compared to untreated controls.

In embodiments, the cell is in vitro, ex vivo, or in vivo.

In methods for reducing a predicted biological age of a cell, the one or more additional ingredients may be a metal (e.g., copper and zinc).

Assays and formulations used in methods for reducing a predicted biological age of a cell may be related to those described in US20190228840, the entire contents of which is incorporated by reference its entirety.

Aging-Related Disorders

The herein-disclosed compositions and methods treat, prevent, reduce the severity of, and/or delay the onset of various aging-related disorders, e.g., chronic diseases and disabilities/conditions of aging. Illustrative aging-related disorders include actinic keratosis, age-related macular degeneration (AMD), alopecia, Alzheimer's disease, arthritis, atherosclerosis and cardiovascular disease, benign prostatic hyperplasia (BPH), bone atrophy, cachexia, cancer (e.g., a skin cancer including basal cell carcinoma (BCC) and squamous cell carcinoma (SCC)), cardiomyopathy, cataracts, chronic obstructive pulmonary disease (COPD), constipation, decrease in overall energy, decrease in visual acuity, delirium, dementia, depression, dermal atrophy (thinning of the skin), diminished peripheral vision, dry eye, greater risk of heat stroke or hypothermia, hearing loss, hypertension, increased susceptibility to infection (including influenza and pneumonia), lentigines (aging spots), memory loss, metabolic syndrome, muscle atrophy (e.g., Sarcopenia and myopenia), frailty, muscle repair or rejuvenation deficiency, muscular dystrophy, osteoarthritis, osteoporosis, periodontitis, photoaging, reduced metabolism (including increased risk for obesity), reduced reflexes and coordination including difficulty with balance, respiratory disease (including acute lung injury (ALI) and/or acute respiratory distress syndrome (ARDS)), rheumatoid arthritis, sarcopenic obesity, sexual dysfunction, shingles, type 2 diabetes, urologic changes (including incontinence), vaginal atrophy, whitening or graying of hair, wrinkling/sagging skin (including loss of skin elasticity), and xerosis cutis (skin dryness). Aged non-human subjects experience similar, homologous, and/or equivalent aging-related disorders.

Without wishing to be bound by theory, disulfiram and the one or more additional ingredients mitigates dysfunction of or rejuvenates a signaling pathway disrupted by aging where the dysfunction can ultimately lead to aging-related disorders.

3. Inhibiting Pyroptosis

In any of the herein-disclosed aspects and embodiments, use of disulfiram as active agent and TBHQ as potentiating ingredient, with or without one or more additional ingredients, e.g., of Table 1, inhibits pyroptosis of a cell.

Pyroptosis is a highly inflammatory form of programmed cell death that occurs most frequently upon infection with intracellular pathogens and is likely to form part of the antimicrobial innate immune response. Pyroptosis results in a distinct morphology by a unique mechanism compared to those of other forms of cell death. For example, unlike apoptosis-type programmed cell death, in a cell that undergoes pyroptosis, gasdermin D pores are formed on the plasma membrane, resulting in water influx and cell lysis, and in some cases, release of IL-10, IL-18 and HMGB1.

The potentiating ingredient TBHQ enhances disulfiram's ability to inhibit pyroptosis, as shown in Example 3.

Subjects

In embodiments, the subject is a mammal, e.g., a human, mouse, rat, guinea pig, dog, cat, horse, cow, pig, rabbit, sheep, or non-human primate, such as a monkey, chimpanzee, or baboon. In embodiments, the mammal is a non-rodent. In embodiments, the mammal is a dog. In embodiments, the subject is a non-human animal, and therefore the invention pertains to veterinary use. In a specific embodiment, the non-human animal is a household pet, e.g., a dog. In another specific embodiment, the non-human animal is a livestock animal. In embodiments, the mammal is a human.

In embodiments, the mammal has reached maturity. As used herein, the term mature or maturity, and the like, refers to a mammal that is capable of sexual reproduction and/or a mammal that has achieved its adult height and/or length.

In embodiments, the mammal is nearing or has reached halfway to its expected lifespan for the mammal's species, size, sex, age, and/or health status. The mammal may have reached an age that is at least 60%, 70%, 80%, 90%, or 100% of its expected lifespan for the mammal's species, size, sex, age, and/or health status.

In embodiments, the human is an adult human. In embodiments, the human has an age in a range of from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old, or older.

In some cases, the mammal has an unhealthy immune system, dysfunctional immune system, and/or weakened immune system. In other cases, the mammal has a healthy immune system.

Further Embodiments

Embodiment 1: A method for increasing lifespan in a mammal, for preventing or treating disease including an aging-related disorder in a mammal, for reducing a symptom of aging in a mammal, and/or boosting an immune system in a mammal comprising: administering to the mammal one or more compositions that each or together comprise an active agent that is disulfiram and a potentiating ingredient that is tert-Butylhydroquinone (TBHQ).

Embodiment 2: An in vivo, in vitro, or ex vivo method for increasing lifespan of a cell and/or boosting activity of an immune cell comprising contacting the cell or the immune cell with one or more compositions that each or together comprise an active agent that is disulfiram and a potentiating ingredient that is tert-Butylhydroquinone (TBHQ).

Embodiment 3: The method of embodiment 1 or embodiment 2, wherein one composition is administered that consists essentially of disulfiram and TBHQ.

Embodiment 4: The method of embodiment 1 or embodiment 2, wherein more than one composition is administered with a first composition consisting essentially of disulfiram and with a second composition consisting essentially of TBHQ.

Embodiment 5: The method of any one of embodiments 1 to 4, wherein the one or more compositions independently further comprises one or more additional ingredients from Table 1.

Embodiment 6: The method of any one of embodiments 1 to 5, wherein the administering is oral, by injection, inhalation, or topical.

Embodiment 7: The method of any one of embodiments 1 to 6, wherein the mammal is near or has reached maturity.

Embodiment 8: The method of any one of embodiments 1 to 6, wherein the mammal is nearing or has reached halfway to its expected lifespan for the mammal's species, size, sex, age, and/or health status.

Embodiment 9: The method of any one of embodiments 1 to 6, wherein the mammal has reached an age that is at least 60%, 70%, 80%, 90%, or 100% of its expected lifespan for the mammal's species, size, sex, age, and/or health status.

Embodiment 10: The method of any one of embodiments 1 to 9, wherein the mammal is a human, mouse, rat, guinea pig, dog, cat, horse, cow, pig, rabbit, sheep, or non-human primate, such as a monkey, chimpanzee, or baboon.

Embodiment 11: The method of embodiment 10, wherein the mammal is a human.

Embodiment 12: The method of any one of embodiments 1 to 11, wherein increasing lifespan comprises an at least 5% increase in lifespan relative to the expected or median lifespan of a mammal of similar species, sex, age, and/or health status.

Embodiment 13: The method of embodiment 12, wherein increasing lifespan comprises an at least 10%, at least 15%, at least 20%, or at least 25% increase in lifespan.

Embodiment 14: The method of any one of embodiments 1 to 13, wherein the aging-related disorder or symptom of aging selected from one or more of actinic keratosis, age-related macular degeneration (AMD), alopecia, Alzheimer's disease, arthritis, atherosclerosis and cardiovascular disease, benign prostatic hyperplasia (BPH), bone atrophy, cachexia, cancer (e.g., a skin cancer including basal cell carcinoma (BCC) and squamous cell carcinoma (SCC)), cardiomyopathy, cataracts, chronic obstructive pulmonary disease (COPD), constipation, decrease in overall energy, decrease in visual acuity, delirium, dementia, depression, dermal atrophy (thinning of the skin), diminished peripheral vision, dry eye, greater risk of heat stroke or hypothermia, hearing loss, hypertension, increased susceptibility to infection (including influenza and pneumonia), lentigines (aging spots), memory loss, metabolic syndrome, muscle atrophy (e.g., Sarcopenia and myopenia), frailty, muscle repair or rejuvenation deficiency, muscular dystrophy, osteoarthritis, osteoporosis, periodontitis, photoaging, reduced metabolism (including increased risk for obesity), reduced reflexes and coordination including difficulty with balance, respiratory disease (including acute lung injury (ALI) and/or acute respiratory distress syndrome (ARDS)), rheumatoid arthritis, sarcopenic obesity, sexual dysfunction, shingles, type 2 diabetes, urologic changes (including incontinence), vaginal atrophy, whitening or graying of hair, prolonged/inefficient wound healing, wrinkling/sagging skin (including loss of skin elasticity), and xerosis cutis (skin dryness); or the disease includes asthma, deafness, or a viral infections and/or a symptom of the disease comprises sepsis.

Embodiment 15: The method of embodiment 14, wherein the aging-related disorder or symptom of aging is actinic keratosis, dermal atrophy (thinning of the skin), lentigines (aging spots), photoaging, vaginal atrophy, prolonged/inefficient wound healing, wrinkles, and/or xerosis cutis (skin dryness) and wherein the administering is oral or topical.

Embodiment 16: The method of embodiment 14 or embodiment 15, wherein the mammal has at least one aging-related disorder or symptom of aging.

Embodiment 17: The method of any one of embodiments 1 to 16, wherein the disulfiram and the TBHQ boosts the immune system in the mammal.

Embodiment 18: The method of embodiment 17, wherein boosting the immune system increases an effective immune response against an infectious agent.

Embodiment 19: The method of embodiment 18, wherein the infectious agent is a virus, a bacterium, a fungus, a protozoan, a helminth, a prion, or a parasite.

Embodiment 20: The method of embodiment 19, wherein the bacterium is *Bordatella pertussis* or *Streptococcocus pneumoniae* or the virus is a Chickenpox virus, Coronavirus, Hepatitis A virus, Hepatitis B virus, Human papillomavirus, Human immunodeficiency virus (HIV), influenza (e.g., Influenza A, Influenza B, and parainfluenza), Japanese encephalitis virus, Measles, mumps, or rubella virus, Poliovirus, Rabies virus, Respiratory syncytial virus (RSV), Rotavirus, Shingles virus, Smallpox, Varicella virus, or Yellow fever virus.

Embodiment 21: The method of embodiment 20, wherein the Coronavirus is Sars-CoV-2.

Embodiment 22: The method of any one of embodiments 18 to 21, wherein the infectious agent affects the mammal's respiratory system or is transmitted via the mammal's respiratory system and wherein the administering is orally or by inhalation.

Embodiment 23: The method of any one of embodiments 1 to 22, wherein the mammal has a healthy immune system.

Embodiment 24: The method of any one of embodiments 1 to 22, wherein the mammal has an unhealthy immune system, dysfunctional immune system, and/or weakened immune system.

Embodiment 25: A method for improving effectiveness of a vaccine in a mammal in need thereof, the method comprises administering a therapeutically effective amount of one or more compositions that each or together comprise an active agent that is disulfiram and a potentiating ingredient that is tert-Butylhydroquinone (TBHQ), wherein the mammal contemporaneously and/or subsequently will be administered a vaccine.

Embodiment 26: The method of embodiment 25, wherein one composition is administered that consists essentially of disulfiram and TBHQ.

Embodiment 27: The method of embodiment 25, wherein more than one composition is administered with a first composition consisting essentially of the disulfiram and with a second composition consisting essentially of TBHQ.

Embodiment 28: The method of any one of embodiments 25 to 27, wherein the one or more compositions independently further comprises one or more additional ingredients from Table 1.

Embodiment 29: The method of any one of embodiments 25 to 28, wherein the one or more compositions and the vaccine are administered contemporaneously.

Embodiment 30: The method of any one of embodiments 25 to 29, wherein the vaccine is administered subsequent to administering the one or more composition.

Embodiment 31: The method of any one of embodiments 25 to 30, wherein the therapeutically effective amount of the one or more compositions boosts the immune system in the mammal.

Embodiment 32: The method of embodiment 31, wherein boosting the immune system increases an immune response against a component contained in the vaccine.

Embodiment 33: The method of embodiment 32, wherein the increased immune response promotes future immunity against the component contained in the vaccine.

Embodiment 34: The method of any one of embodiments 25 to 33, wherein the component contained in the vaccine is an antigen obtained from, related to, homologous to, or expressed by an infectious agent.

Embodiment 35: The method of any one of embodiments 25 to 34, wherein the vaccine is a Chickenpox vaccine, Coronavirus vaccine, Diphtheria vaccine, Hepatitis A vaccine, Hepatitis B vaccine, *Haemophilus influenzae* type b vaccine, Human Immunovirus (HIV) vaccine, Human papillomavirus vaccine, influenza vaccine, Japanese encephalitis vaccine, Measles, mumps, or rubella (including MMR combined vaccine) vaccine, Meningococcal disease vaccine, Pneumococcal disease vaccine, Polio vaccine, Rabies vaccine, Respiratory syncytial virus (RSV) vaccine, Rotavirus vaccine, Shingles vaccine, Smallpox vaccine, Tetanus vaccine, Varicella virus vaccine, Whooping cough (part of the DTaP combined vaccine) vaccine, or Yellow fever vaccine.

Embodiment 36: The method of embodiment 34, wherein the vaccine is a coronavirus vaccine, e.g., Sars-CoV-2.

Embodiment 37: The method of any one of embodiments 25 to 36, wherein the mammal has a healthy immune system.

Embodiment 38: The method of any one of embodiments 25 to 36, wherein the mammal has an unhealthy immune system, dysfunctional immune system, and/or weakened immune system.

Embodiment 39: The method of any one of embodiments 25 to 38, wherein the administering of the one or more compositions is oral, by injection, inhalation, or topical.

Embodiment 40: The method of any one of embodiments 25 to 39, wherein the administering of the vaccine is oral, by injection, inhalation, or topical.

Embodiment 41: The method of any one of embodiments 1 to 40, wherein the disulfiram is administered in a dose from about 5 to about 500 mg.

Embodiment 42: The method of any one of embodiments 1 to 41, wherein the TBHQ is administered in a dose from about 0.02% to about 56% of the weight of the disulfiram.

Embodiment 43: The method of any one of embodiments 1, 2, 4-25, or 27-42, wherein the one or more compositions independently further comprises a metal.

Embodiment 44: The method of embodiment 43, wherein the metal aluminum, calcium, copper, iron, magnesium, manganese, potassium, sodium, or zinc.

Embodiment 45: The method of embodiment 44, wherein the metal is aluminum hydroxide, aluminum oxide, aluminum potassium disulfate dodecahydrate, anhydrous calcium sulfate, calcium carbonate, calcium citrate tetrahydrate, calcium gluconate, calcium glycerol phosphate, calcium hydrogen phosphate dihydrate, calcium hydroxide, calcium lactate, calcium orthophosphate, calcium phosphate, copper (II) gluconate, copper sulfate, copper (I) iodide, ferric ammonium citrate, iron, iron (II) fumarate, iron (II) sulfate heptahydrate, magnesium hydroxide, magnesium oxide, magnesium silicate, manganese dichloride, manganese sulfate, dipotassium carbonate, potassium bromide, potassium chloride, disodium 5'-inosinate, disodium succinate, sodium benzoate, sodium carbonate, sodium chloride, sodium citrate (dihydrate), sodium dodecyl sulfate, sodium formate, sodium gluconate, sodium thiosulfate (pentahydrate), trisodium citrate, or zinc sulfate (heptahydrate).

Embodiment 46: The method of embodiment 45 wherein the metal is copper (II) gluconate, copper sulfate, copper (I) iodide, or zinc sulfate (heptahydrate).

Embodiment 47: The method of any one of embodiments 42 to 46, wherein the amount of the metal is between about 0.1 mg to about 30 mg.

Embodiment 48: The method of embodiment 47, wherein the amount of the metal is between about 1.5 mg and 3 mg.

Embodiment 49: The method of embodiment 48, wherein the metal is copper or zinc and approximately 1.5 mg of the metal is administered per dose.

Embodiment 50: A method for reducing a predicted biological age of a cell comprising contacting the cell with a therapeutically effective amount of one or more compositions that each or together comprise an active agent that is disulfiram and a potentiating ingredient that is tert-Butylhydroquinone (TBHQ).

Embodiment 51: The method of embodiment 50, wherein one composition is administered that consists essentially of disulfiram and TBHQ.

Embodiment 52: The method of embodiment 50, wherein more than one composition is administered with a first composition consisting essentially of disulfiram and with a second composition consisting essentially of TBHQ.

Embodiment 53: The method of any one of embodiments 50 to 52, wherein the one or more compositions independently further comprises one or more additional ingredients from Table 1.

Embodiment 54: The method of any one of embodiments 50 to 53, wherein the cell is in vitro, ex vivo, or in vivo.

Embodiment 55: The method of any one of embodiments 1 to 54, wherein the disulfiram inhibits pyroptosis of a cell.

Embodiment 56: The method of embodiment 55, wherein the TBHQ potentiates disulfiram's inhibition of pyroptosis of a cell.

Embodiment 57: The method of any one of embodiments 1 to 56, wherein the one or more compositions inhibits pyroptosis of a cell.

Embodiment 58: One or more compositions that each or together comprise an active agent that is disulfiram and a potentiating ingredient that is TBHQ for use in the method of any one of embodiments 1 to 56.

Embodiment 59: The one or more compositions of embodiment 58, wherein the disulfiram is in an amount from about 5 mg to about 500 mg.

Embodiment 60: The one or more compositions of embodiment 58 or embodiment 59, wherein the TBHQ is in an amount from about 0.02% to about 56% of the weight of the disulfiram.

Embodiment 61: A composition comprising an active agent that is disulfiram and a potentiating ingredient that is tert-Butylhydroquinone (TBHQ).

Embodiment 62: The composition of embodiment 61, wherein the composition consists essentially of disulfiram and TBHQ.

Embodiment 63: The composition of embodiment 61 or embodiment 62, further comprising one or more additional ingredients from Table 1.

Embodiment 64: The composition of any one of embodiments 61 to 63, wherein the disulfiram is in an amount from about 5 mg to about 500 mg.

Embodiment 65: The composition of any one of embodiments 61 to 64, wherein the TBHQ is in an amount from about 0.02% to about 56% by weight of the disulfiram.

REFERENCES

The following references are incorporated into this disclosure: Hu et al., "FDA-approved disulfiram inhibits pyroptosis by blocking gasdermin D pore formation." Nature Immunology (2020): 1-10; Liu et al., "Inflammasome-activated gasdermin D causes pyroptosis by forming membrane pores." Nature. 2016; 535(7610):153-158; McCarthy A. "Disulfiram inhibits inflammatory gatekeeper protein: Could it be helpful in COVID-19". Boston Children's Press Release. 10 May 2020; WO2020006229A1; Lin, et al. "Disulfiram can inhibit MERS and SARS coronavirus papain-like proteases via different modes". Antiviral Res. 2018; 150:155-163; Loo and Clarke "Blockage of drug resistance in vitro by disulfiram, a drug used to treat alcoholism." J Natl Cancer Inst. 2000; 92(11):898-902; and Sauna et al., "The molecular basis of the action of disulfiram as a modulator of the multidrug resistance-linked ATP binding cassette transporters MDR1 (ABCB1) and MRP1 (ABCC1)." Mol Pharmacol. 2004; 65(3):675-684. Each of the above-mentioned documents is incorporated by reference in its entirety

DEFINITIONS

The terminology used herein is for the purpose of describing particular cases only and is not intended to be limiting.

The term "disulfiram" includes the compound disulfiram itself as well as its metabolites and/or derivatives. The term "additional ingredient(s)" includes the additional ingredient(s) as well as its/their metabolites, derivatives, and/or precursors.

As used herein, unless otherwise indicated, the terms "a", "an" and "the" are intended to include the plural forms as well as the single forms, unless the context clearly indicates otherwise.

The terms "comprise", "comprising", "contain," "containing," "including", "includes", "having", "has", "with", or variants thereof as used in either the present disclosure and/or in the claims, are intended to be inclusive in a manner similar to the term "comprising."

By preventing is meant, at least, avoiding the occurrence of a disease and/or reducing the likelihood of acquiring the disease. By treating is meant, at least, ameliorating or avoiding the effects of a disease, including reducing a sign or symptom of the disease.

The term "about" or "approximately" means within an acceptable error range for the particular value as determined by one of ordinary skill in the art, which will depend in part on how the value is measured or determined, e.g., the limitations of the measurement system. For example, "about" can mean 10% greater than or less than the stated value. In another example, "about" can mean within 1 or more than 1 standard deviation, per the practice in the given value. Where particular values are described in the application and claims, unless otherwise stated the term "about" should be assumed to mean an acceptable error range for the particular value.

By "one or more" is meant at least one, e.g., one, two, three, four, five, six, seven, eight, nine, ten or more.

The "boosting the immune system", in various embodiments, relates to "boosting" a proper (e.g., non-pathological) immune response. In some cases, this will minimize an overactive immune response. In embodiments, the term dysfunctional immune system may be an overactive immune system, e.g., resulting in a cytokine storm; such overactive immune systems are observed in certain viral infections, e.g., in some severe coronavirus patients. In other cases, this will improve, activate, and/or enhance a proper immune response, e.g., when exposed to a vaccine comprising an antigen obtained from, related to, homologous to, or expressed by an infectious agent, when exposed to an infectious agent, and/or when exposed to an atypical cell in need of being attacked by an immune cell.

Any aspect or embodiment described herein can be combined with any other aspect or embodiment as disclosed herein.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Identification of Combinations of Disulfiram and Potentiating Ingredients Useful in Methods of the Present Disclosure In this example, disulfiram and potentiating ingredients capable of increasing lifespan in a mammal, of preventing or treating a disease including an aging-related disorder in a mammal, of reducing a symptom of aging in a mammal, and/or of boosting an immune system were identified.

Sets of cultured cells—fibroblasts, peripheral blood mononuclear cells (PBMCs including lymphocytes and monocytes, and/or myoblasts having either characteristics of young cells or characteristics of old cells were contacted with a combination of disulfiram and one or more potentiating ingredients from Table 1. The ability of disulfiram and one or more potentiating ingredients to reverse aging in the cells, e.g., reducing the characteristics of old cells and promoting characteristics of a young cells was assayed (also known as reducing the predicted age of the cells). Disulfiram and one or more potentiating ingredients were used at various concentrations ranging from 0.000005 to 80 µM. In some cases, the concentration of disulfiram was as high as 80 µM and the concentration of the potentiating ingredient was as high as 25 µM. Combinations of disulfiram and one or more potentiating ingredients showing the ability to reverse aging were further validated.

Assays and formulations used in this example are related to those described in US20190228840, the entire contents of which is incorporated by reference its entirety.

In this experiment, TBHQ was identified as a potentiating ingredient.

Example 2: Phenotypic Effect of Disulfiram on Immune Cells

In this example, disulfiram was shown to modify quantifiable parameters in virally infected cells from older donors that reflects those observed in cells from younger donor.

Whole blood from younger and older donors was collected into EDTA tubes and then diluted with an equal volume of phosphate-buffered saline (PBS)+2% fetal bovine serum (FBS) and layered over Ficoll using SepMate™-50 tubes (STEMCELL Technologies Inc., Vancouver, Canada). Cells were centrifuged at 1200 g for 10 min at room temperature, and the top plasma layer was removed. Peripheral blood mononuclear cells (PBMCs) were collected, washed with PBS+2% FBS, and counted using acridine orange/propidium iodide using a Cellometer® Vision CBA (Nexcelom Bioscience, Lawrence, Mass., USA). PBMCs were cryopreserved in CryoStor® CS10 (BioLife Solutions, Bothell, Wash., USA), frozen using CoolCell® FTS30 freezing containers (BioCision, San Rafael, Calif., USA), and stored in the liquid nitrogen vapor phase until use.

Specific cell types were isolated from the PBMC fraction using the following kits (STEMCELL Technologies Inc.) per manufacturer's recommendations: EasySep™ Human T Cell Enrichment Kit (T cells); EasySep™ Human B Cell Enrichment Kit (B cells); EasySep™ Human NK Cell Enrichment Kit (NK cells); and EasySep™ Human Monocyte Enrichment Kit (monocytes). T cells (CD3+), B cells (CD19+), natural killer (NK) cells (CD59+), and monocytes (CD14+) were isolated based on their customarily defined gene expression markers. Isolated cells were counted using acridine orange/propidium iodide on a Cellometer Vision CBA and then cryopreserved as described above until use.

After cells undertook a 30-min adhesion onto a 384-well assay plate, 10 µL of 5× trigger medium (including vesicular stomatitis virus encoding a red fluorescent protein (rVSV-ΔG-mCherry), DMSO, test compound, and FBS) was added to the assay plate using a 384-well pipetting head to achieve a final concentration of rVSV-ΔG-mCherry at 10×MOI, 0.1% DMSO, 10% FBS, and 0.33 µM or 5.3 µM compound concentration. The assay plate was centrifuged for 1 min at 138×g and incubated for 24 h at 37° C. with 5% humidity.

rVSV-ΔG-mCherry infected monocytes and macrophages, which subsequently created a highly inflamed environment for the lymphocytes and other cells. rVSV-ΔG-mCherry was used because of its ability to model the innate immune activation pathways of prevalent respiratory RNA viruses and because it was safe to use in a high-throughput laboratory with biosafety level one.

Virally infected cells were contacted with different concentrations of disulfiram (e.g., 0.00 µM, 0.02 µM, 0.10 µM, 0.33 µM, 1.65 µM, 6.25 µM, and 25.02 µM).

Cytokine levels in the cellular supernatant were evaluated using the FirePlex-HT assay system with the Human Cytokines FirePlex-HT Panel 1 (ab234897; Abcam). Morphological/cellular phenotypes were assayed.

Disulfiram demonstrated notable effects on cellular phenotypes in older immune cells that were suggestive of a rejuvenation of the response to infection.

Disulfiram significantly reduced several proinflammatory cytokines when compared with old untreated controls. MCP1, IL-1β, IL-6, and TNFα all significantly decreased in at least 2 doses (FIG. 1A). Again, the reduction in MCP1 followed a downward dose response (0.02 µM [P=0.35]; 0.1 µM [P=0.04]; 0.33 µM [P<0.001]; 1.65 µM [P<0.001]; 6.25 µM [P<0.001]; 25.02 µM [P<0.001]; FIG. 1A). IL-1β was significantly reduced after the second lowest dose, then stayed significantly low for all higher doses (0.02 µM [P=0.28]; 0.1 µM [P=0.005]; 0.33 µM [P=0.001]; 1.65 µM [P=0.004]; 6.25 µM [P=0.004]; 25.02 µM [P<0.001]; FIG. 1A). These anti-inflammatory effects caused disulfiram showing its potential to improve older viral immune responses to infection.

Figure 1B:
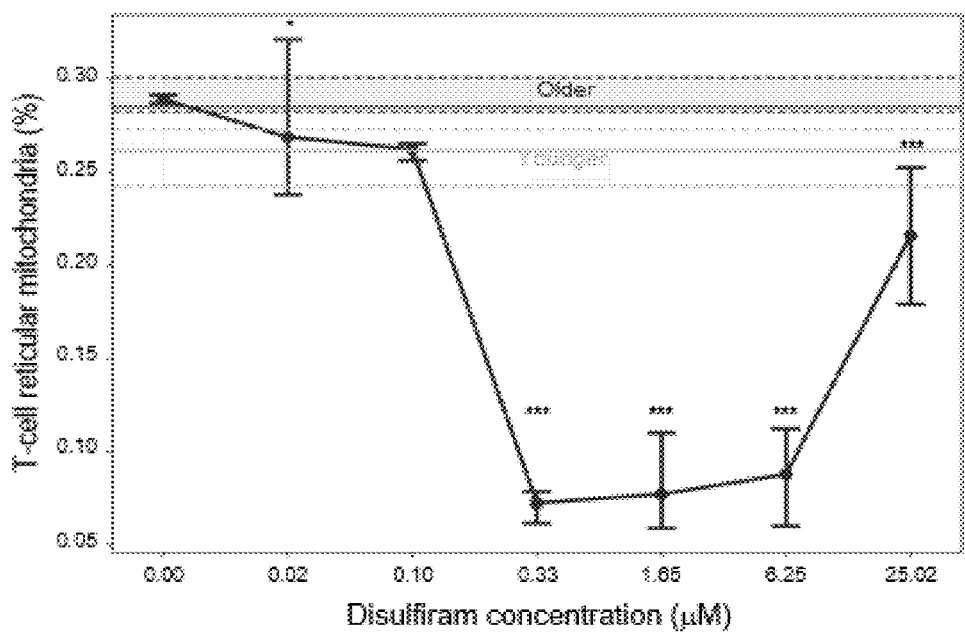

Disulfiram improved the appearance of virally infected cells. Untreated and treated PBMCs were exposed to 10×MOI rVSV, yet, at several doses, disulfiram made the cells appear like they were responding to a lower viral load. Compared with old controls, which appeared to be responding to 10×MOI rVSV, the higher doses of disulfiram made the cells appear to be responding to a lower viral load (0.02 µM [P=0.63]; 0.1 µM [P=0.01]; 0.33 µM [P=0.43]; 1.65 µM [P=0.05]; 6.25 µM [P<0.001]; 25.02 µM [P<0.001]). The higher doses of disulfiram also significantly reduced the percentage of the mitochondria with a reticular shape (0.02 µM [P=0.04]; 0.1 µM [P=0.42]; 0.33 µM [P<0.001]; 1.65 µM [P<0.001]; 6.25 µM [P<0.001]; 25.02 µM [P<0.001]; FIG. 1B). Both of these effects restore important phenotypes of the older viral immune response.

Figure 1C:
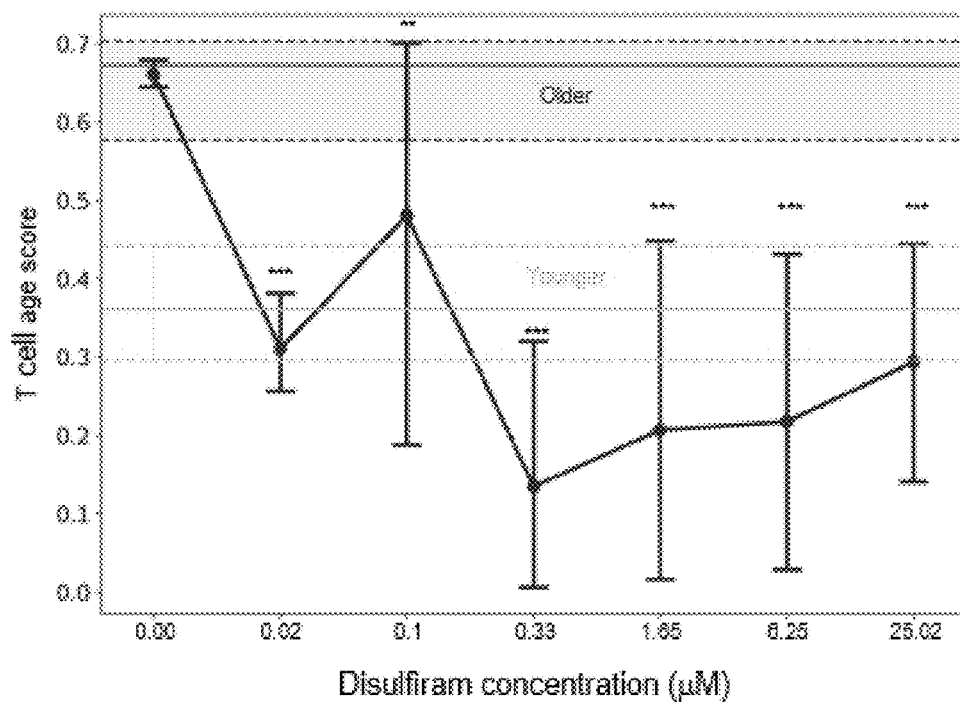

T cells treated with disulfiram also exhibited a much younger phenotype compared with old untreated controls. The first two doses of disulfiram saw a significant rejuvenating effect on the T-cell age scores in the multi-phenotype aging profiles (0.02 µM [P<0.001]; 0.1 µM [P=0.005]; FIG. 1C). The higher doses of disulfiram also saw significant, beneficial reductions in the T-cell age score (0.33 [P<0.001]; 1.65 µM [P<0.001]; 6.25 µM [P<0.001]; 25.02 µM [P<0.001]; FIG. 1C).

Figure 1D:
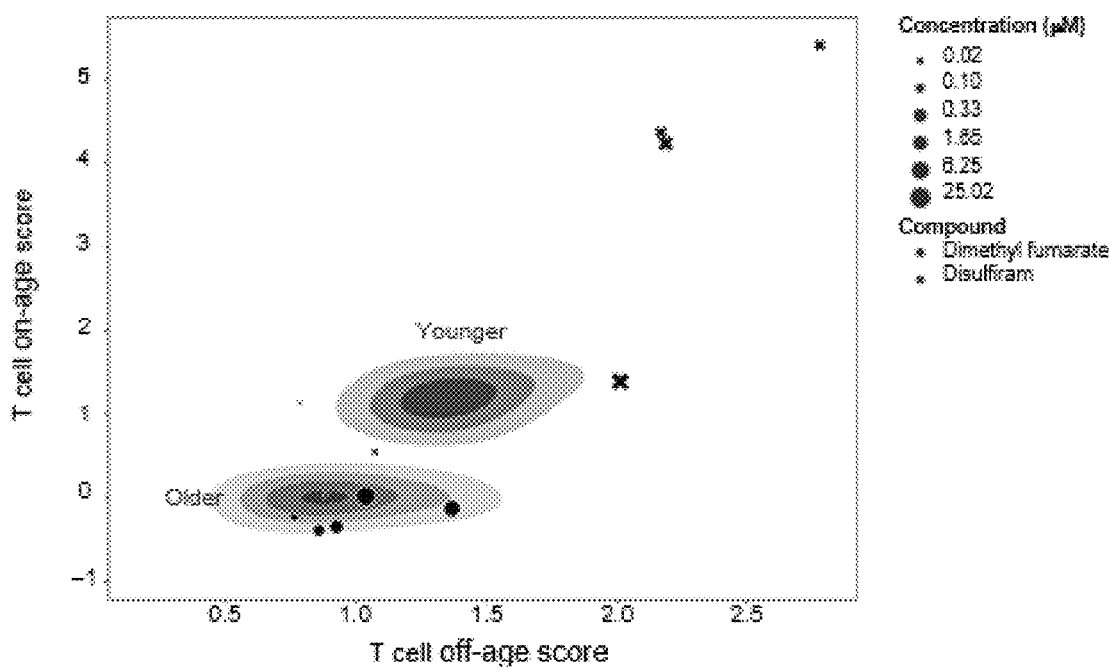

Similar trends were seen with the "on-age" and "off-age" scores. Compared with controls, the "on-age" T-cell score significantly shifted in the young direction after treatment with disulfiram (0.02 [P=0.003]; 0.1 µM [P=0.11]; 0.33 µM [P<0.001]; 1.65 µM [P<0.001]; 6.25 µM [P<0.001]; 25.02 µM [P<0.001]; FIG. 1D). The "off-age" score also had a significant effect but only in the higher doses (0.02 µM [P=0.26]; 0.1 µM [P=0.44]; 0.33 µM [P<0.001]; 1.65 µM [P=0.008]; 6.25 µM [P=0.003]; 25.02 µM [P=0.01]; FIG. 1D). All these beneficial shifts in age-related phenotypes show the strong beneficial potential of disulfiram for treating dysfunction in the older viral immune response.

Machine learning model predictions of the immune response resulting from different viral loads (at 0.1×, 1×, and 10×MOI) were notably different with disulfiram treatment compared with untreated control cells. At higher disulfiram concentrations, the model indicated that monocytes responded at a lower MOI than did untreated control cells.

Together, disulfiram restored multiple aspects of the viral immune response of older adults to a younger state demonstrating its usefulness in therapeutic methods of the present disclosure.

Disulfiram also appeared to operate via several anti-inflammatory mechanisms, including an ability to inhibit NLRP3 inflammasome-mediated pyroptotic cell death. The inflammasome-blocking mechanisms of disulfiram ultimately inhibits pyroptosis by stopping formation of pores in the cell membrane that lead to cell lysis and release of proinflammatory molecules such as IL-1β and IL-18. The data presented herein show that disulfiram restores aspects of the old viral immune response.

These data demonstrated significant anti-inflammatory and rejuvenating effects by disulfiram. Disulfiram reduced the proinflammatory cytokines MCP1, IL-1β, IL-6, and TNFα while also rejuvenating several other features in aging profile such as T-cell age score, viral load response, and mitochondrial function. These immunomodulatory mechanisms could be related to the ability of disulfiram to block the final step in inflammasome-mediated pyroptosis and cytokine release. Disulfiram may also operate by ultimately reducing pore formation on the cell membrane of neutrophils, which would allow for the release of neutrophil extracellular traps (NETs), a process known as NETosis. Both of these mechanisms make disulfiram an attractive treatment for hyperinflammatory infections such as COVID-19 and sepsis. Disulfiram has already been shown to protect mice from lethal lipopolysaccharide-induced septic shock. By targeting any of these mechanisms, disulfiram may be a useful agent for treating infection, e.g., caused by a virus such as SARS-CoV2.

Sera from patients with severe COVID-19 demonstrated increased NETs and an autopsy of a lung specimen from a patient with COVID-19 showed extensive neutrophil infiltration. Proinflammatory cytokines in patients with severe COVID-19 were significantly higher than in moderate cases. This includes elevated levels of IL-1β that result from inflammasome activation. Given the relationship between NETosis, the inflammasome, and COVID-19 pathology, the ability of disulfiram to target these pathways, treatments with disulfiram could provide substantial clinical benefit.

In addition to improving host response, disulfiram may have antiviral effects on SARS-CoV2. Disulfiram has been shown to inhibit papain-like proteases of deadly coronaviruses such as Middle East respiratory syndrome coronavirus (MERS-CoV) and SARS-CoV1, which may disrupt the replication and IFN suppression mechanisms of these viruses. This experiment is performed by contacting the virus-infected cells with different concentrations of disulfiram in combination of TBHQ. Cell parameters such as cytokine levels and morphological/cellular phenotypes are assayed to demonstrate potential to improve old immune response to infection.

Example 3: Synergistic Effect of Disulfiram and TBHQ

A luciferase assay was performed as described briefly: 125 k THP1 pyroptosis reporter cells/ml final density were plated on 384 well plates and incubated with disulfiram, TBHQ, or disulfiram and TBHQ for 20 minutes. 1 μg/ml LPS was added to the wells, and the plate was incubated for 3 hours, followed by addition of 10 μM nigericin. After three hours, supernatants were harvested and the presence of HMGB1 luciferase reporter protein was quantified using QUANTI-Luc.

Figure 2:
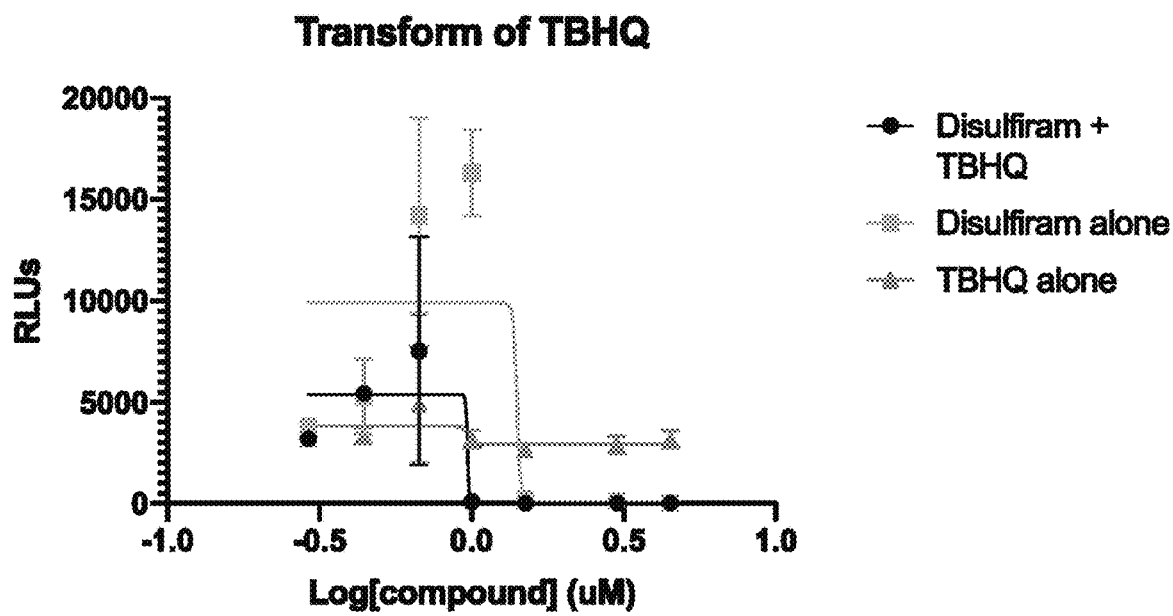
FIG. 2 shows the effect of cells treated with disulfiram alone, tert-Butylhydroquinone (TBHQ) alone, or disulfiram and TBHQ in combination at different concentrations.
Figure 3:
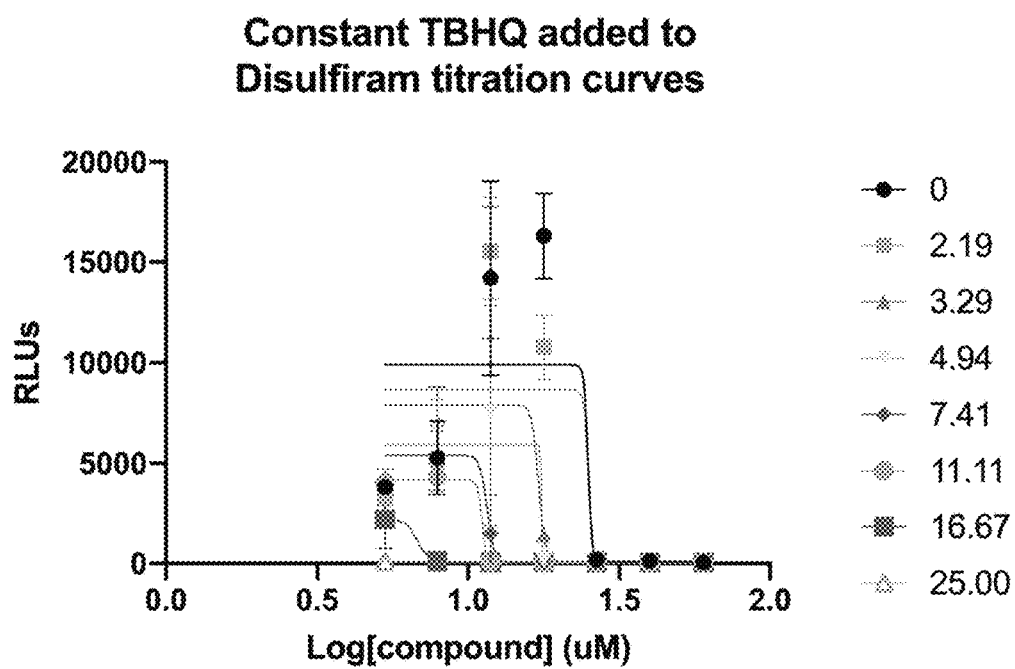
FIG. 3 shows the effect of cells treated with TBHQ and different concentrations of disulfiram.

FIG. 2 shows the effect on pyroptosis of the combination of disulfiram and TBHQ as compared to each individual compound. FIG. 3 shows the potentiating effects of varying constant concentrations of TBHQ added to disulfiram titration curves.

Inhibition of pyroptosis was assessed by inducing inflammasome activation in THP1 HMGB1 Lucia cells (Invivogen). These cells code for a luciferase reporter protein (HMGB1) that is released from cells during pyroptosis. HMGB1 levels in the supernatant can therefore be used to quantify pyroptosis.

Concentration matrices of disulfiram titration curves mixed with titration curves of TBHQ were tested. Disulfiram curves at each concentration of TBHQ were plotted and fit using a log(agonist) vs. response variable slope (four parameters) least squares fit model. The diagonal of each matrix was representative of a dose response curve of disulfiram plus TBHQ combinations titrated at a constant ratio.

Synergy Assessment of Disulfiram Combinations

Synergy fold ratio was measured by calculating the ratio of actual effect over expected effect: [(TBHQ+disulfiram)/no treatment]/[(disulfiram alone/no treatment)×(TBHQ alone/no treatment)] at each concentration combination. Values greater than 1 were considered synergistic.

Synergy using the Loewe additivity model was calculated using synergyfinder package on R (software environment for statistical computing and graphics; see the World Wide Web (at) /bioconductor.org/packages/release/bioc/vignettes/synergyfinder/inst/doc/synergyfinder.pdf, the contents of which is incorporated by reference in its entirety). The Loewe additivity model assumes the null hypothesis that a combination of drugs is the same as increasing the concentration of either drug alone (i.e. the effect is simply additive rather than the drugs interacting to produce a greater effect).

$y_e$ is the effect as if a drug is combined with itself, i.e., $y^e = y_1(x_1+x_2) = y_2(x_1+x_2)$.

Using R, the synergy score is calculated using ye, and determined to be the difference between the observed effect and the expected effect. Score negativity or positivity determines whether the combination is synergistic or antagonist, respectively. Loewe S. (1953), The problem of synergism and antagonism of combined drugs. Arzneimittelforschung 3, 285-290; Loewe, S. (1928). Die quantitativen probleme der pharmakologie. Ergebnisse Physiol. 27, 47-187, the contents of which is incorporated by referenced in its entirety.

Figures 4A, 4B:
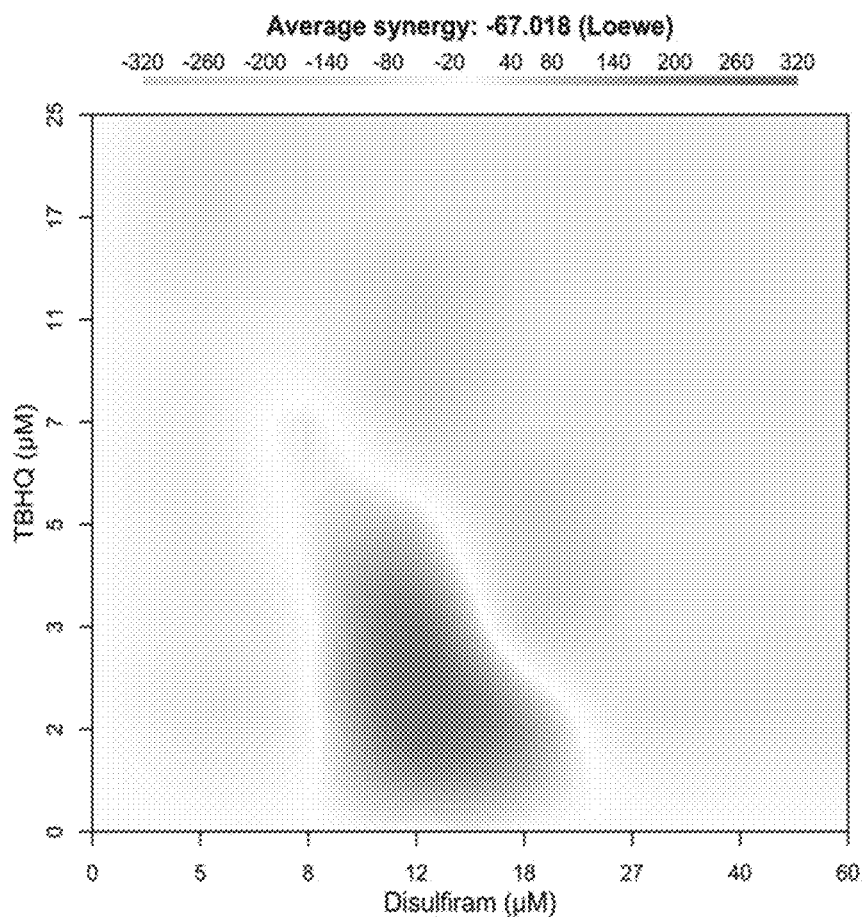
FIG. 4A to FIG. 4C show synergistic effects of TBHQ on disulfiram activity.
Figures 4C, 5:
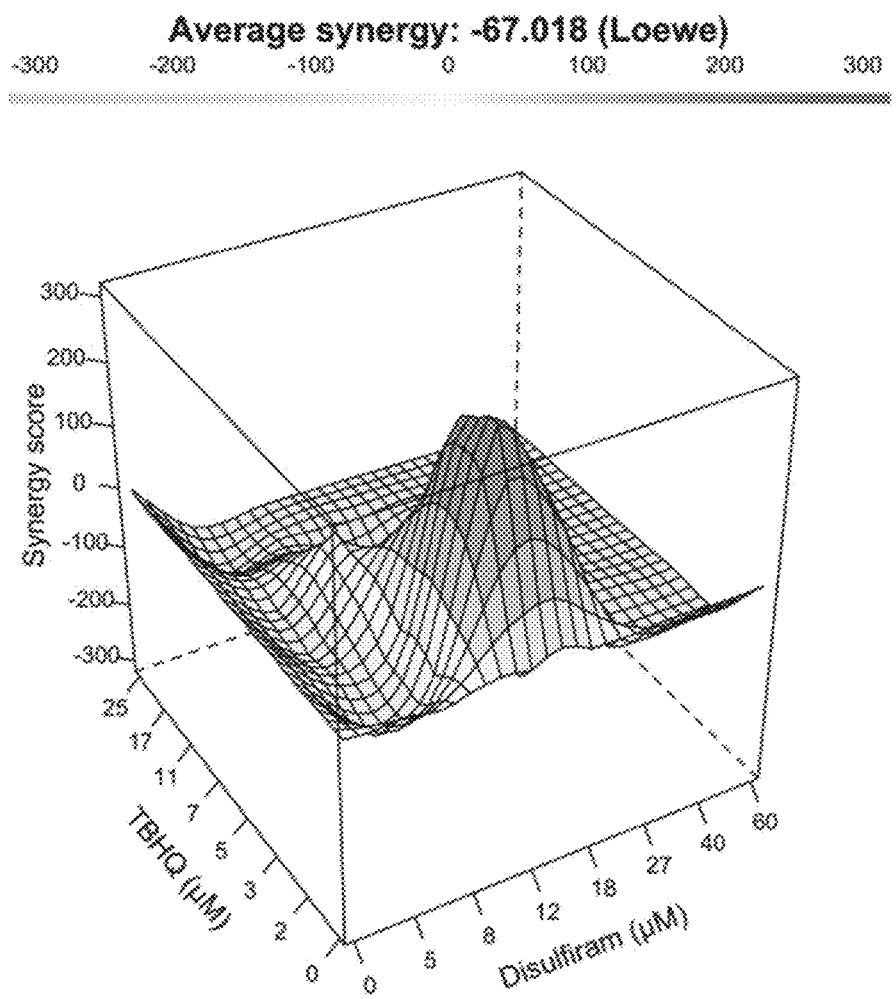
FIG. 5 is a table showing the percent difference in IC50 between disulfiram alone vs. disulfiram and TBHQ at various concentrations or constant ratio (last column). TBHQ combined with disulfiram shifts the IC50 to the left relative to disulfiram alone in a dose-dependent manner. TBHQ has no effect on pyroptosis inhibition or a clear IC50, indicating effects on early inhibition and shifted IC50 is synergistic.

FIG. 4A to FIG. 4C show the synergistic effect of the combination of disulfiram and TBHQ mediated inhibition of pyroptosis.

IC50 Calculations

IC50s were calculated using the log(agonist) vs. response variable slope (four parameters) least squares fit model from the GraphPad Prism software package.

The percent difference between disulfiram alone and each disulfiram+TBHQ curve was calculated, and two replicates for each condition were averaged. Statistical significance was determined using a standard Student's t-test (unpaired, 2-tailed).

Individual curves for disulfiram alone, TBHQ alone, and the combination of the two were plotted as log of the relative concentrations of each. In these experiments, disulfiram and TBHQ were titrated equally with different starting concentrations of disulfiram and TBHQ and so the relative ratio of disulfiram:TBHQ was maintained across the entire curve. The concentrations were normalized so that 1 is set as the median for each curve, and the curves are plotted as 1.5× dilution series.

Curves of disulfiram+constant concentrations of TBHQ were plotted using the log of disulfiram concentration.

FIG. 5 is a table showing the percent leftward shift in IC50 mediated by TBHQ relative to disulfiram alone in a dose-dependent matter, while TBHQ alone has no effect on pyroptosis inhibition or IC50. Accordingly, these data show synergistic effects on pyroptotic inhibition when cells are subjected to a combination of disulfiram and TBHQ.

Example 4: Methods that Comprise Administering Disulfiram and TBHQ

In this example, a composition comprising disulfiram and TBHQ, or distinct compositions of a first composition comprising disulfiram and a second composition comprising TBHQ are administered to a mammal, e.g., a human, for increasing lifespan, for preventing or treating a disease including an aging-related disorder, for reducing a symptom of aging, and/or boosting an immune system (e.g., for treating an infection).

The dose of disulfiram is from about 5 mg to about 500 mg. The dose of the TBHQ is from about 0.001 mg to about 280 mg.

Administration of the compositions is by intravenous injection or infusion, intraperitoneal injection, intramuscular injection, or subcutaneous injection, with a dose depending on the quantity of composition needing to be administered. Alternately, the compositions are administered orally, by inhalation, or topically. Combinations of administration routes may be used.

The mammal's lifespan is measured and the presence, absence, and/or severity of various aging-related disorders are determined; these are compared to control mammals and/or to historical controls to determine the effectiveness of the composition administered.

The mammal may be aged or not aged.

The mammal may have a healthy immune system or the mammal may have an unhealthy immune system, dysfunctional immune system, and/or weakened immune system.

Illustrative diseases treated in this example may be asthma, deafness, or a viral infections and an illustrative symptom thereof may be sepsis.

Assays and formulations used in this example are related to those described in US20190228840, the entire contents of which is incorporated by reference its entirety.

Example 5: Methods for Preventing and/or Treating a Respiratory Disease or Disorder In this example, a composition comprising disulfiram and TBHQ, or distinct compositions of a first composition comprising disulfiram and a second composition comprising TBHQ are administered to a mammal, e.g., a human, for preventing and/or treating a respiratory disease or disorder, e.g., acute lung injury (ALI) and/or acute respiratory distress syndrome (ARDS).

The dose of disulfiram is from about 5 mg to about 500 mg. The dose of the TBHQ is from about 0.001 mg to about 280 mg.

Administration of the compositions is by intravenous injection or infusion, intraperitoneal injection, intramuscular injection, or subcutaneous injection, with a dose depending on the quantity of composition needing to be administered. Alternately, the compositions are administered orally, by inhalation, or topically. Combinations of administration routes may be used.

Treatment is identified as an improvement in the administered mammal in one or more of the following symptoms severe shortness of breath, labored and unusually rapid breathing, low blood pressure, and confusion and extreme tiredness. The improvement may be relative to the pre-administration state for the mammal.

The mammal may be aged or not aged.

The underlying cause for the ALI and/or ARDS may be sepsis (e.g., a serious and widespread infection of the bloodstream); inhalation of a harmful substance (e.g., smoke, chemical fumes, asbestos, dust, particulates, vomit, and water); viral or bacterial pneumonia (which may affect up to all five lobes of the lungs) and other respiratory disorders including those caused by a coronavirus (e.g., SARS, MERS, and COVID-19), influenzas (influenza A, influenza B, or parainfluenza), pneumococcal infection, adenovirus, respiratory syncytial virus (RSV), enterovirus and/or other respiratory viral infections; and a head, chest or other major injury; or another cause (e.g., pancreatitis which is inflammation of the pancreas, a massive blood transfusion, and severe burns).

In some embodiments, ALI differs from ARDS in that ALI exists during early stage of a respiratory disease and ARDS exists during a later state of the respiratory disease.

In some embodiments, the composition or compositions prevent or treat idiopathic pulmonary fibrosis and/or chronic obstructive pulmonary disease.

Example 6: Methods for Improving a Vaccine Response

In this example, a composition comprising disulfiram and TBHQ, or distinct compositions of a first composition comprising disulfiram and a second composition comprising TBHQ are administered to a mammal, e.g., a human, for improving effectiveness of a vaccine that is administered to the mammal.

The dose of disulfiram is from about 5 mg to about 500 mg. The dose of the TBHQ is from about 0.001 mg to about 280 mg.

The compositions may be administered by intravenous injection or infusion, intraperitoneal injection, intramuscular injection, or subcutaneous injection, with a dose depending on the quantity of composition needing to be administered. Alternately, the composition may be administered orally, by inhalation, or topically. Combinations of administration routes may be used.

Administration of the vaccine may be by intravenous injection or infusion, intraperitoneal injection, intramuscular injection, or subcutaneous injection, with a dose depending on the quantity of composition needing to be administered. Alternately, the vaccine may be administered orally, by inhalation, or topically.

In some cases, the composition(s) comprising the combination of disulfiram and/or TBHQ and the vaccine are administered contemporaneously. In other cases, the vaccine is administered subsequent to the administration of the combination(s) of disulfiram and/or one or more additional ingredients. In some cases, the vaccine is administered before the administration of the combination(s) of disulfiram and/or TBHQ. A subject may be administered vaccines and/or combination(s) of disulfiram and/or one TBHQ multiple times and in any order.

The vaccine may be a Chickenpox vaccine, Coronavirus vaccine, Diphtheria vaccine, Hepatitis A vaccine, Hepatitis B vaccine, *Haemophilus influenzae* type b vaccine, Human immunodeficiency virus (HIV) vaccine, Human papillomavirus vaccine, influenza vaccine, Japanese encephalitis vaccine, Measles, mumps, or rubella (including MMR combined vaccine) vaccine, Meningococcal disease vaccine, Pneumococcal disease vaccine, Polio vaccine, Rabies vaccine, Respiratory syncytial virus (RSV) vaccine, Rotavirus vaccine, Shingles vaccine, Smallpox vaccine, Tetanus vaccine, Varicella virus vaccine, Whooping cough (part of the DTaP combined vaccine) vaccine, or Yellow fever vaccine. In embodiments, the vaccine is a coronavirus vaccine. In embodiments, the coronavirus vaccine is directed against Sars-CoV-2.

The mammal may be aged or not aged.

The mammal may have a healthy immune system or the mammal may have an unhealthy immune system, dysfunctional immune system, and/or weakened immune system.

The mammal's ability to fend off a subsequent infection is determined and compared to mammals and/or historical controls who were only administered the vaccine.

The mammal's ability to later produce antibodies directed to an infectious agent (related to the vaccine) is determined and compared to mammals and/or historical controls who were only administered the vaccine.

Example 7: Methods for Treating Skin Disorders

In this example, a composition comprising disulfiram and TBHQ, or distinct compositions of a first composition comprising disulfiram and a second composition comprising TBHQ are administered to a mammal, e.g., a human, for treating a skin disorder.

The dose of disulfiram is from about 5 mg to about 500 mg. The dose of the TBHQ is from about 0.001 mg to about 280 mg.

The compositions may be administered orally or topically, with a dose depending on the quantity of composition needing to be administered. The compositions may be formulated as a gel, lotion, ointment, cream, suspension, paste, liniment, powder, tincture, or aerosol or administered via an impregnated solid support (e.g., a patch). Alternately, the composition may be administered by injection or by inhalation. The composition(s) may be administered orally. Combinations of administration routes may be used.

The mammal has a skin disorder, e.g., wrinkles, which may be a result of photoaging or related to actinic keratosis. Other skin disorders the mammal may have includes dermal atrophy (thinning of the skin), lentigines (aging spots), vaginal atrophy, prolonged/inefficient wound healing, and/or xerosis cutis (skin dryness). In examples, the mammal has moderate skin aging (i.e., Glogau Classification III).

The composition's or compositions' ability to treat a skin disorder, e.g., wrinkles, is determined and compared to the mammal before administration and/or to historical controls who were not administered the composition or compositions. For example, the determination relates to a change in the Glogau Classification.

Example 8: Methods for Treating Dry Eye

In this example, a composition comprising disulfiram and TBHQ, or distinct compositions of a first composition comprising disulfiram and a second composition comprising TBHQ are administered to a mammal, e.g., a human, for treating dry eye.

The dose of disulfiram is from about 5 mg to about 500 mg. The dose of the TBHQ is from about 0.001 mg to about 280 mg.

The compositions may be administered topically, with a dose depending on the quantity of composition needing to be administered. The compositions may be formulated as eye drops or as eye ointments.

The composition's or compositions' ability to treat dry eyes, is determined and compared to the mammal before administration and/or to historical controls who were not administered the composition or compositions.

Example 9: Methods for Treating Alopecia

In this example, a composition comprising disulfiram and TBHQ, or distinct compositions of a first composition comprising disulfiram and a second composition comprising TBHQ are administered to a mammal, e.g., a human, for treating alopecia.

The dose of disulfiram is from about 5 mg to about 500 mg. The dose of the TBHQ is from about 0.001 mg to about 280 mg.

The compositions may be administered topically, with a dose depending on the quantity of composition needing to be administered. The compositions may be formulated as a gel, lotion, ointment, cream, suspension, paste, liniment, powder, tincture, or aerosol or administered via an impregnated solid support (e.g., a patch). Alternately, the composition may be administered by injection or by inhalation. The composition(s) may be administered orally. Combinations of administration routes may be used.

The composition's or compositions' ability to treat alopecia, is determined and compared to the mammal before administration and/or to historical controls who were not administered the composition or compositions.

Example 10: Methods for Treating a Skin Cancer

In this example, a composition comprising disulfiram and TBHQ, or distinct compositions of a first composition comprising disulfiram and a second composition comprising TBHQ are administered to a mammal, e.g., a human, for treating a skin cancer, e.g., (e.g., basal cell carcinoma (BCC) and squamous cell carcinoma (SCC)).

The dose of disulfiram is from about 5 mg to about 500 mg. The dose of the TBHQ is from about 0.001 mg to about 280 mg.

The compositions may be administered topically, with a dose depending on the quantity of composition needing to be administered. The compositions may be formulated as a gel, lotion, ointment, cream, suspension, paste, liniment, powder, tincture, or aerosol or administered via an impregnated solid support (e.g., a patch). Alternately, the composition may be administered by injection or by inhalation. The composition(s) may be administered orally. Combinations of administration routes may be used.

The composition's or compositions' ability to treat the skin cancer, e.g., BCC and SCC, is determined and compared to the mammal before administration and/or to historical controls who were not administered the composition or compositions.

Example 11: Methods that Comprise Administering a First Composition and a Second Composition In this example, a first composition comprises a therapeutically effective amount of disulfiram and a second composition comprising TBHQ are administered to a mammal for increasing lifespan, for preventing or treating a disease including an aging-related disorder, for reducing a symptom of aging, and/or boosting an immune system.

The dose of disulfiram is from about 5 mg to about 500 mg. The dose of the TBHQ is from about 0.001 mg to about 280 mg.

The first composition is administered orally, by inhalation, injection, or topically. The second composition is administered orally, by inhalation, injection, or topically. The administration route of the first composition and the second composition may be the same or may be different.

The first composition may be administered before the second composition is administered.

The first composition may be administered after the second composition is administered.

The first composition and the second composition may be administered contemporaneously (either by combining the two compositions or by administering the two compositions at nearly the same time).

The mammal's lifespan is measured and the presence, absence, and/or severity of various aging-related disorders are determined; these are compared to control mammals and/or to historical controls to determine the effectiveness of the first composition administered.

What is claimed is:

1. A method for inhibiting and/or reducing pyroptotic cell death in a cell, the method comprising contacting the cell with an active agent that is disulfiram and a potentiating ingredient that is tert-Butylhydroquinone (TBHQ), thereby inhibiting and/or reducing pyroptotic cell death, wherein the amount of disulfiram is from about 5 mg to about 500 mg and the amount of TBHQ is from about 0.02% to about 56% by weight of disulfiram and a combination of disulfiram and TBHQ provides a synergistic effect.

2. The method of claim 1, wherein disulfiram and TBHQ are included in one composition and the composition consists essentially of disulfiram and TBHQ.

3. The method of claim 1, wherein the method comprises contacting the cell with a first composition consisting essentially of disulfiram and contacting the cell with a second composition consisting essentially TBHQ.

4. The method of claim 1, wherein inhibiting and/or reducing pyroptotic cell death in the cell increases the lifespan of the cell.

5. A method for inhibiting and/or reducing pyroptotic cell death in a cell, the method comprising contacting the cell with an active agent that is disulfiram and a potentiating ingredient that is tert-Butylhydroquinone (TBHQ), thereby inhibiting and/or reducing pyroptotic cell death, wherein the amount of disulfiram is from about 5 mg to about 500 mg and the amount of TBHQ is from about 0.02% to about 56% by weight of disulfiram and a combination of disulfiram and TBHQ provides a synergistic effect, wherein the combination of disulfiram and TBHQ treats acute lung injury (ALI), acute respiratory distress syndrome (ARDS), idiopathic pulmonary fibrosis, chronic obstructive pulmonary disease, dry eye, actinic keratosis, alopecia, and/or skin cancer.

6. The method of claim 1, wherein the combination of disulfiram and TBHQ inhibits and/or reduces a pathological inflammatory response, alters a T-cell's age, and/or alters mitochondrial function in the cell.

7. A method for boosting activity of an immune cell, the method comprising contacting the immune cell with an active agent that is disulfiram and a potentiating ingredient that is tert-Butylhydroquinone (TBHQ), thereby boosting activity of the immune cell, wherein the amount of disulfiram is from about 5 mg to about 500 mg and the amount of TBHQ is from about 0.02% to about 56% by weight of disulfiram and a combination of disulfiram and TBHQ provides a synergistic effect.

8. The method of claim 7, wherein disulfiram and TBHQ are included in one composition and the composition consists essentially of disulfiram and TBHQ.

9. The method of claim 7, wherein the method comprises contacting the immune cell with a first composition consisting essentially of disulfiram and contacting the cell with an at least second composition consisting essentially TBHQ.

10. The method of claim 7, wherein boosting activity of the immune cell increases an effective immune response against an infectious agent and/or an atypical cell.

11. The method of claim 7, wherein boosting activity of the immune cell improves the immune cell's response against a component contained in a vaccine, wherein the component contained in the vaccine is an antigen obtained from, related to, homologous to, or expressed by an infectious agent.

12. The method of claim 7, wherein boosting activity of the immune cell comprises inhibiting a pathological immune response.

13. The method of claim 12, wherein boosting activity of the immune cell minimizes overactive immune cell activity.

14. The method of claim 1, wherein the synergistic effect is characterized using a Synergy Fold Ratio and/or using the Loewe Additivity Model.

15. The method of claim 7, wherein the synergistic effect is characterized using a Synergy Fold Ratio and/or using the Loewe Additivity Model.

16. The method of claim 5, wherein disulfiram and TBHQ are included in one composition and the composition consists essentially of disulfiram and TBHQ.

17. The method of claim 5, wherein the method comprises contacting the cell with a first composition consisting essentially of disulfiram and contacting the cell with an at least second composition consisting essentially TBHQ.

18. The method of claim 5, wherein the synergistic effect is characterized using a Synergy Fold Ratio and/or using the Loewe Additivity Model.

* * * * *